US011895915B2

(12) United States Patent
Choi et al.

(10) Patent No.: US 11,895,915 B2
(45) Date of Patent: Feb. 6, 2024

(54) ORGANIC LIGHT EMITTING DIODE AND ORGANIC LIGHT EMITTING DEVICE HAVING THE SAME

(71) Applicants: LG Display Co., Ltd., Seoul (KR); LG CHEM, LTD., Seoul (KR)

(72) Inventors: Hyong-Jong Choi, Paju-si (KR); Tae-Ryang Hong, Paju-si (KR); Joong-Hwan Yang, Paju-si (KR); Jun-Yun Kim, Paju-si (KR); Wan-Pyo Hong, Daejeon (KR); Jin-Joo Kim, Daejeon (KR); Hong-Sik Yoon, Seoul (KR)

(73) Assignees: LG DISPLAY CO., LTD, Seoul (KR); LG CHEM, LTD., Seoul (KR)

(*) Notice: Subject to any disclaimer, the term of this patent is extended or adjusted under 35 U.S.C. 154(b) by 637 days.

(21) Appl. No.: 16/521,369

(22) Filed: Jul. 24, 2019

(65) Prior Publication Data
US 2020/0127214 A1 Apr. 23, 2020

(30) Foreign Application Priority Data
Oct. 22, 2018 (KR) .................. 10-2018-0126164

(51) Int. Cl.
  *H10K 85/60* (2023.01)
  *C07D 405/14* (2006.01)
  (Continued)

(52) U.S. Cl.
  CPC ....... *H10K 85/6572* (2023.02); *C07D 405/14* (2013.01); *C07D 409/14* (2013.01);
  (Continued)

(58) Field of Classification Search
  CPC ............. H01L 51/0072; H01L 51/0071; H01L 51/0073; H01L 51/0074; C07D 405/14;
  (Continued)

(56) References Cited

U.S. PATENT DOCUMENTS

2011/0006670 A1* 1/2011 Katakura ............. C07D 403/10
                                                          548/402
2016/0087227 A1 3/2016 Kim et al.
(Continued)

FOREIGN PATENT DOCUMENTS

CN       106716668 A     5/2017
KR   10-2015-0083470 A   7/2015
(Continued)

OTHER PUBLICATIONS

Machine Translation of WO2013031345 (Year: 2013).*
(Continued)

*Primary Examiner* — Jenna N Chandhok
(74) *Attorney, Agent, or Firm* — Birch, Stewart, Kolasch & Birch, LLP

(57) ABSTRACT

Disclosed is an organic light emitting diode (OLED) comprising at least one emitting unit that includes a first compound, which may have a bipolar property, a second compound, which may have a delayed fluorescent property, and a third compound, which may have narrow FWHM (full width at half maximum) and a fluorescent property, and an organic light emitting device including the OLED. Further the compounds have defined relative LUMO and HOMO energies. The OLED and the organic light emitting device has enhanced luminous efficiency, color purity and luminous life span as well as low driving voltage.

17 Claims, 7 Drawing Sheets

(51) Int. Cl.
 *C09K 11/06* (2006.01)
 *C07D 409/04* (2006.01)
 *C07D 491/048* (2006.01)
 *C07D 487/04* (2006.01)
 *H10K 50/11* (2023.01)
 *H10K 101/10* (2023.01)
 *H10K 101/30* (2023.01)
 *H10K 101/40* (2023.01)
 *C07D 409/14* (2006.01)

(52) U.S. Cl.
 CPC ....... *C07D 487/04* (2013.01); *C07D 491/048* (2013.01); *C09K 11/06* (2013.01); *H10K 85/615* (2023.02); *H10K 85/657* (2023.02); *H10K 85/6574* (2023.02); *H10K 85/6576* (2023.02); *C09K 2211/1018* (2013.01); *H10K 50/11* (2023.02); *H10K 2101/10* (2023.02); *H10K 2101/30* (2023.02); *H10K 2101/40* (2023.02)

(58) Field of Classification Search
 CPC .............. C07D 409/14; C07D 491/048; H10K 85/6572; H10K 85/615; H10K 85/657; H10K 85/6574; H10K 85/6576
 See application file for complete search history.

(56) References Cited

U.S. PATENT DOCUMENTS

2017/0062718 A1* 3/2017 Numata ................ C09K 11/025
2017/0352816 A1* 12/2017 Jeon ..................... H01L 51/0067
2018/0186819 A1 7/2018 Kim et al.
2021/0115282 A1* 4/2021 Mangold .............. H01L 33/502
2021/0202864 A1* 7/2021 Nakanotani .......... C07D 209/88

FOREIGN PATENT DOCUMENTS

KR 10-2017-0062457 A 6/2017
KR 10-2017-0136256 A 12/2017
WO WO 2013/031345 A1 3/2013
WO WO-2013031345 A1 * 3/2013 .......... H01L 51/504
WO WO 2013/047981 A1 4/2013

OTHER PUBLICATIONS

Xiao (Xiao, Jing. "Balancing the White Emission of OLEDs by a Tandem Structure With an Effective Charge Generation Layer." Synthetic Metals. 172 (2013): 11-13. (Year: 2013).*

* cited by examiner

ORGANIC LIGHT EMITTING DIODE AND ORGANIC LIGHT EMITTING DEVICE HAVING THE SAME

CROSS-REFERENCE TO RELATED APPLICATIONS

This application claims the benefit under 35 U.S.C. § 119(a) of Korean Patent Application No. 10-2018-0126164, filed in Republic of Korea on Oct. 22, 2018, which is incorporated herein by reference in its entirety.

BACKGROUND

Technical Field

The present disclosure relates to an organic light emitting diode, and more specifically, to an organic light emitting diode with superior luminous efficiency, color purity and luminous life span and an organic light emitting device including the same.

Description of the Related Art

As a display device becomes larger, there exists a need for a flat display device with reduced size. Among the flat display devices, a display device using an organic light emitting diode (OLED) has come into the spotlight.

In the OLED, when electrical charges are injected into an emitting material layer between an electron injection electrode (i.e., cathode) and a hole injection electrode (i.e., anode), electrical charges are combined to be paired, and then emit light as the combined electrical charges are canceled.

The OLED can be formed on a flexible transparent substrate such as a plastic substrate. In addition, the OLED can be driven at a lower voltage of 10 V or less. Moreover, the OLED has relatively lower power consumption for driving compared to the plasma display panel and inorganic electroluminescent devices, and color purity of the OLED is very high. Further, since the OLED can display various colors such as green, blue, red and the like, the OLED display device has attracted a lot of attention as a next-generation display device that can replace a liquid crystal display device (LCD).

BRIEF SUMMARY

Accordingly, the present disclosure is directed to an organic light emitting diode and an organic light emitting device including the diode that substantially decreases one or more of the limitations and disadvantages of the related art.

An object of the present disclosure is to provide an organic light emitting diode and an organic light emitting device that can enhance luminous efficiency and color purity.

Another object of the present disclosure is to provide an organic light emitting diode and an organic light emitting device with lower driving voltage and power consumption, and improves the OLED luminous life span.

Additional features and advantages of the disclosure will be set forth in the description which follows, and in part will be apparent from the description, or may be learned by practice of the disclosure. The objectives and other advantages of the disclosure will be realized and attained by the structure particularly pointed out in the written description and claims hereof as well as the appended drawings.

According to an aspect, the present disclosure provides an organic light emitting diode (OLED) that comprises first and second electrodes facing each other; and at least one emitting unit disposed between the first and second electrodes and including an emitting material layer, wherein the emitting material layer includes a first compound, a second compound and a third compound, wherein a Lowest Unoccupied Molecular Orbital (LUMO) energy level (LUMO$^H$) of the first compound and a LUMO energy level (LUMO$^{TD}$) of the second compound satisfy the relationship in Equation (1) below, wherein a Highest Occupied Molecular Orbital (HOMO) energy level (HOMO$^H$) of the first compound, a HOMO energy level (HOMO$^{TD}$) of the second compound and a HOMO energy level (HOMO$^{FD}$) of the third compound satisfy the following relationship in Equation (2) below, wherein an excited state singlet energy level ($S_1^H$) of the first compound is higher than an excited state singlet energy level ($S_1^{TD}$) of the second compound, and wherein an excited state singlet energy level ($S_1^{TD}$) of the second compound is higher than an excited state singlet energy level ($S_1^{FD}$) of the third compound.

$$|LUMO^H| - |LUMO^{TD}| \leq 0.8 \text{ eV} \quad (1)$$

$$|HOMO^H| \geq |HOMO^{TD}| \geq |HOMO^{FD}| \quad (2)$$

According to another aspect, the present disclosure provides an organic light emitting diode (OLED) that comprises first and second electrodes facing each other; and at least one emitting unit disposed between the first and second electrodes and including an emitting material layer, wherein the emitting material layer includes a first compound, a second compound and a third compound, wherein a Lowest Unoccupied Molecular Orbital (LUMO) energy level of the first compound (LUMO$^H$) and a LUMO energy level of the second compound (LUMO$^{TD}$) satisfy the relationship in Equation (1) above, wherein a Highest Occupied Molecular Orbital (HOMO) energy level of the first compound (HOMO$^H$), a HOMO energy level of the second compound (HOMO$^{TD}$) and a HOMO energy level of the third compound (HOMO$^{FD}$) satisfy the relationship in Equation (2) above, and wherein the first compound includes an organic compound having the following structure of Chemical Formula 1:

Chemical Formula 1

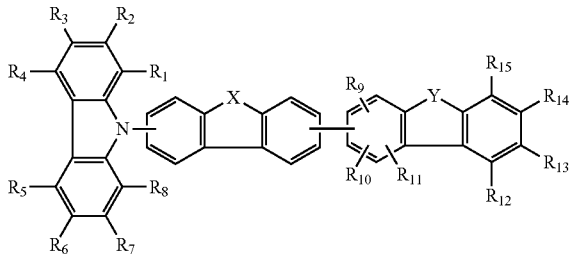

wherein each of $R_1$ to $R_{15}$ is independently hydrogen, deuterium, tritium, silyl group, $C_1$~$C_{10}$ alkyl group, $C_1$~$C_{10}$ alkoxy group, $C_1$~$C_{10}$ alkyl amino group, $C_5$-$C_{30}$ aryl group, $C_4$~$C_{30}$ hetero aryl group, $C_5$~$C_{30}$ alkyl aryl group, $C_4$~$C_{30}$ hetero alkyl aryl group, $C_5$-$C_{30}$ aryloxyl group, $C_4$-$C_{30}$ hetero aryloxyl group, $C_5$~$C_{30}$ aryl amino group or $C_4$~$C_{30}$ hetero aryl amino group, or two adjacent groups among $R_1$ to $R_{15}$ forms a fused aryl ring or a fused heteroaryl ring each of which is unsubstituted or substituted with $C_5$~$C_{30}$ aryl group or $C_4$~$C_{30}$ hetero aryl group; each of X and Y is independently oxygen (O) or sulfur (S).

According to still another aspect, the present disclosure provides an organic light emitting device that comprises a substrate and the OLED of the present disclosure disposed over the substrate, as described above.

It is to be understood that both the foregoing general description and the following detailed description are examples and are explanatory and are intended to provide further explanation of the disclosure as claimed.

BRIEF DESCRIPTION OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

DETAILED DESCRIPTION

Reference will now be made in detail to aspects of the disclosure, examples of which are illustrated in the accompanying drawings.

Organic Light Emitting Device

Figure 1:
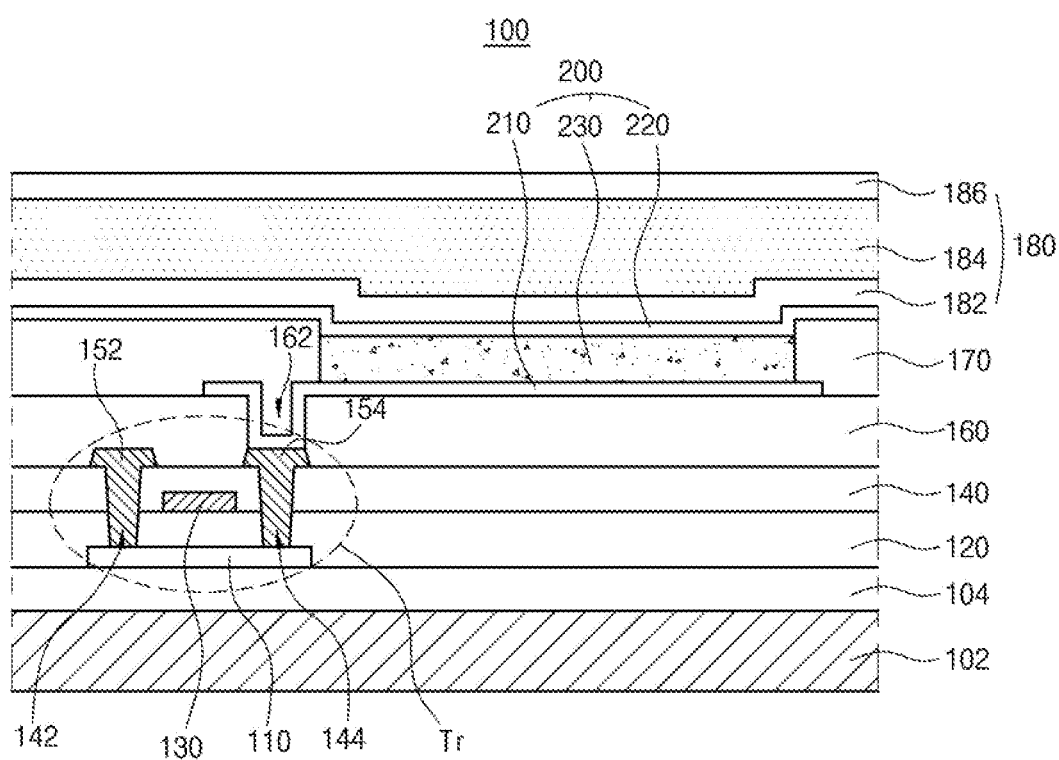
FIG. 1 is a schematic cross-sectional view illustrating an organic light emitting display device of the present disclosure.

The present disclosure relates to an organic light emitting diode (OLED) that has an emitting material layer including a first compound as a host and second and third compounds each of which has a predetermined energy levels compared to the first compound, and an organic light emitting device having the OLED. The OLED of the present disclosure may be applied to an organic light emitting device such as an organic light emitting display device and an organic light emitting illumination device. A display device having the OLED of the present disclosure will be explained. FIG. 1 is a schematic cross-sectional view illustrating an organic light emitting display device of the present disclosure. All components of the organic light emitting display device according to all embodiments of the present disclosure are operatively coupled and configured.

As illustrated in FIG. 1, the organic light emitting display device 100 comprises a substrate 102, a thin-film transistor Tr on the substrate 102, and an organic light emitting diode 200 connected to the thin film transistor Tr. The thin-film transistor Tr includes a semiconductor layer 110, a gate electrode 130, a source electrode 152 and a drain electrode 154.

The substrate 102 may include, but are not limited to, glass, thin flexible material and/or polymer plastics. For example, the flexible material may be selected from the group, but are not limited to, polyimide (PI), polyethersulfone (PES), polyethylenenaphthalate (PEN), polyethylene terephthalate (PET), polycarbonate (PC) and combination thereof. The substrate 102, over which the thin film transistor Tr and the organic light emitting diode 200 are arranged, forms an array substrate.

A buffer layer 104 may be disposed over the substrate 102, and the thin film transistor Tr is disposed over an optional buffer layer 104. The buffer layer 104 may be omitted.

A semiconductor layer 110 is disposed over the buffer layer 104. In one exemplary embodiment, the semiconductor layer 110 may include oxide semiconductor materials. In this case, a light-shied pattern may be disposed under the semiconductor layer 110, and the light-shied pattern can prevent light from being incident toward the semiconductor layer 110, and thereby, preventing the semiconductor layer 110 from being deteriorated by the light. Alternatively, the semiconductor layer 110 may include, but are not limited to, polycrystalline silicon. In this case, opposite edges of the semiconductor layer 110 may be doped with impurities.

A gate insulating layer 120 formed of an insulating material is disposed on the semiconductor layer 110. The gate insulating layer 120 may include, but are not limited to, an inorganic insulating material such as silicon oxide ($SiO_x$) or silicon nitride ($SiN_x$).

A gate electrode 130 made of a conductive material such as a metal is disposed over the gate insulating layer 120 so as to correspond to a center of the semiconductor layer 110. While the gate insulating layer 120 is disposed over a whole area of the substrate 102 in FIG. 1, the gate insulating layer 120 may be patterned identically as the gate electrode 130.

An interlayer insulating layer 140 formed of an insulating material is disposed on the gate electrode 130 with covering over an entire surface of the substrate 102. The interlayer insulating layer 140 may include, but are not limited to, an inorganic insulating material such as silicon oxide ($SiO_x$) or silicon nitride ($SiN_x$), or an organic insulating material such as benzocyclobutene or photo-acryl.

The interlayer insulating layer 140 has first and second semiconductor layer contact holes 142 and 144 that expose both sides of the semiconductor layer 110. The first and second semiconductor layer contact holes 142 and 144 are disposed over both sides of the gate electrode 130 with spacing apart from the gate electrode 130. The first and second semiconductor layer contact holes 142 and 144 are formed within the gate insulating layer 120 in FIG. 1. Alternatively, the first and second semiconductor layer contact holes 142 and 144 are formed only within the interlayer insulating layer 140 when the gate insulating layer 120 is patterned identically as the gate electrode 130.

A source electrode 152 and a drain electrode 154, which are made of a conductive material such as a metal, are disposed on the interlayer insulating layer 140. The source electrode 152 and the drain electrode 154 are spaced apart from each other with respect to the gate electrode 130 and contact both sides of the semiconductor layer 110 through the first and second semiconductor layer contact holes 142 and 144, respectively.

The semiconductor layer 110, the gate electrode 130, the source electrode 152 and the drain electrode 154 constitute the thin film transistor Tr, which acts as a driving element. The thin film transistor Tr in FIG. 1 has a coplanar structure in which the gate electrode 130, the source electrode 152 and the drain electrode 154 are disposed over the semiconductor layer 110. Alternatively, the thin film transistor Tr may have an inverted staggered structure in which a gate electrode is disposed under a semiconductor layer and source and drain electrodes are disposed over the semiconductor layer. In this case, the semiconductor layer may include, but are not limited to, amorphous silicon.

Although not shown in FIG. 1, a gate line and a data line, which cross each other to define a pixel region, and a switching element, which is connected to the gate line and the data line, may be further formed in the pixel region. The switching element is connected to the thin film transistor Tr, which is a driving element. Besides, a power line is spaced apart in parallel from the gate line or the data line, and the thin film transistor Tr may further include a storage capacitor configured to constantly keep a voltage of the gate electrode for one frame.

In addition, the organic light emitting display device 100 may include a color filter for absorbing a part of the light emitted from the organic light emitting diode 200. For example, a color filter may absorb a light of specific wavelength such as red (R), green (G) or blue (B). In this case, the organic light emitting display device 100 can implement full-color through the color filter.

For example, when the organic light emitting display device 100 is a bottom-emission type, the color filter may be disposed on the interlayer insulating layer 140 with corresponding to the organic light emitting diode 200. Alternatively, when the organic light emitting display device 100 is a top-emission type, the color filter may be disposed over the organic light emitting diode 200, that is, a second electrode 220.

A passivation layer 160 is disposed on the source and drain electrodes 152 and 154 over the whole substrate 102. The passivation layer 160 has a flat top surface and a drain contact hole 162 that exposes the drain electrode 154 of the thin film transistor Tr. While the drain contact hole 162 is disposed on the second semiconductor layer contact hole 144, it may be spaced apart from the second semiconductor layer contact hole 144.

The organic light emitting diode 200 includes a first electrode 210 that is disposed on the passivation layer 160 and connected to the drain electrode 154 of the thin-film transistor Tr. The organic light emitting diode 200 further includes an emitting unit 230 as an emission layer and a second electrode 220 each of which is disposed sequentially on the first electrode 210.

The first electrode 210 is disposed in each pixel region. The first electrode 210 may be an anode and include, but are not limited to, a conductive material having a relatively high work function value. For example, the first electrode 210 may include, but are not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the likes.

In one exemplary embodiment, when the organic light emitting display device 100 is a top-emission type, a reflective electrode or a reflective layer may be disposed under the first electrode 210. For example, the reflective electrode or the reflective layer may include, but are not limited to, aluminum-palladium-copper (APC) alloy.

In addition, a bank layer 170 is disposed on the passivation layer 160 in order to cover edges of the first electrode 210. The bank layer 170 exposes a center of the first electrode 210.

The emitting unit 230 as an emission layer is disposed on the first electrode 210. In one exemplary embodiment, the emitting unit 230 may have a mono-layered structure of an emitting material layer. Alternatively, the emitting unit 230 may have a multiple-layered structure of at least one charge control or transfer layer, for controlling charge transport, such as a hole injection layer, a hole transport layer, an electron blocking layer, a hole blocking layer, an electron transport layer and/or an electron injection layer as well as an emitting material layer (See, FIGS. 2, 6 and 7). As an example, the organic light emitting diode 200 may have multiple emitting units and at least one charge generation layer disposed between two adjacent emitting units. The emitting unit 230 includes a first compound, a second compound and a third compound. As an example, the first compound may be a host, the second compound may be a delayed fluorescent material and the third compound may be a fluorescent material. These compounds may be included in an emitting material layer. The construction and energy levels of those compounds will be explained in more detail below.

The second electrode 220 is disposed over the substrate 102 above which the emitting unit 230 is disposed. The second electrode 220 may be disposed over a whole display area and may include, but are not limited to, a conductive material having a relatively low work function value compared to the first electrode 210. The second electrode 220 may be a cathode. For example, the second electrode 220 may include, but is not limited to, aluminum (Al), magnesium (Mg), calcium (Ca), silver (Au), alloy thereof or combination thereof such as aluminum-magnesium alloy (Al—Mg).

In addition, an encapsulation film 180 may be disposed over the second electrode 120 in order to prevent outer moisture from penetrating into the organic light emitting diode 200. The encapsulation film 180 may have, but is not limited to, a laminated structure of a first inorganic insulating film 182, an organic insulating film 184 and a second inorganic insulating film 186.

As described above, the emitting unit 230 of the organic light emitting diode 200 may include the first to third compounds. It is possible to improve luminous efficiency, color purity and luminous life span as well as to lower driving voltage of the organic light emitting diode 200 and the organic light emitting display device 100 by appropriately adjusting the energy levels and/or the energy level bandgap of these compounds.

Organic Light Emitting Diode (OLED)

Figure 2:
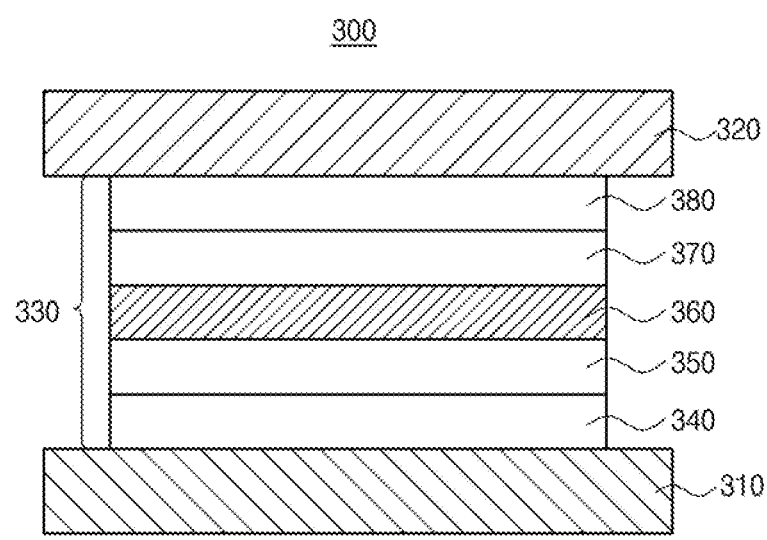
FIG. 2 is a schematic cross-sectional view illustrating an organic light emitting diode in accordance with an exemplary embodiment of the present disclosure.

An organic light emitting diode including three luminous compounds, i.e. the first to third compounds in an emitting material layer according to the present disclosure will be explained. FIG. 2 is a schematic cross-sectional view illustrating an organic light emitting diode in accordance with an exemplary embodiment of the present disclosure.

As illustrated in FIG. 2, the organic light emitting diode (OLED) 300 in accordance with an exemplary embodiment of the present disclosure includes first and second electrodes 310 and 320 facing each other and an emitting unit 330 as an emission layer disposed between the first and second electrodes 310 and 320. In one exemplary embodiment, the emitting unit 330 includes a hole injection layer (HIL) 340, a hole transport layer (HTL) 350, an emitting material layer (EML) 360, an electron transport layer (ETL) 370 and an electron injection layer (EIL) 380 each of which is laminated sequentially from the first electrode 310.

The first electrode 310 may be an anode that provides a hole into the EML 360. As described above, the first electrode 310 may include, but are not limited to, a conductive material having a relatively high work function value, for example, a transparent conductive oxide (TCO). In an exemplary embodiment, the first electrode 310 may include, but is not limited to ITO, IZO, ITZO, SnO, ZnO, ICO, AZO, and the like.

The second electrode 320 may be a cathode that provides an electron into the EML 360. As described above, the second electrode 320 may include, but is not limited to, a conductive material having a relatively low work function values, i.e., a highly reflective material such as Al, Mg, Ca, Ag, alloy thereof, combination thereof, and the like. As an example, each of the first electrode 310 and the second electrode 320 may have a thickness of, but is not limited to, about 30 nm to about 300 nm.

The HIL 340 is disposed between the first electrode 310 and the HTL 350 and improves an interface property between the inorganic first electrode 310 and the organic HTL 350. In one exemplary embodiment, the HIL 340 may include, but are not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino) triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl] benzene (TDAPB), poly(3,4-ethylenedioxythiophene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 340 may be omitted in compliance with a structure of the OLED 300.

The HTL 350 is disposed adjacent to the EML 360 between the first electrode 310 and the EML 360. In one exemplary embodiment, the HTL 350 may include, but is not limited to, N,N'-Diphenyl-N,N'-bis(3-methylphenyl)-1, 1'-biphenyl-4,4'-diamine (TPD), NPB, 4,4'-bis(N-carbazolyl)-1,1'-biphenyl (CBP), Poly[N,N'-bis(4-butylpnehyl)-N,N'-bis(phenyl)-benzidine] (Poly-TPD), Poly[(9,9-dioctylfluorenyl-2,7-diyl)-co-(4,4'-(N-(4-sec-butylphenyl) diphenylamine))] (TFB), Di-[4-(N,N-di-p-tolyl-amino)-phenyl]cyclohexane (TAPC), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

In one exemplary embodiment, each of the HIL 340 and the HTL 350 may be respectively laminated with a thickness of, but are not limited to, about 5 nm to about 200 nm, preferably about 5 nm to about 100 nm.

The EML 360 includes a host doped with dopants in which substantial illumination occurs. Phosphorescent materials, which utilize triplet exciton as well as singlet exciton, show higher luminous efficiency than fluorescent materials, which utilize only the singlet exciton. Accordingly, phosphorescent hosts that can be used with phosphorescent dopants have attracted a lot of attention.

An excited state triplet energy level of the phosphorescent host must be higher than an excited stated triplet energy level of the phosphorescent dopant so as to prevent the triplet energy of the phosphorescent dopant from transferring to the phosphorescent host. The triplet energy of the organic aromatic compounds drops sharply as the organic aromatic compounds have increased conjugation structure or fused rings. Accordingly, the organic materials that can be used as the phosphorescent hosts are extremely limited.

In addition, the phosphorescent hosts are designed to have an energy level bandgap larger than 3.5 to 4.5 eV in order to have high triplet energy levels. When a phosphorescent host having an excessively wide energy level bandgap is used, charge injection and charge transportation becomes poor, and therefore, a high driving voltage is required, which may adversely affect the life span properties of the diode.

In one exemplary embodiment, the EML 360 includes the first compound, the second compound and the third compound. As an example, the first compound may be a host of the EML 360, the second and third compounds may be dopants of the EML 360. Particularly, the second compound may be material having a delayed fluorescence property and the third compound may be material having a fluorescent property.

It is possible to lower a driving voltage as well as to improve luminous efficiency, color purity and luminous life span of the OLED 300 by using the first to third compounds whose energy levels are controlled within the predetermined ranges in the EML 360. Hereinafter, the EML 360, where the first compound is a host, the second compound is a thermally activated delayed fluorescent dopant (T dopant) and the third compound is a fluorescent dopant (F dopant), will be explained.

An organic light emitting diode (OLED) emits light as holes injected from the anode and electrons injected from the cathode are combined to form excitons in an EML and then unstable excited state excitons return to a stable ground state. The external quantum efficiency (EQE; $\eta_{ext}$) of the luminous material applied into the EML may be calculated by product of four parameters, i.e. exciton generation efficiency or singlet-triplet ratio "$\eta_{S/T}$", a charge balance factor "r", radiative quantum efficiency "Φ" and out-coupling efficiency "$\eta_{out-coupling}$".

The singlet-triplet ratio has a maximum value of 0.25 in case of fluorescent materials. Theoretically, when electrons meet holes to form exciton, a singlet exciton of a paired spin and a triplet exciton of an unpaired spin are generated by a ratio of 1:3 by spin arrangements. Only the singlet exciton among the excitons can be involved in emission process and the triplet exciton cannot be involved in the emission process in case of the fluorescent materials.

Charge balance factor "r" is a balance between holes and electrons both of which form excitons and generally has a value of "1" assuming 1:1 matching of 100%. "(I)" is a value related with luminous efficiency of actual luminous materials and depends upon photoluminescence of dopant in a host-dopant system.

"$\eta_{out-coupling}$" is a ratio of light extracted outwardly among the emitted light in a luminous material. When isotropic luminous material is thermally deposited to form a thin film, each of luminous molecules does not have specific orientation, but exists with random states. The out-coupling efficiency in such random orientation is generally assumed "0.2". Accordingly, when combining 4 parameters, the OLED may exhibit at most 5% luminous efficiency in case of using the prior art fluorescent material.

In contrast, phosphorescent materials adopt different luminous mechanism of converting both singlet excitons and triplet exciton into light. The phosphorescent materials convert singlet excitons into triplet excitons through inter-system crossing (ISC). Therefore, it is possible to enhance luminous efficiency when the phosphorescent materials, which use both the singlet excitons and the triplet excitons during the luminous process, are applied as a luminous material compared to the fluorescent materials.

In case of using metal complexes having a heavy metal such as Ir, Pt, and the likes as the phosphorescent materials, it is possible to convert singlet state to triplet state through strong spin-orbital bonds by the heavy metal. However, the prior art phosphorescent materials do not have enough color purity for the display device and exhibit very short luminous life span, and therefore, they have not been used in commercial display devices.

Delayed fluorescent material has been developed for solving the problems caused by the prior art fluorescent and phosphorescent materials. Representative delayed fluorescent materials utilize thermally activated delayed fluorescence (TADF) mechanism. The delayed fluorescent material enables intramolecular charge transfer and can utilize triplet exciton energy as well as singlet exciton energy during the emission process, and therefore can enhance luminous efficiencies.

Figure 3:
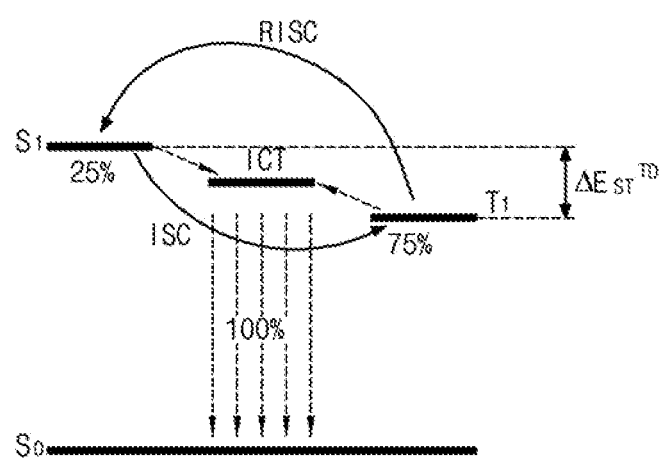
FIG. 3 is a schematic diagram illustrating luminous mechanism of the delayed fluorescent material in accordance with an exemplary embodiment of the present disclosure.

FIG. 3 is a schematic diagram illustrating luminous mechanism by a delayed fluorescent material in an EML in accordance with an exemplary embodiment of the present disclosure.

The delayed fluorescence can be divided into a thermally activated delayed fluorescence (TADF) and a filed activated delayed fluorescence (FADF). Triplet exciton in the delayed fluorescent material can be activated by heat or electrical field so that super-fluorescence beyond the maximal luminous efficiency by conventional fluorescent material can be realized.

Since the triplet excitons within the delayed fluorescent material can be activated by heat or electrical field generated in driving the OLED, the triplet excitons can be involved in emission processes. Since the delayed fluorescent material generally has an electron donor moiety as well as an electron acceptor moiety, it can be converted to an intramolecular charge transfer (ICT) state. In case of using the delayed fluorescent material, which can be converted to an ICT state, as a dopant, the excitons of singlet energy level $S_1$ as well as the excitons of triplet energy level $T_1$ can move to an intermediate energy level state, i.e. ICT state, and then the intermediate stated excitons can be transferred to a ground state ($S_0$; $S_1 \rightarrow ICT \leftarrow T_1$). Since the excitons of singlet energy level $S_1$ as well as the excitons of triplet energy level $T_1$ in the delayed fluorescent material is involved in the emission process, the delayed fluorescent material can improve internal quantum efficiency and luminous efficiency.

Since both the Highest Occupied Molecular Orbital (HOMO) and the Lowest Unoccupied Molecular Orbital (LUMO) are widely distributed over the whole molecule within the common fluorescent material, it is not possible to inter-convert between the single energy level and the triplet energy level within it (selection rule). In contrast, since the delayed fluorescent material, which can be converted to ICT state, has little orbital overlaps between HOMO and LUMO, there is little interaction between the HOMO state molecular orbital and the LUMO state molecular orbital within the delayed fluorescent material. As a result, the changes of spin states of electrons does not have an influence on other electrons, and a new charge transfer band (CT band) that does not follow the selection rule is formed in the delayed fluorescent material.

In other words, since the delayed fluorescent material has the electron acceptor moiety spacing apart from the electron donor moiety within the molecule, it exists as a polarized state having a large dipole moment within the molecule. As there is little interaction between HOMO state orbital and LUMO state orbital in the molecule having the dipole moment of the polarized state, the triplet energy level excitons as well as the singlet energy level excitons can be converted to ICT state. Accordingly, the excitons of triplet energy level $T_1$ as well as the excitons of singlet energy level $S_1$ can participate in the emission process.

In case of driving the OLED that includes the delayed fluorescent material, 25% excitons of singlet energy level $S_1$ and 75% excitons of triplet energy level $T_1$ are converted to ICT state by heat or electrical field, and then the converted excitons at ICT state transfers to the ground state $S_0$ with luminescence. Therefore, the delayed fluorescent material may have 100% internal quantum efficiency in theory.

The delayed fluorescent material must has an energy level bandgap $\Delta E_{ST}^{TD}$ equal to or less than about 0.3 eV, for example, from about 0.05 to about 0.3 eV, between the singlet energy level $S_1$ and the triplet energy level $T_1$ so that exciton energy in both the singlet energy level and the triplet energy level can be transferred to the ICT state. The material having little energy level bandgap between the singlet energy level $S_1$ and the triplet energy level $T_1$ can exhibit common fluorescence with Inter system Crossing (ISC) in which the excitons of singlet energy level $S_1$ can be transferred to the excitons of triplet energy level $T_1$, as well as delayed fluorescence with Reverser Inter System Crossing (RISC) in which the excitons of triplet energy level $T_1$ can be transferred upwardly to the excitons of single energy level $S_1$, and then the exciton of singlet energy level $S_1$ can be transferred to the ground state $S_0$.

Figure 4:
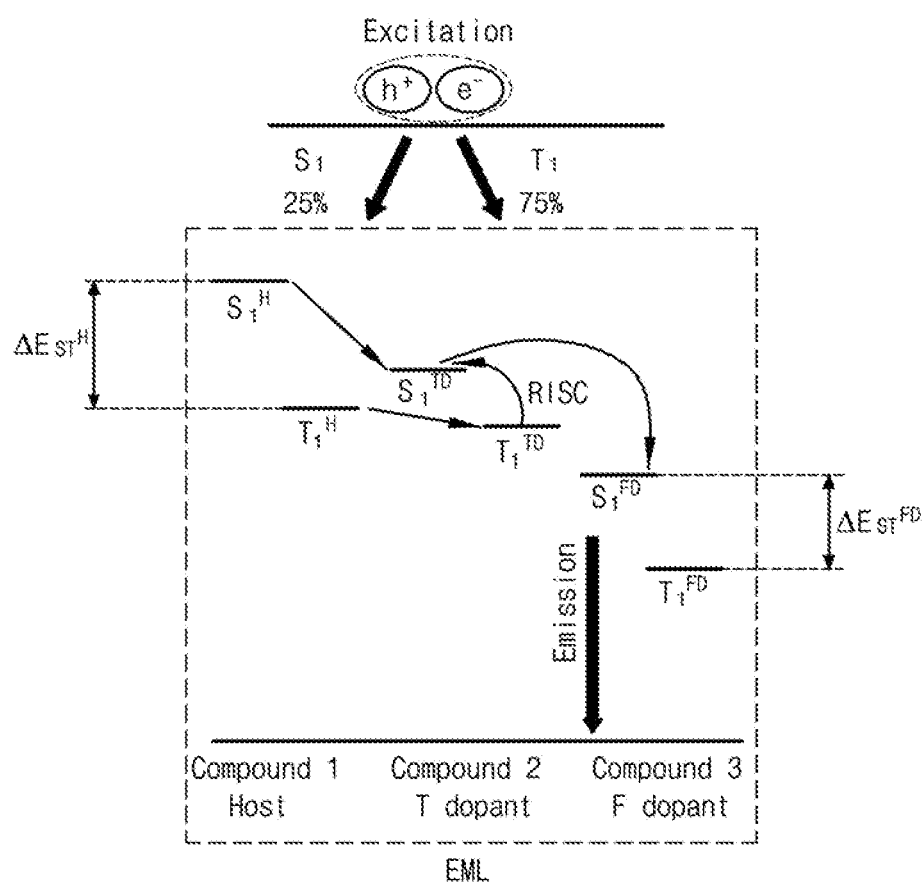
FIG. 4 is a schematic diagram illustrating luminous mechanism by energy level bandgap among luminous materials in the EML in accordance with an exemplary embodiment of the present disclosure.

FIG. 4 is a schematic diagram illustrating luminous mechanism by energy level bandgap among luminous materials in the EML in accordance with an exemplary embodiment of the present disclosure. With referring to FIG. 4, it is necessary to transfer exciton energy generated in the first compound, which may be a host, to the second compound, which may be a delayed fluorescent material, in advance. In order to realize such exciton energy transfer, each of an excited state singlet energy level $S_1^H$ and an excited state triplet energy level $T_1^H$ of the first compound, which may be the host, should be higher than each of an excited state singlet energy level $S_1^{TD}$ and an excited state triplet energy level $T_1^{TD}$ of the second compound, which may be the delayed fluorescent materials, respectively.

For example, when the excited state triplet energy level $T_1^H$ of the first compound is not sufficiently higher than the excited state triplet energy level $T_1^{TD}$ of the second compound, the excitons of the triplet state $T_1^{TD}$ of the second compound, which may be the delayed fluorescent material, can be reversely transferred to the excited state triplet energy level $T_1^H$ of the first compound, which may be the host. Accordingly, the excitons of the triplet state $T_1^{TD}$ of the second compound may be quenched as a non-emission in the first compound, which cannot use the triplet exciton energy, and therefore, the triplet exciton energy cannot contribute to the emission. For example, the excited state triplet energy level $T_1^H$ of the first compound may be high by at least about 0.2 eV compared to the excited state triplet energy level $T_1^{TD}$ of the second compound.

The second compound must have an energy level bandgap $\Delta E_{ST}^{TD}$ between the excited stated singlet energy level $S_1^{TD}$ and the excited state triplet energy level $T_1^{TD}$ equal to or less than about 0.3 eV in order to realized delayed fluorescence (See, FIG. 3). On the contrary, each of an energy level bandgap $\Delta E_{ST}^{H}$ between the excited state singlet energy level $S_1^{H}$ and the excited state triplet energy level $T_1^{H}$ of the first compound and an energy level bandgap $\Delta E_{ST}^{FD}$ between an excited state singlet energy level $S_1^{FD}$ and an excited state triplet energy level $T_1^{FD}$ of the third compound may be more than about 0.3 eV, respectively.

When each of the energy level bandgap $\Delta E_{ST}^{H}$ and $\Delta E_{ST}^{FD}$ of the first and third compounds is equal to or less than about 0.3 eV, the OLED 300 may have a reduced luminous life span owing to the RISC luminous mechanism and ISC luminous mechanism caused by those compounds. As an example, each of the energy level bandgap $\Delta E_{ST}^{H}$ of the first compound and the energy level bandgap $\Delta E_{ST}^{FD}$ of the third compound may be, but are not limited to, larger than about 0.3 eV and equal to or less than about 1.5 eV, respectively.

In addition, it is necessary to realize an OLED having high luminous efficiency and color purity as well as transferring efficiently exciton energy form the second compound as the delayed fluorescent material, in which the second compound is converted to ICT complex sate by RISC mechanism, to the third compound as the fluorescent material. In order to realized such an OLED, each of the excited state singlet energy level $S_1^{TD}$ and the excited state triplet energy level $T_1^{TD}$ of the second compound, which may be the delayed fluorescent material, may be higher than each of the excited state singlet energy level $S_1^{FD}$ and the excited state triplet energy level $T_1^{FD}$ of the third compound, which may the fluorescent material, respectively.

When the delayed fluorescent material is used in implementing luminescence, the triplet exciton can participate in the emission process. When a recombination region of forming an exciton is formed at an interface between the EML and the ETL, the possibility of meeting between the triplet exciton of the delayed fluorescent material and the hole-polaron to interact each other is increased. Due to the interaction between the triplet exciton of the delayed fluorescent material and the hole-polaron, the triplet exciton of the delayed fluorescent material fails to contribute to the emission mechanism, resulting in being quenched as a non-emission. As the non-emission quenching is increased, stresses are applied to the materials in the EML, which causes damages in the materials, and thereby reducing the life span of the OLED 300.

Figure 5:
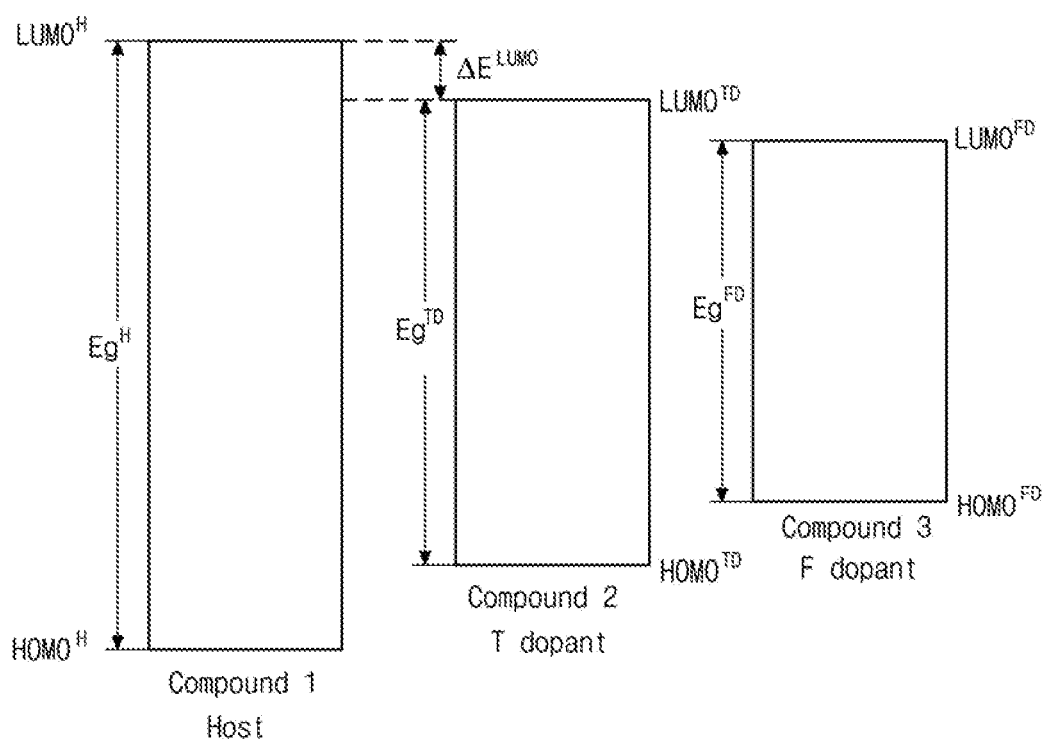
FIG. 5 is a schematic diagram illustrating HOMO energy levels and LUMO energy levels among the luminous materials in the EML in accordance with an exemplary embodiment of the present disclosure.

In addition to the singlet and triplet energy levels among the first compound, the second compound and the third compound, it is necessary to adjust properly Highest Occupied Molecular Orbital (HOMO) energy levels and Lowest Unoccupied Molecular Orbital (LUMO) energy levels among the first to third compounds. FIG. 5 is a schematic diagram illustrating HOMO energy levels and LUMO energy levels among the luminous materials in the EML 360 in accordance with an exemplary embodiment of the present disclosure.

As illustrated in FIG. 5, an energy level bandgap $\Delta E^{LUMO}$ between a LUMO energy level $LUMO^{H}$ of the first compound and a LUMO energy level $LUMO^{TD}$ of the second compound may be adjusted within predetermined ranges in accordance with an exemplary embodiment of the present disclosure. In addition, a HOMO energy level $HOMO^{H}$ of the first compound, a HOMO energy level $HOMO^{TD}$ of the second compound and a HOMO energy level $HOMO^{FD}$ of the third compound may be adjusted within predetermined ranges. As an example, the energy level bandgap $\Delta E^{LUMO}$ between the LUMO energy level $LUMO^{H}$ of the first compound and the LUMO energy level $LUMO^{TD}$ of the second compound satisfy the following relationship in Equation (1), and the HOMO energy level $HOMO^{H}$ of the first compound, the HOMO energy level $HOMO^{TD}$ of the second compound and the HOMO energy level $HOMO^{FD}$ of the third compound satisfy the following relationship in Equation (2):

$$|LUMO^{H}| - |LUMO^{TD}| \leq 0.8 \text{ eV} \qquad (1)$$

$$|HOMO^{H}| \geq |HOMO^{TD}| \geq |HOMO^{FD}| \qquad (2)$$

When the energy level bandgap $\Delta E^{LUMO}$ between the LUMO energy level $LUMO^{H}$ of the first compound and the LUMO energy level $LUMO^{TD}$ of the second compound satisfy the relationship in Equation (1), and the HOMO energy level $HOMO^{H}$ of the first compound, the HOMO energy level $HOMO^{TD}$ of the second compound and the HOMO energy level $HOMO^{FD}$ of the third compound satisfy the relationship in Equation (2), exciton energies caused by recombination between the holes and electrons, each of which is injected into the EML 300, respectively, can be transferred efficiently to the third compound in which final luminescence occurs. Accordingly, the OLED 300 can have enhanced luminous efficiency and reduced driving voltage, which results in reducing consumption power and increasing luminous life span.

In one exemplary embodiment, an energy level bandgap ($|HOMO^{H} - HOMO^{TD}|$) between the HOMO energy level ($HOMO^{H}$) of the first compound and the HOMO energy level ($HOMO^{TD}$) of the second compound, or an energy level bandgap ($|LUMO^{H} - LUMO^{TD}|$) between the LUMO energy level ($LUMO^{H}$) of the first compound and the LUMO energy level ($LUMO^{TD}$) of the second compound may be equal to or less than about 0.5 eV, for example, between about 0.1 eV to about 0.5 eV. In this case, the charges can be moved efficiently from the first compound to the second compound, and thereby enhancing an ultimate luminous efficiency in the EML 360.

In another exemplary embodiment, an energy level bandgap $Eg^{H}$ between the HOMO energy level $HOMO^{H}$ and the LUMO energy level $LUMO^{H}$ of the first compound is larger than an energy level bandgap $Eg^{TD}$ between the HOMO energy level $HOMO^{TD}$ and the LUMO energy level $LUMO^{TD}$ of the second compound. In addition, the energy level bandgap $Eg^{TD}$ between the HOMO energy level $HOMO^{TD}$ and the LUMO energy level $LUMO^{TD}$ of the second compound is larger than an energy level bandgap $Eg^{TD}$ between the HOMO energy level $HOMO^{FD}$ and the LUMO energy level $LUMO^{FD}$ of the third compound. When the HOMO and LUMO energy levels among the first to third compounds satisfy the above-described conditions, it is possible to prevent quenching of the exciton energy by the formation of excited complex, i.e. prevent excited complex, i.e. exciplex formations between the first and second compound and between the second and third compounds in the luminescent process.

As an example, the energy level bandgap $Eg^{H}$ between the HOMO energy level $HOMO^{H}$ and the LUMO energy level $LUMO^{H}$ of the first compound at absolute temperature 77K may be larger than the energy level bandgap $Eg^{TD}$ between the HOMO energy level $HOMO^{TD}$ and the LUMO energy level $LUMO^{TD}$ of the second compound at absolute temperature 77K. Besides, the energy level bandgap $Eg^{TD}$ between the HOMO energy level $HOMO^{TD}$ and the LUMO energy level $LUMO^{TD}$ of the second compound at absolute temperature 77K is larger than the energy level bandgap $Eg^{FD}$ between the HOMO energy level $HOMO^{FD}$ and the LUMO energy level $LUMO^{FD}$ of the third compound at absolute temperature 77K.

When each of the energy level bandgaps $Eg^H$, $Eg^{TD}$ and $Eg^{FD}$ between the HOMO energy levels $HOMO^H$, $HOMO^{TD}$ and $HOMO^{FD}$ and the LUMO energy levels $LUMO^H$, $LUMO^{TD}$ and $LUMO^{FD}$ of the first to third compounds in the EML 360 satisfy the above-described conditions, the exciton energy generated in the EML 360 can be transferred efficiently from the first compound to the third compound via the second compound.

As described above, the first compound as the host must have higher singlet and triplet energy levels than singlet and triplet energy levels of the second compound as the delayed fluorescent material. Also, there is a need to prevent the exciton energy generated in the second compound from being quenched as a non-emission in the first compound. In one exemplary embodiment, the first compound may include, but are not limited to, an organic compound having the following structure of Chemical Formula 1:

Chemical Formula 1

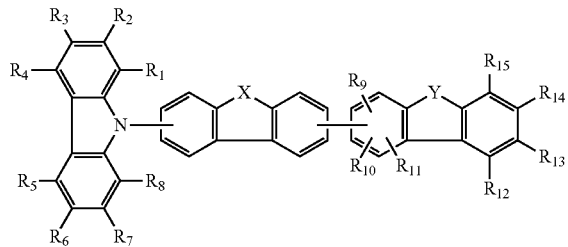

In Chemical Formula 1, each of $R_1$ to $R_{15}$ is independently hydrogen, deuterium, tritium, silyl group, $C_1$~$C_{10}$ alkyl group, $C_1$~$C_{10}$ alkoxy group, $C_1$~$C_{10}$ alkyl amino group, $C_5$-$C_{30}$ aryl group, $C_4$~$C_{30}$ hetero aryl group, $C_5$~$C_{30}$ alkyl aryl group, $C_4$~$C_{30}$ hetero alkyl aryl group, $C_5$~$C_{30}$ aryloxyl group, $C_4$~$C_{30}$ hetero aryloxyl group, $C_5$~$C_{30}$ aryl amino group or $C_4$-$C_{30}$ hetero aryl amino group, or adjacent two groups among $R_1$ to $R_{15}$ forms a fused aryl ring or a fused hetero aryl ring each of which is unsubstituted or substituted with $C_5$~$C_{30}$ aryl group or $C_4$~$C_{30}$ hetero aryl group. Each of X and Y is independently oxygen (O) or sulfur (S).

As indicated in Chemical Formula 1, the first compound includes a carbazolyl moiety (having $R_1$ to $R_8$ groups), and at least two dibenzofuranyl and/or dibenzothiophenyl moieties (having X and Y groups). Hereinafter, the central dibenzofuranyl/dibenzothiophenyl moiety linked to the carbazolyl moiety will be refereed as "a first dibenzofuranyl/dibenzothiophenyl moiety" and the side dibenzofuranyl/dibenzothiophenyl moiety linked to the first dibenzofuranyl/dibenzothiophenyl moiety will be referred as "a second dibenzofuranyl/dibenzothiophenyl moiety".

Since the carbazolyl moiety has a p-type property due to its excellent bonding ability with holes, and the first and second dibenzofuranyl/dibenzothiophenyl moieties have an n-type property due to their relatively better bonding abilities with electrons. Therefore, the organic compound having the structure of Chemical Formula 1 may have a bi-polar property.

In one exemplary embodiment, each of $R_1$ to $R_{15}$ in Chemical Formula 1 may be independently hydrogen, deuterium or tritium, respectively. In another exemplary embodiment, each of $R_1$ to $R_{15}$ in Chemical Formula 1 may be independently linear or branched $C_1$~$C_{20}$ alkyl group, preferably $C_1$~$C_{10}$ alkyl group or $C_1$~$C_{20}$ alkoxy group, preferably $C_1$~$C_{10}$ alkoxy group, respectively.

In still another exemplary embodiment, each of $R_1$ to $R_{15}$ in Chemical Formula 1 may be independently aromatic or hetero aromatic group, respectively. As an example, when each of $R_1$ to $R_{15}$ is $C_5$~$C_{30}$ aryl group, each of $R_1$ to $R_{15}$ may independently be, but are not limited to, unfused or fused aryl group such as phenyl, biphenyl, terphenyl, naphthyl, anthracenyl, pentalenyl, indenyl, indeno-indenyl, heptaleneyl, biphenylenyl, indacenyl, phenalenyl, phenanthrenyl, benzo-phenanthrenyl, dibenzo-phenanthrenyl, azulenyl, pyreneyl, fluoranthenyl, triphenylenyl, chrysenyl, tetraphenyl, tetracenyl, pleiadenyl, picenyl, pentaphenyl, pentacenyl, fluorenyl, indeno-fluorenyl or spiro-fluorenyl.

In an alternative embodiment, when each of $R_1$ to $R_{15}$ is $C_4$~$C_{30}$ hetero aryl group, each of $R_1$ to $R_{15}$ may independently be, but are not limited to, unfused or fused hetero aryl group such as pyrrolyl, pyridinyl, pyrimidinyl, pyrazinyl, pyridazinyl, triazinyl, tetrazinyl, imidazolyl, pyrazolyl, indolyl, iso-indolyl, indazolyl, indolizinyl, pyrrolizinyl, carbazolyl, bezno-carbazolyl, dibenzo-carbazolyl, indolo-carbazolyl, indeno-carbazolyl, benzofuro-carbazolyl, benzothieno-carbazolyl, quinolinyl, iso-quinolinyl, phthalazinyl, quinoxalinyl, cinnolinyl, quinazolinyl, quinozolinyl, quinolizinyl, benzo-quinazolinyl, benzo-quinoxalinyl, acridinyl, phenanthrolinyl, perimidinyl, phenanthridinyl, pteridinyl, cinnolinyl, naphththyridinyl, furanyl, pyranyl, oxazinyl, oxazolyl, oxadiazolyl, triazolyl, dioxinyl, benzo-furnaly, dibenzo-furanyl, thiopyranyl, xanthenyl, chromenyl, isochromenyl, thioazinyl, thiophenyl, benzo-thiophenyl, dibenzo-thiophenyl, difuro-pyrazinyl, benzofuro-dibenzo-furanyl, benzothieno-benzo-thiophenyl, benzothieno-dibenzo-furanyl, benzothieno-benzo-furanyl, benzothieno-dibenzo-furanyl or N-substituted spiro-fluorenyl.

In one exemplary embodiment, when each of $R_1$ to $R_{15}$ is aryl or hetero aryl group, the aryl or hetero aryl group may consist of 1 to 3 aromatic or hetero aromatic rings. When the number of the aromatic or hetero aromatic rings constituting each of $R_1$ to $R_{15}$ is increased, the conjugated structure in the entire organic compound becomes excessively long, so that the bandgap of the organic compound may be excessively reduced. As an example, when each of $R_1$ to $R_{15}$ is aromatic or hetero aromatic group, each of $R_1$ to $R_{15}$ may independently be, but are not limited to, phenyl, biphenyl, pyrrolyl, triazinyl, imidazolyl, pyrazolyl, pyridinyl, pyrazinyl, pyrimidinyl, pyridazinyl, furanyl, benzo-furanyl, dibenzo-furanyl, thiophenyl, benzo-thiophenyl, dibenzo-thiophenyl or carbazolyl, respectively.

In another exemplary embodiment, adjacent two groups among $R_1$ to $R_{15}$ may form fused aromatic or hetero aromatic ring unsubstituted or substituted with at least one of $C_5$~$C_{30}$ aryl group and $C_4$~$C_{30}$ hetero aryl group. When adjacent two groups among $R_1$ to $R_{15}$ forms the fused aromatic or hetero aromatic ring, the $C_5$~$C_{30}$ aryl group and $C_4$-$C_{30}$ hetero aryl group, each of which may be substituted to the aromatic or hetero aromatic ring, may consist of 1 or 2 aromatic or hetero aromatic rings. In this case, the organic compound having the structure of Chemical Formula 1 may have an energy level bandgap suitable for use in the EML 360. As an example, when adjacent two groups among $R_1$ to $R_{15}$ forms fused aromatic or hetero aromatic ring, the aromatic or hetero aromatic group, which may be substituted to the fused aromatic or hetero aromatic ring, may be, but are not limited to, phenyl, biphenyl, pyrrolyl, imidazolyl, pyrazolyl, pyridinyl, pyrazinyl, pyrimidinyl, pyridazinyl, furanyl or thiophenyl, preferably phenyl.

As an example, when adjacent two groups among $R_1$ to $R_{15}$ constituting the carbazolyl moiety forms fused aromatic or hetero aromatic ring, the carbazolyl moiety may form, but are not limited to, a benzo-carbazolyl moiety, a dibenzo-carbazolyl moiety, a benzofuro-carbazolyl moiety, a benzothieno-carbazolyl moiety, an indeno-carbazolyl moiety, an indolo-carbazolyl moiety and the likes, each of which is unsubstituted or substituted with linear or branched $C_1$-$C_{20}$ alkyl group, preferably linear or branched $C_1$~$C_{10}$ alkyl group, $C_5$~$C_{30}$ aryl group, preferably $C_5$~$C_{20}$ aryl group (e.g. phenyl and/or naphthyl), $C_4$~$C_{30}$ hetero aryl group, preferably $C_4$~$C_{20}$ hetero aryl group (e.g. pyridyl, pyrimidyl and/or carbazolyl) and combination thereof, respectively.

In another embodiment, when the adjacent two groups among $R_9$ to $R_{15}$ constituting the second dibenzofuranyl/dibenzothiophenyl moiety form fused aromatic or hetero aromatic ring, the second dibenzofuranyl/dibenzothiophenyl moiety may form, but are not limited to, a pyrido-dibenzofuranyl moiety, a pyrido-dibenzothiophenyl moiety, an indeno-dibenzofuranyl moiety, an indeno-dibenzothiophenyl moiety, an indolo-dibenzofuranyl moiety, an indolo-dibenzothiophenyl moiety and the likes, each of which is unsubstituted or substituted with linear or branched $C_1$-$C_{20}$ alkyl group, preferably linear or branched $C_1$~$C_{10}$ alkyl group, $C_5$-$C_{30}$ aryl group, preferably $C_5$~$C_{20}$ aryl group (e.g. phenyl and/or naphthyl), $C_4$~$C_{30}$ hetero aryl group, preferably $C_4$~$C_{20}$ hetero aryl group (e.g. pyridyl, pyrimidyl and/or carbazolyl) and combination thereof, respectively.

Since the first compound having the structures of Chemical Formula 1 includes the carbazolyl moiety having p-type properties as well as dibenzofuranyl/dibenzothiophenyl moieties having n-type properties, the first compound has excellent affinity to the holes as well as the electrons. Accordingly, when the first compound having the structure of Chemical 1 is applied to the EML 360 of the OLED 300, a recombination zone where holes and electrons form an exciton is formed in the middle of the EML 360, not in the interface between the EML 360 and the ETL 370.

In addition, the first compound having the structure of Chemical Formula 1 includes the carbazolyl moiety and dibenzofuranyl/dibenzothiophenyl moieties, each of which has a central 5-membered ring connected to both sides of 6-membered rings. Since the carbazolyl moiety as well as the dibenzofuranyl/dibenzothiophenyl has a rigid conformational structure, the first compound having the structure of Chemical Formula 1 may be excellent in heat resistance properties. Accordingly, the first compound having the structure of Chemical Formula 1 is not deteriorated by Joule's heat generated in driving the OLED 300. Therefore, the first compound having the structure of Chemical Formula 1 can be applied to the OLED 300, and thereby realizing excellent luminous efficiency and improving luminous life span of the OLED 300.

Moreover, the first compound having the structure of Chemical Formula 1 multiple dibenzofuranyl/dibenzothiophenyl moieties, each of which has a central 5-membered ring connected to both sides of 6-membered rings. Accordingly, the first compound having the structured of Chemical Formula 1 may have a HOMO energy level and a LUMO energy level suitable for use as luminous material, for example, as a host in the EML 360. In particular, when the first compound is used together with a delayed fluorescent material in the EML 360, the driving voltage of the OLED 360 may be lowered to reduce the power consumption. Accordingly, the stress applied to the OLED 300 owing to the increase in driving voltage is reduced, thereby improving luminous efficiency and the luminous life span of the OLED 300.

In one exemplary embodiment, the first compound may include, but is not limited to, an organic compound having the following structure of Chemical Formula 2 or Chemical Formula 3:

Chemical Formula 2

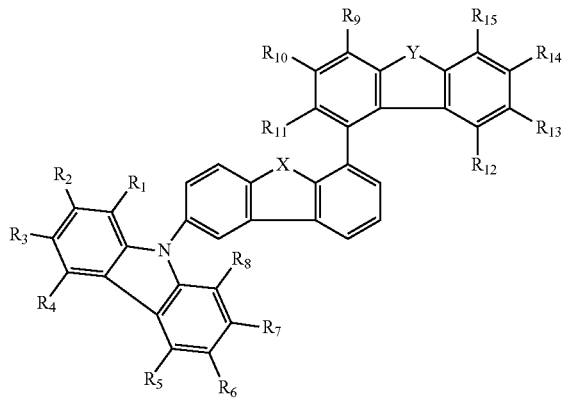

Chemical Formula 3

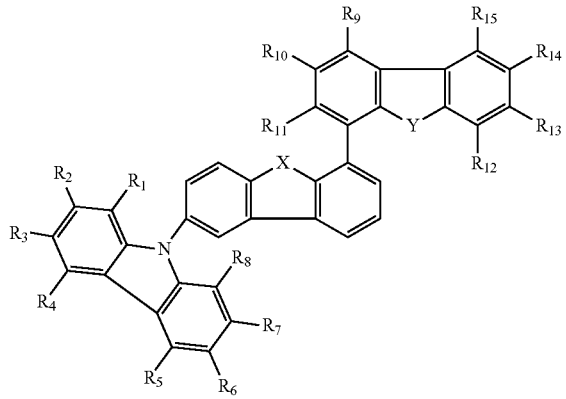

In Chemical Formulae 2 and 3, each of $R_1$ to $R_{15}$ and X and Y is identical as defined in Chemical Formula 1, respectively.

Particularly, the first compound may include, but is not limited to, any one of an organic compound having the following structures of Chemical Formula 4:

Chemical Formula 4

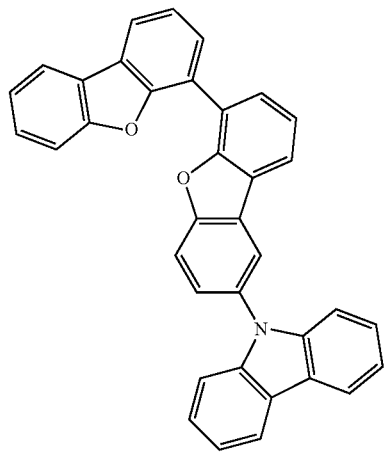

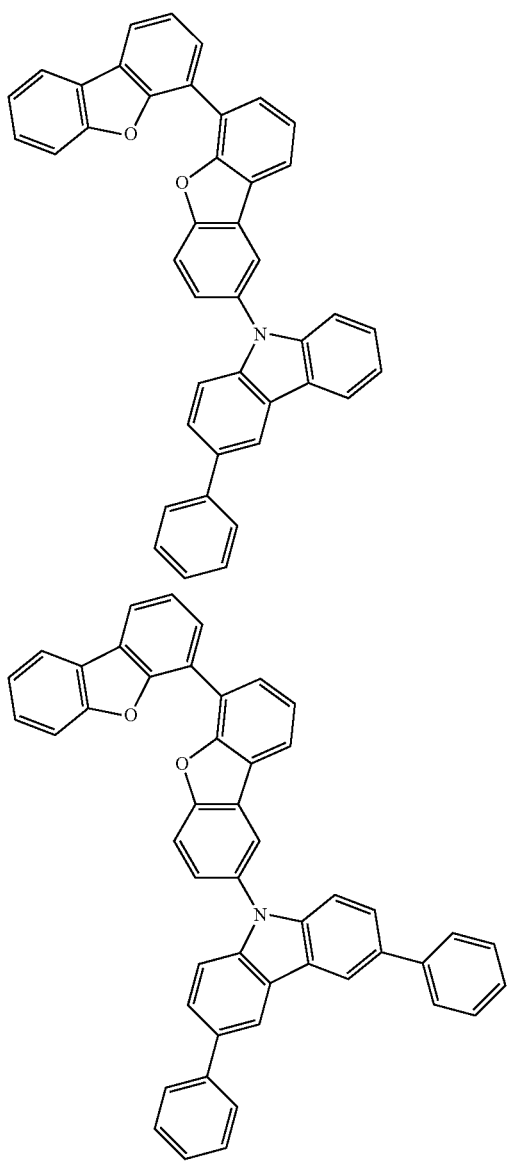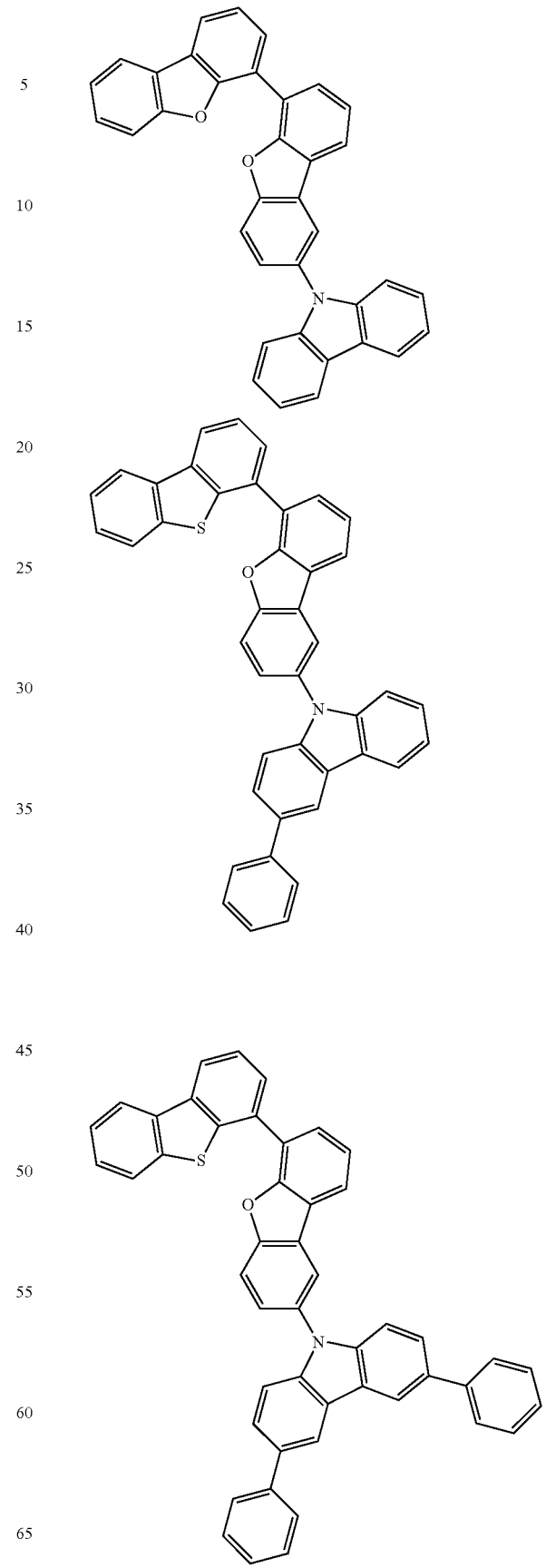

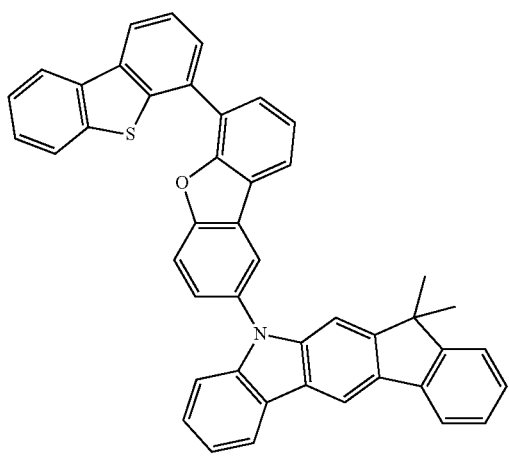
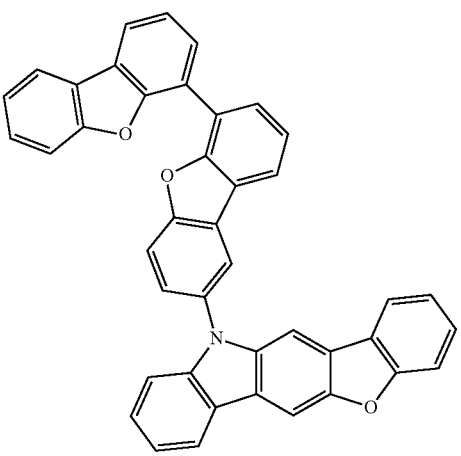
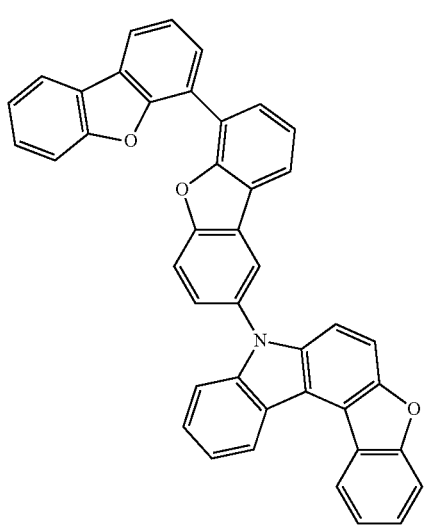
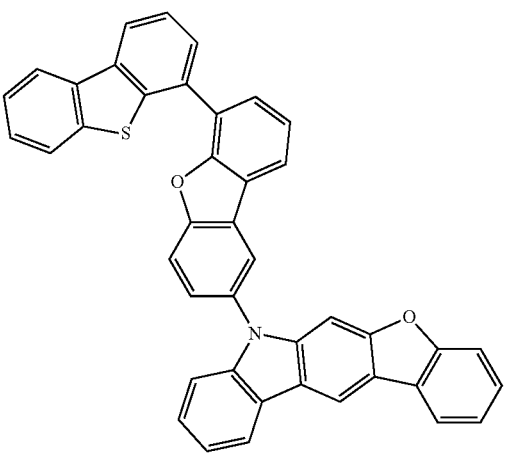

21
-continued
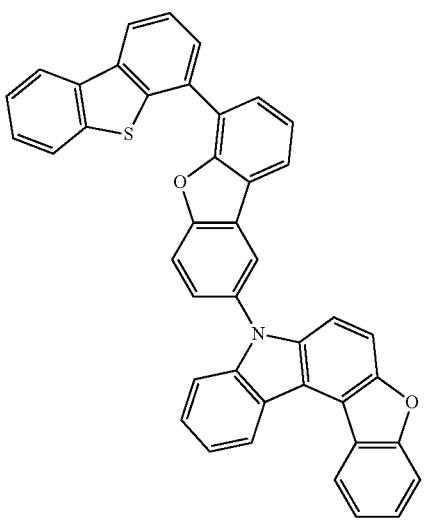
22
-continued
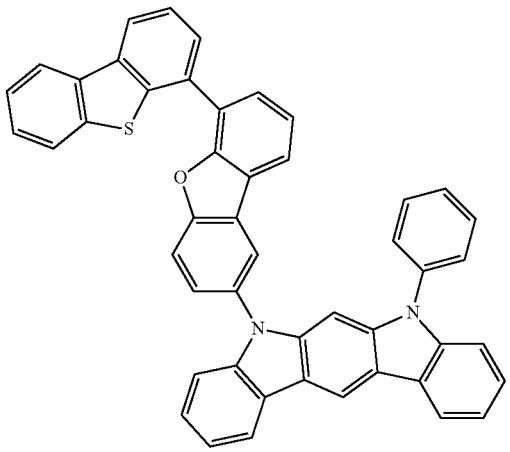
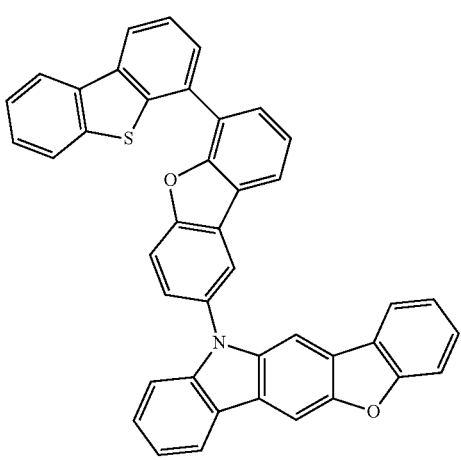
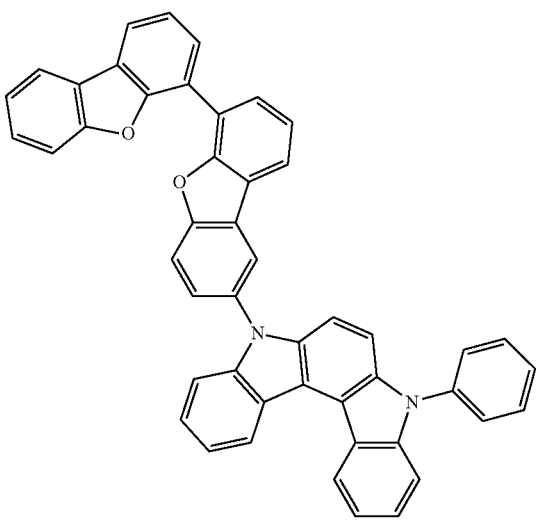
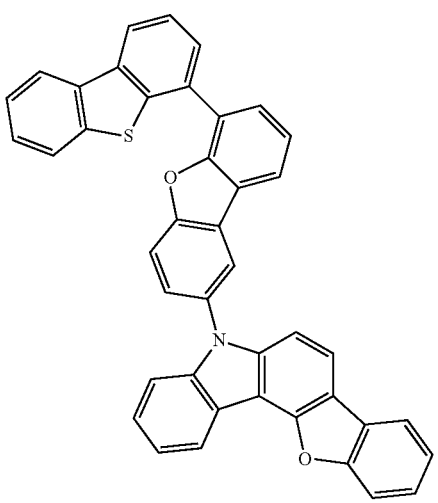
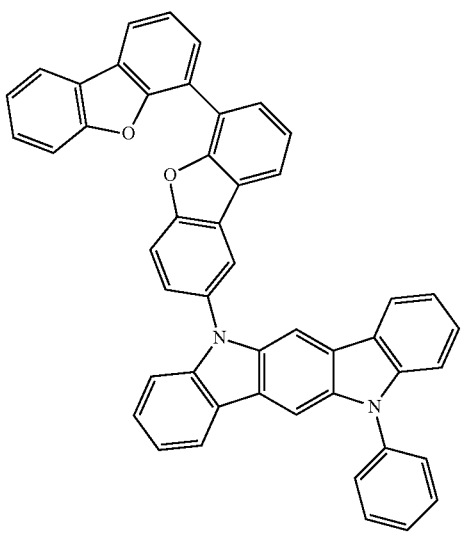

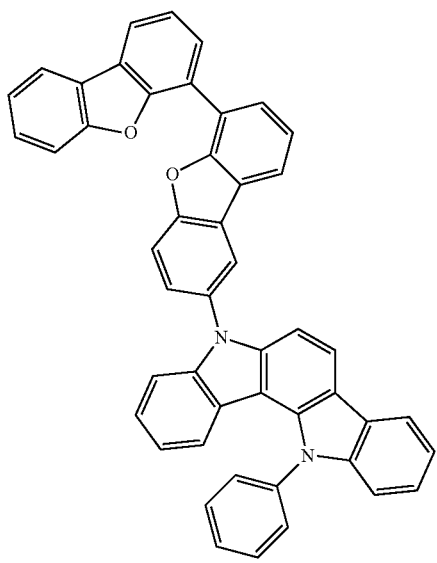
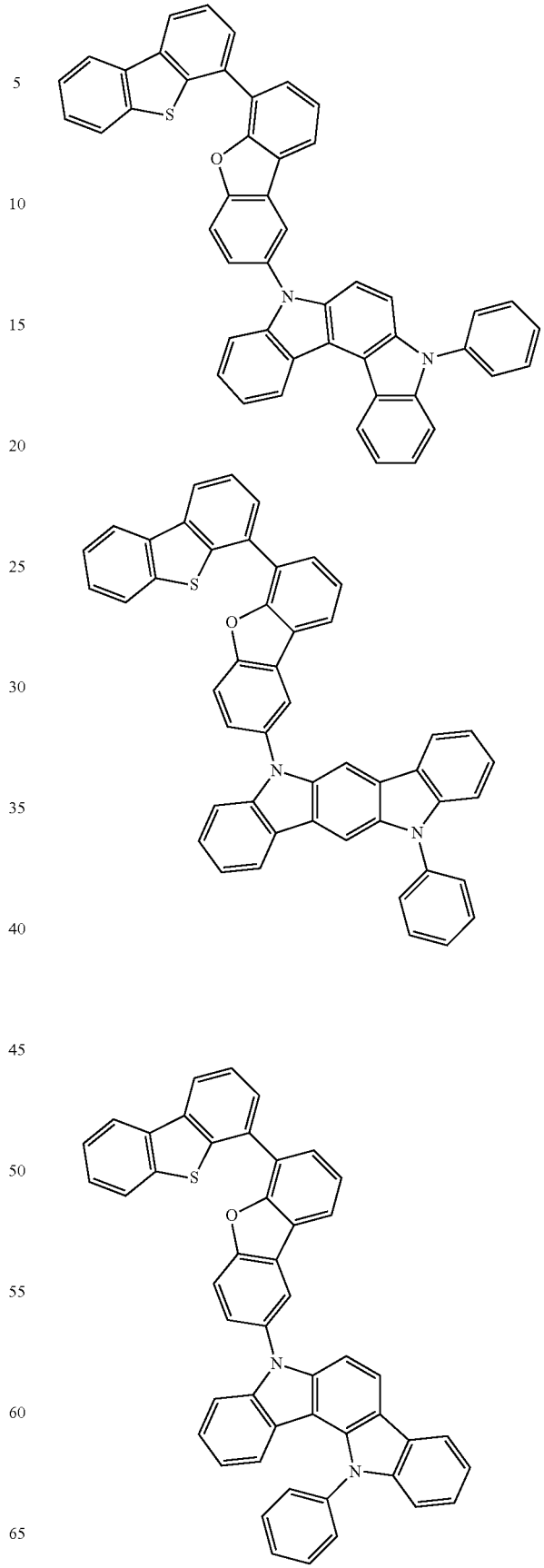

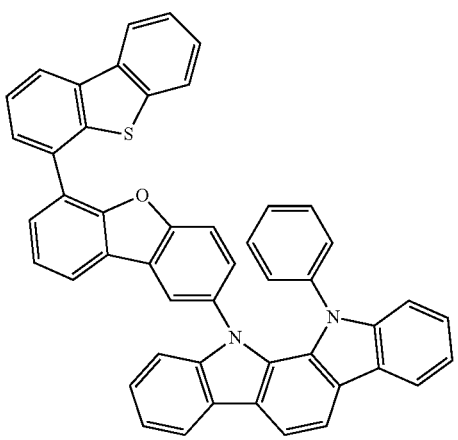
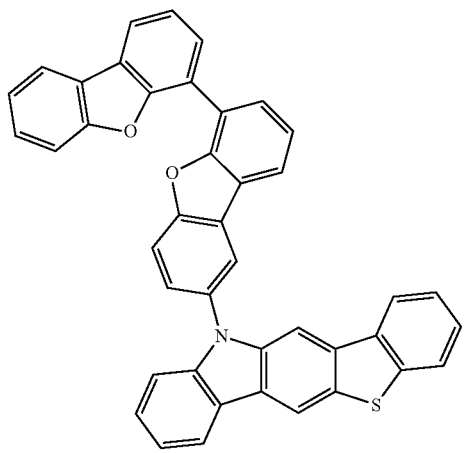
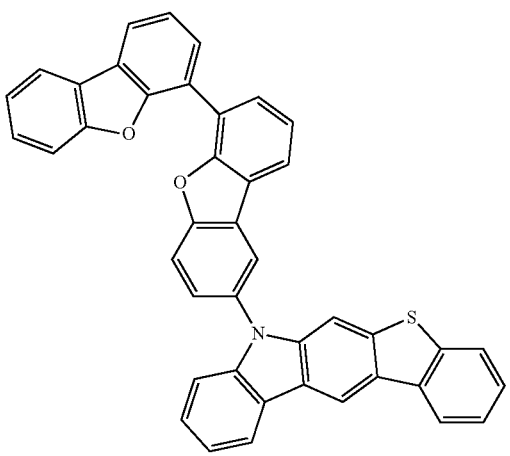
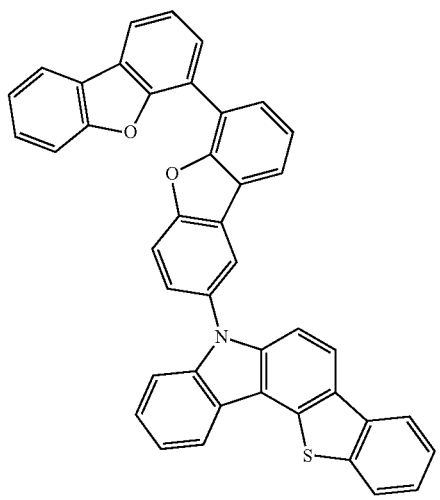
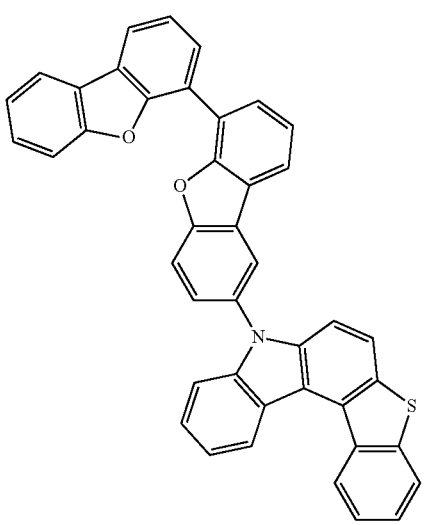
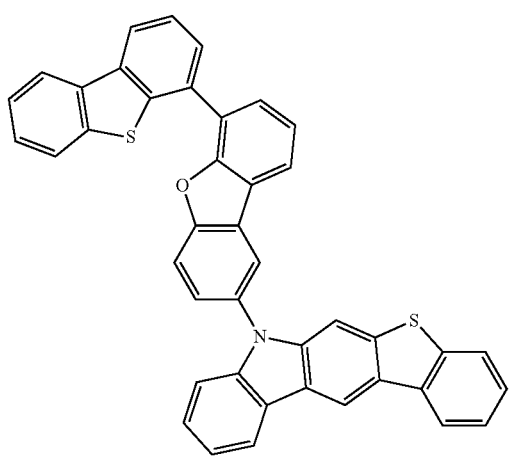

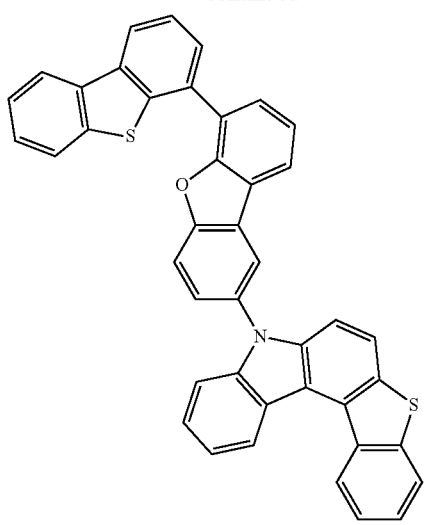
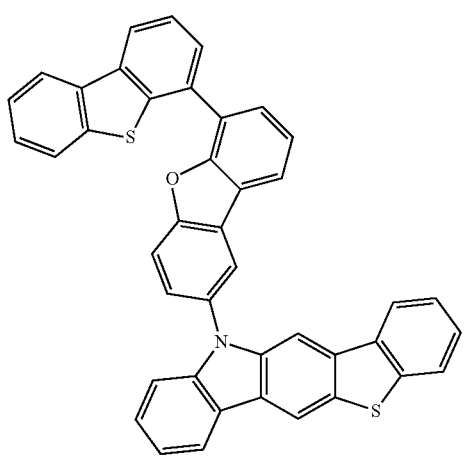
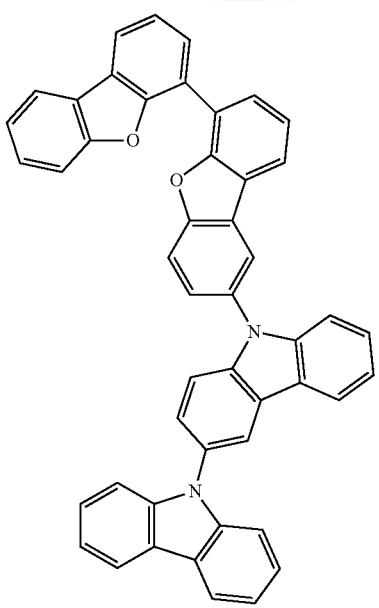
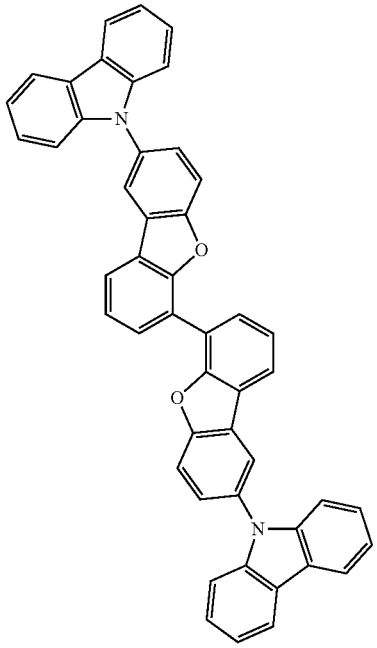

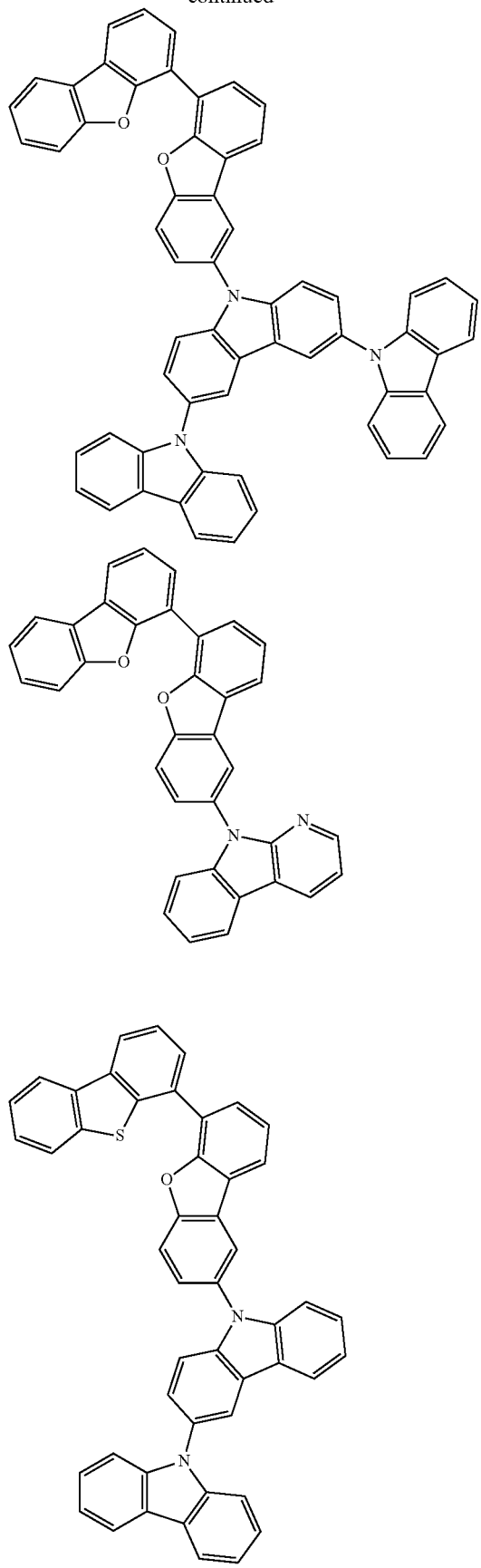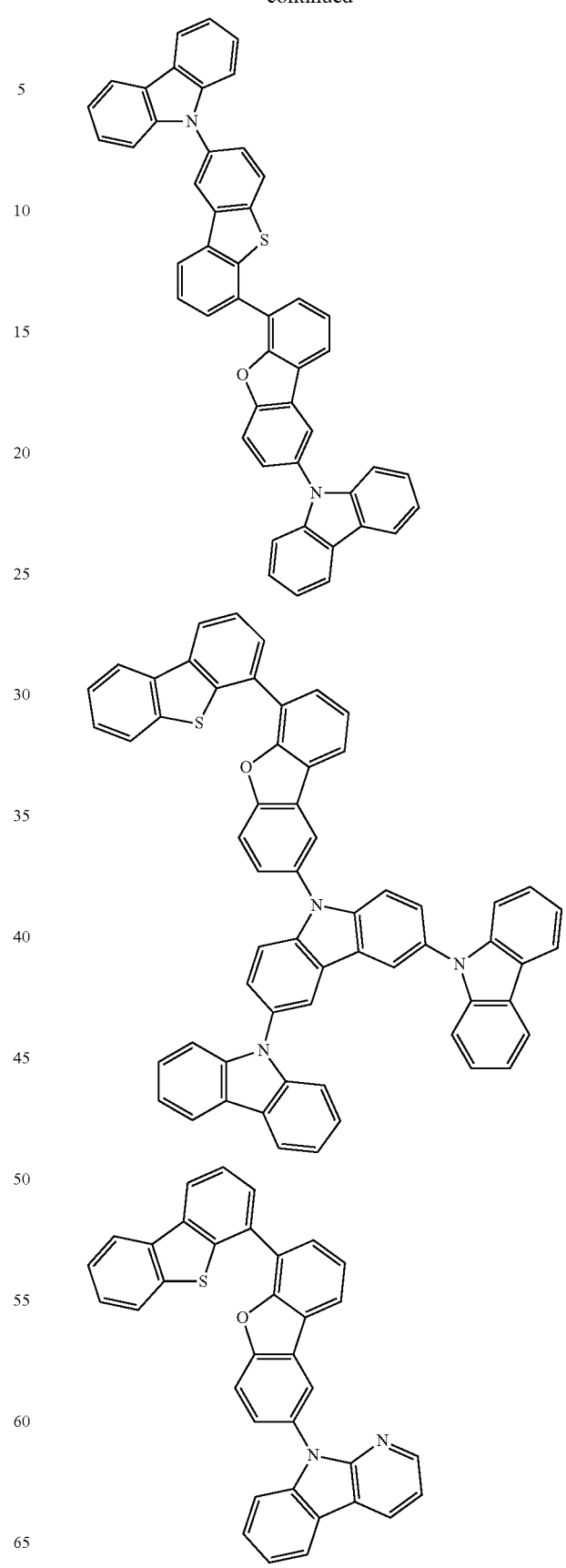

31
-continued
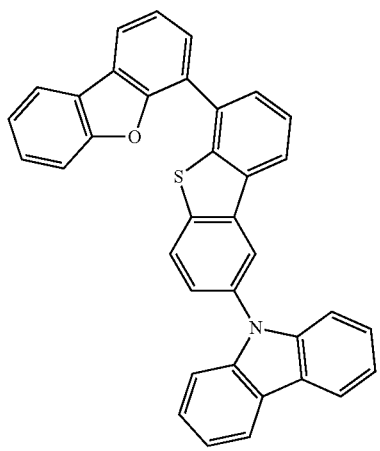
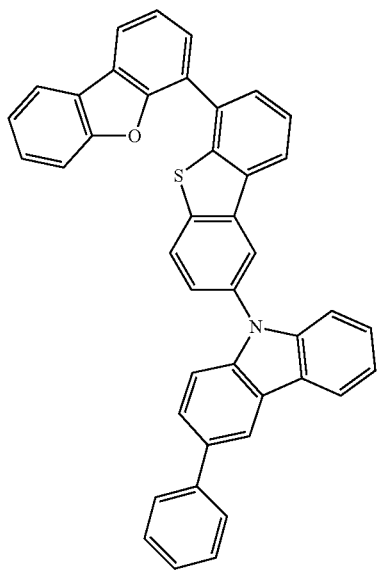
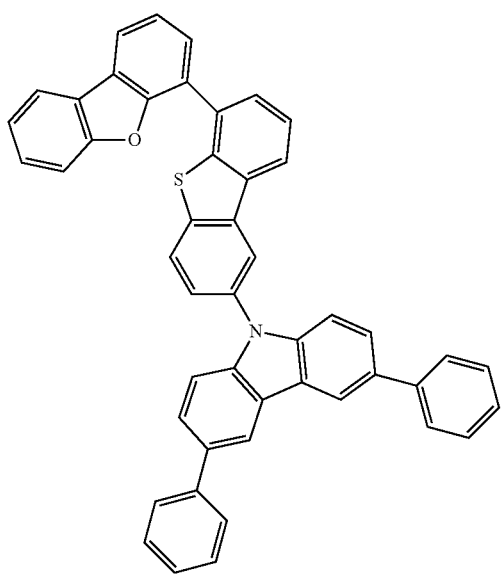
32
-continued
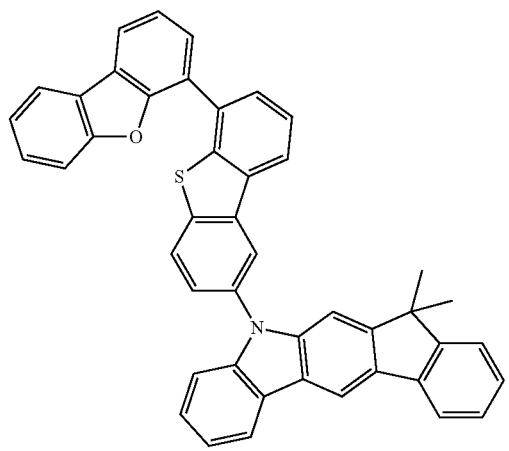
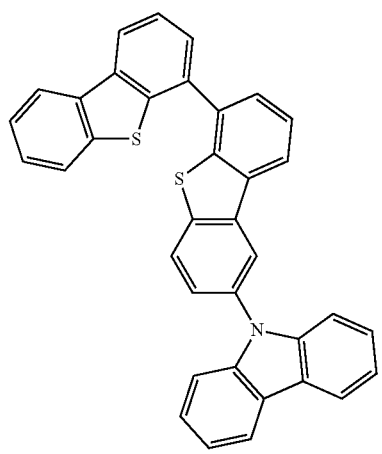
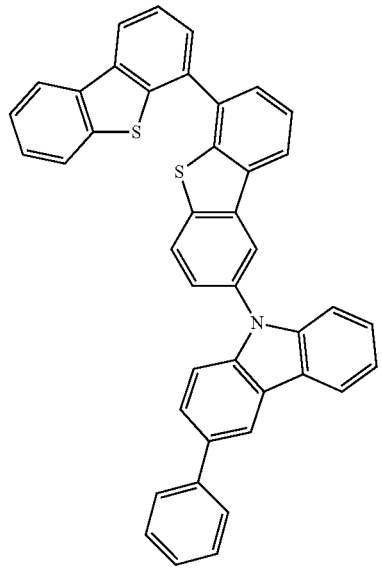

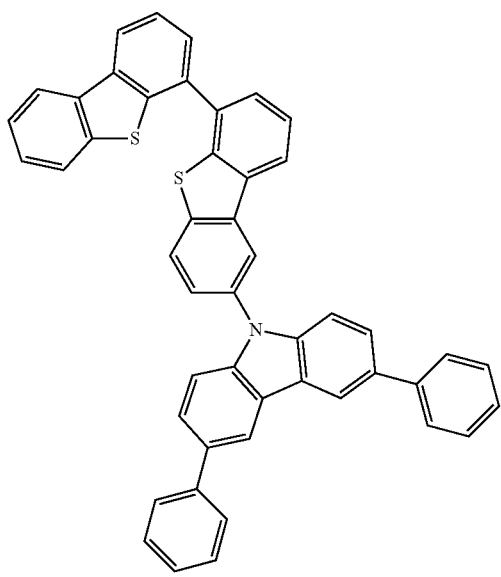
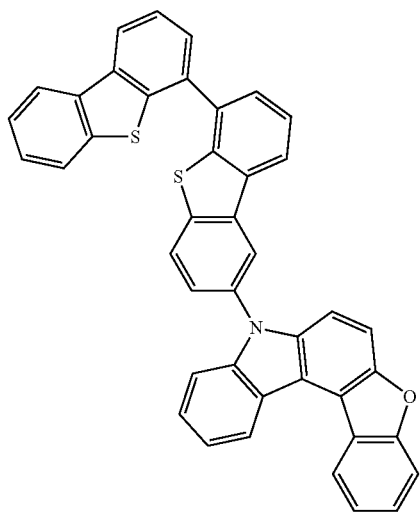
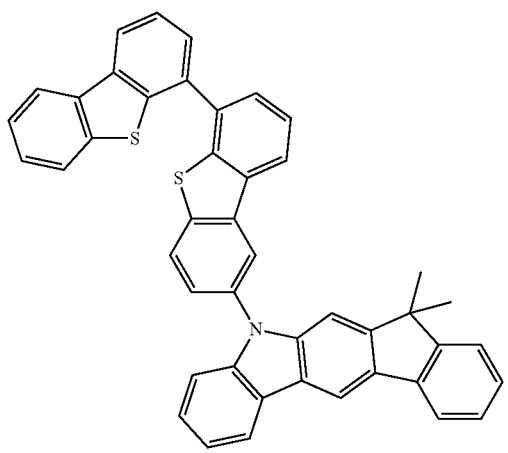
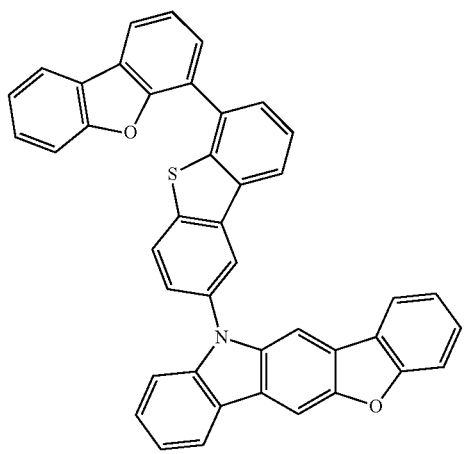
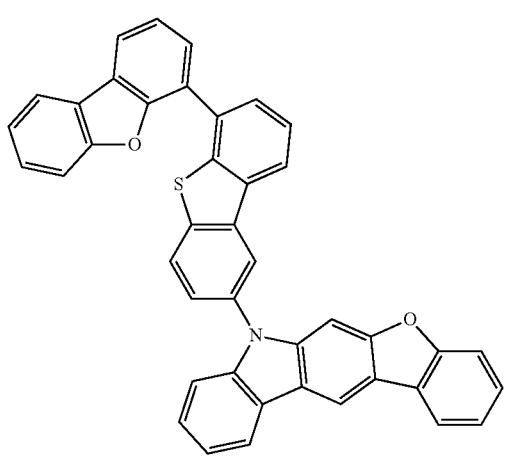
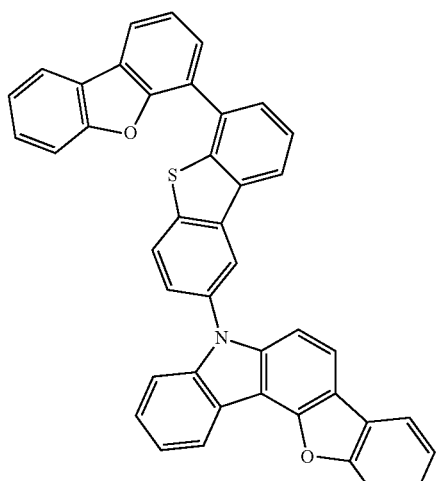

35
-continued
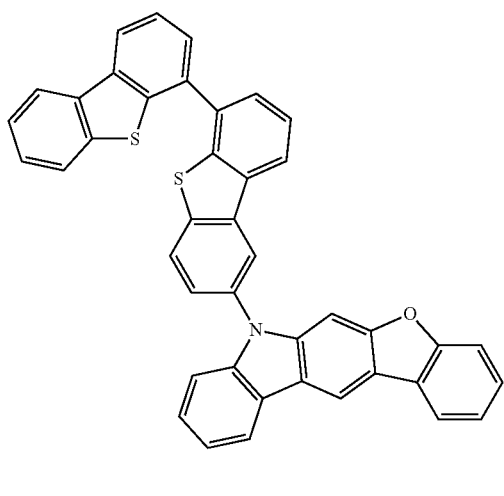
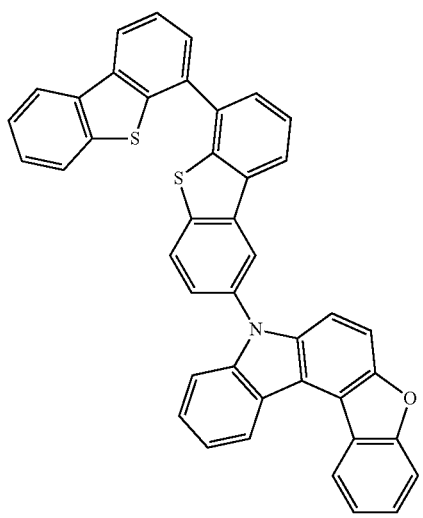
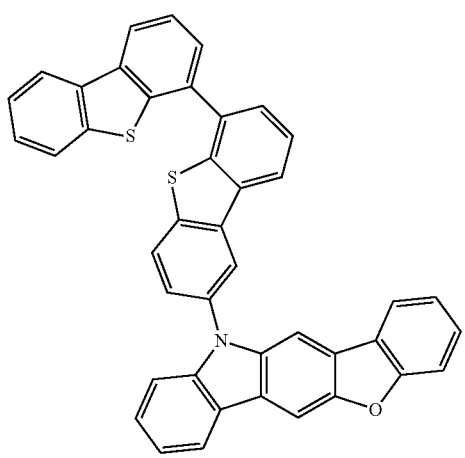
36
-continued
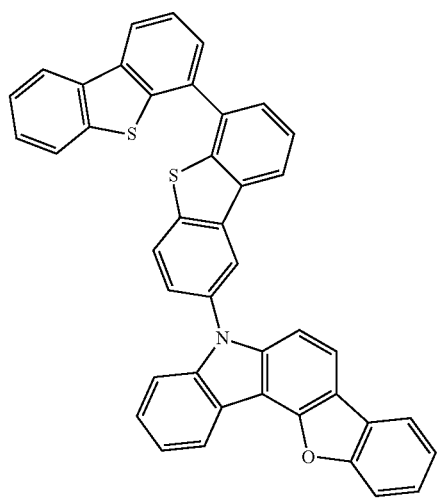
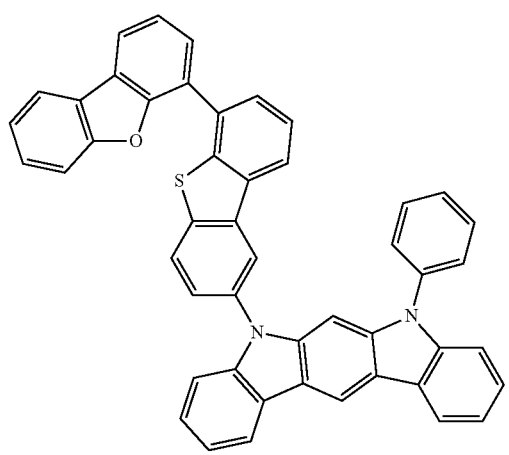
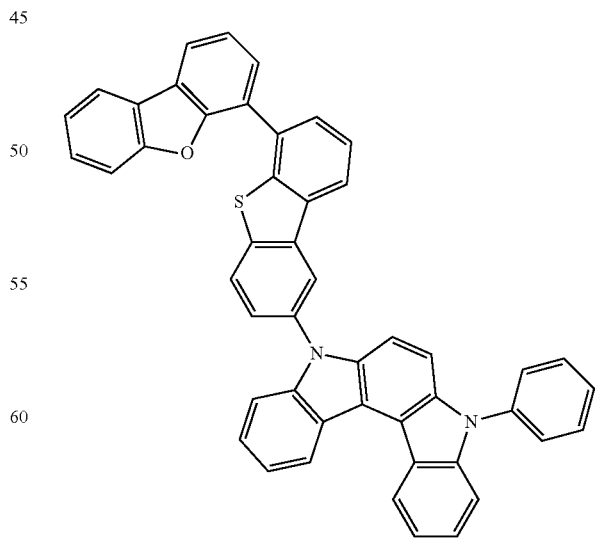

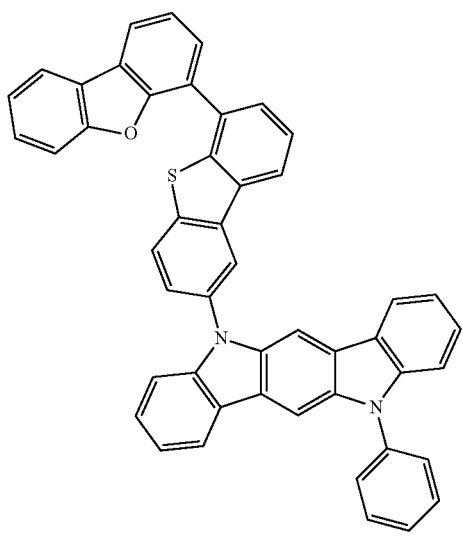
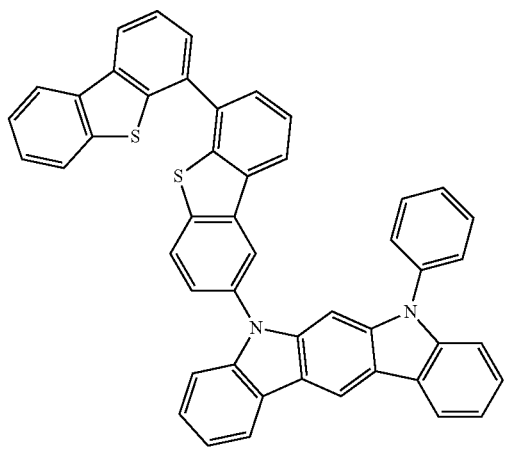
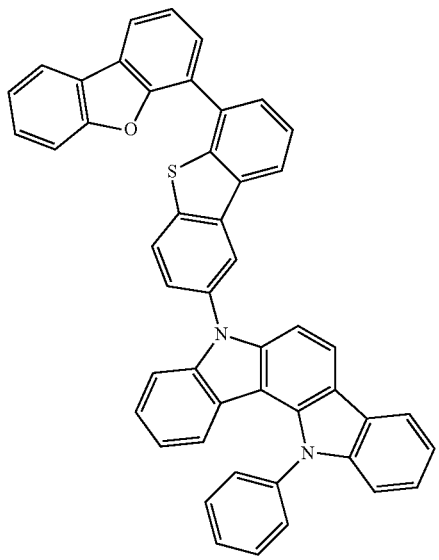
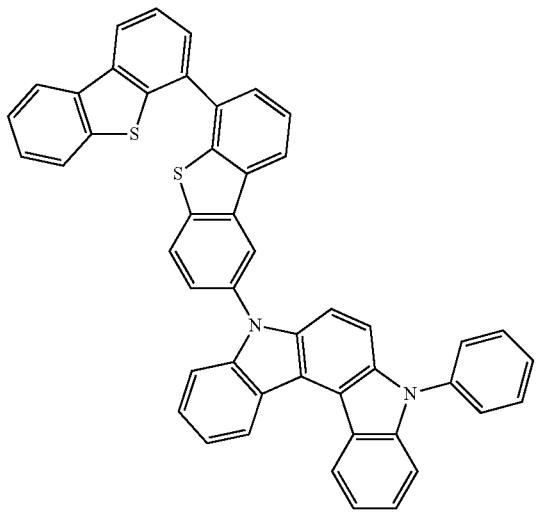
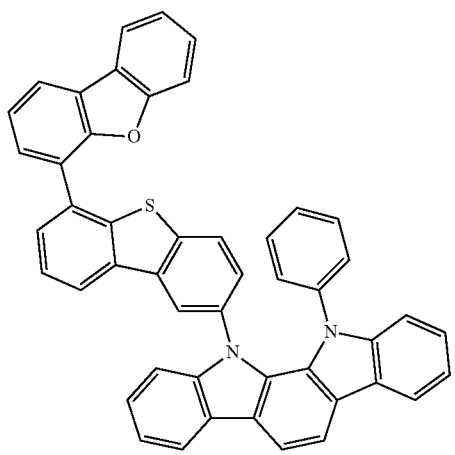
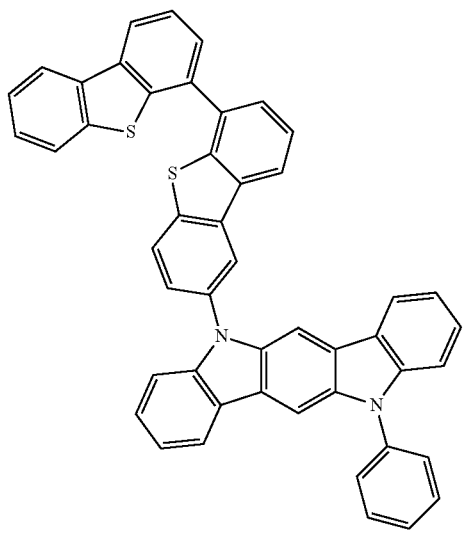

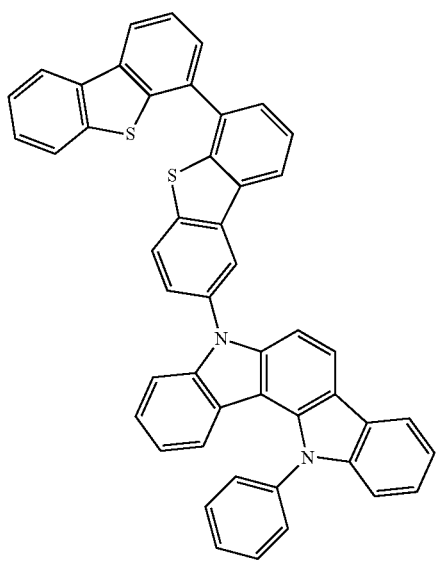
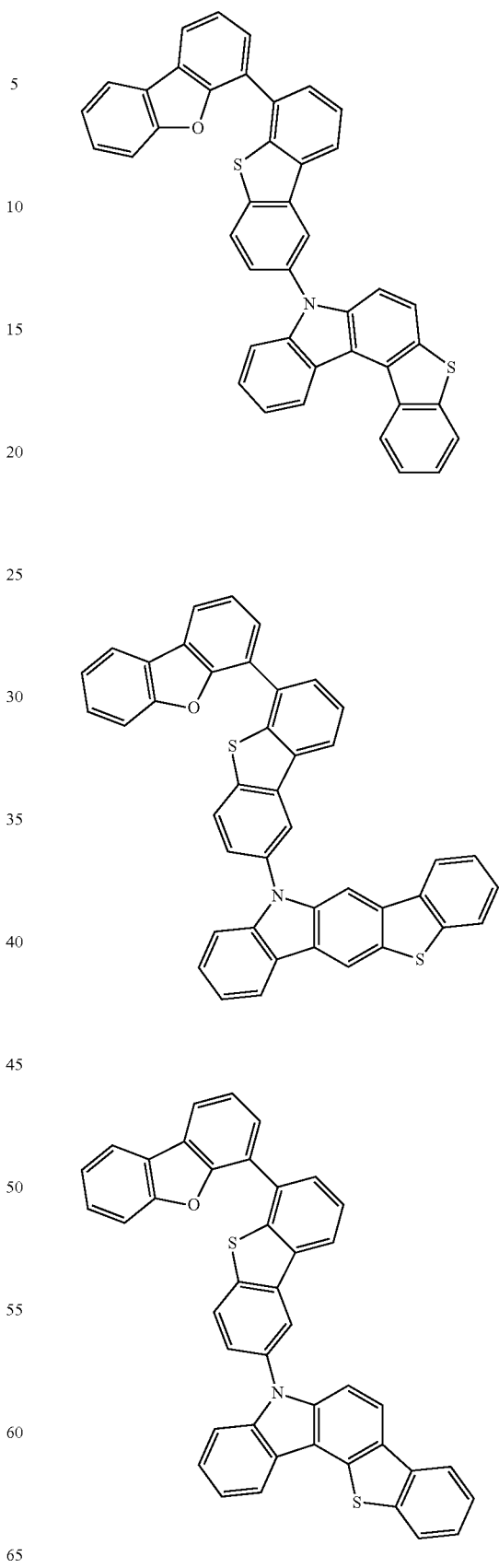

41
-continued
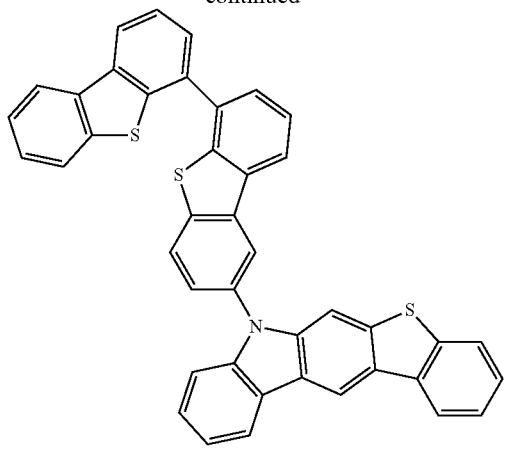
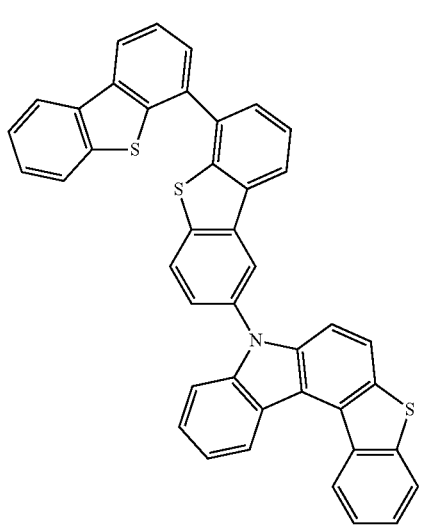
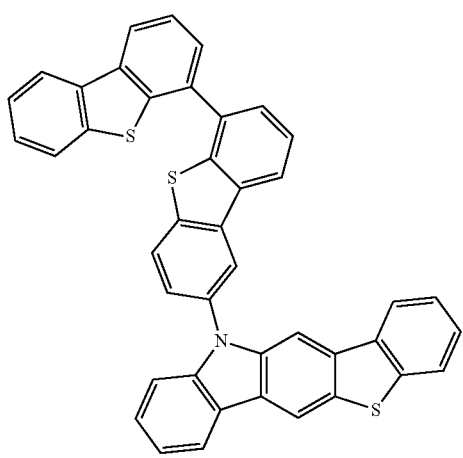
42
-continued
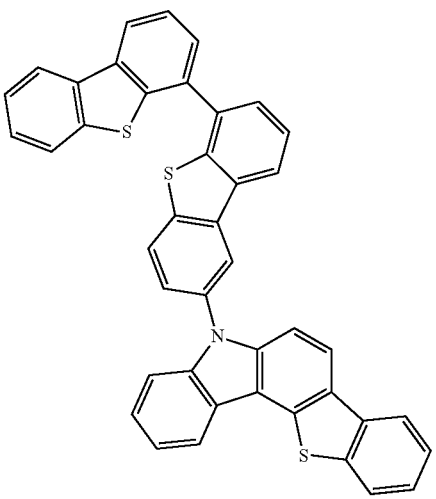
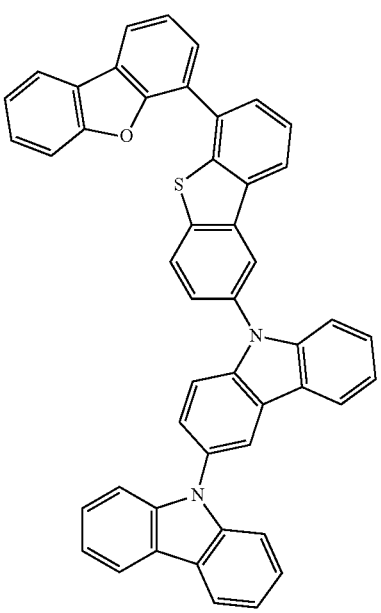

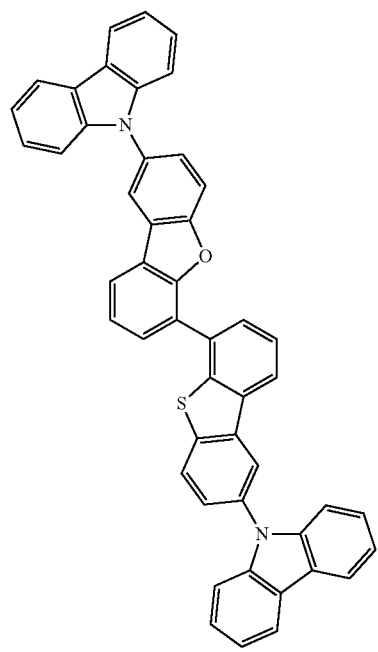
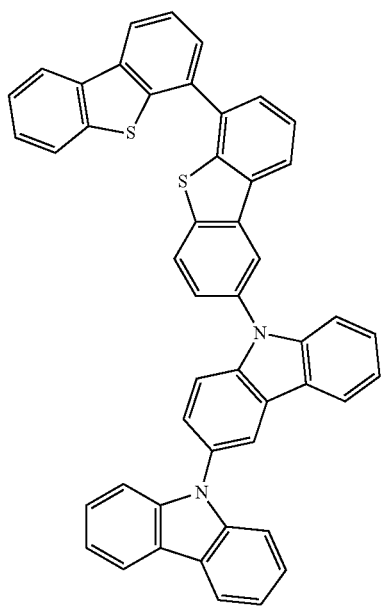
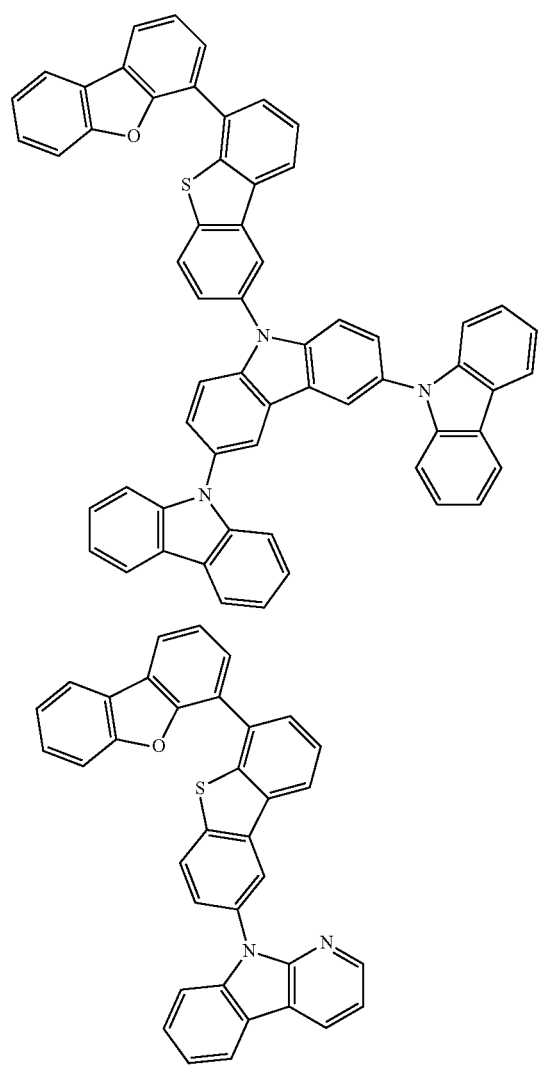
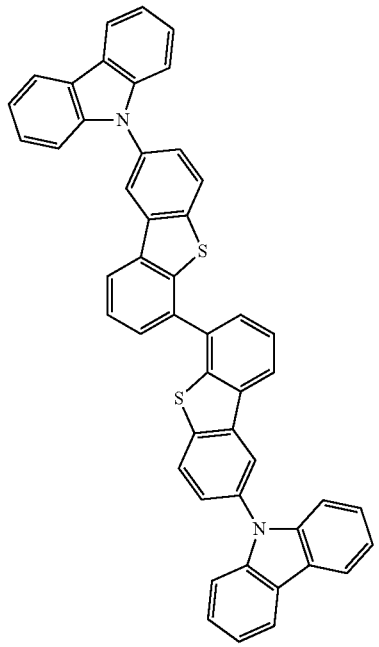

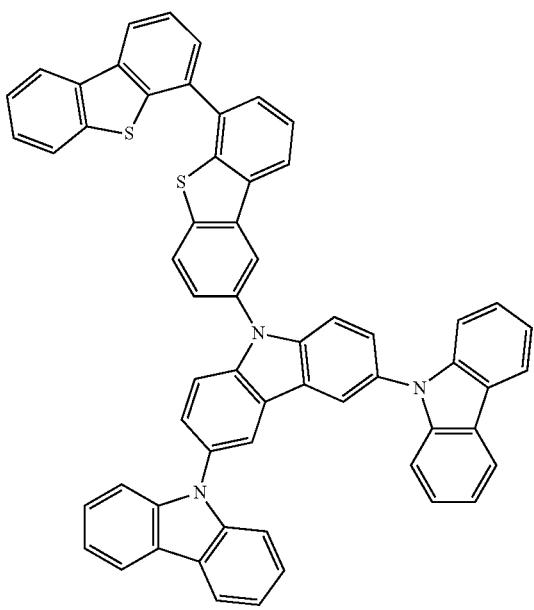
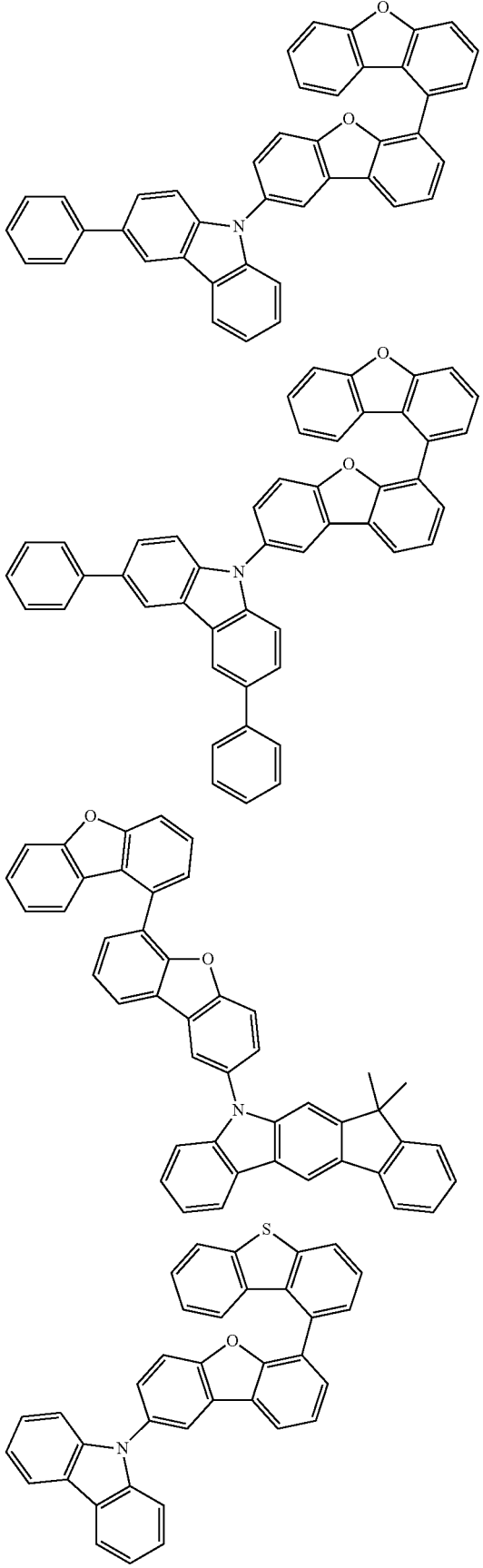

47
-continued
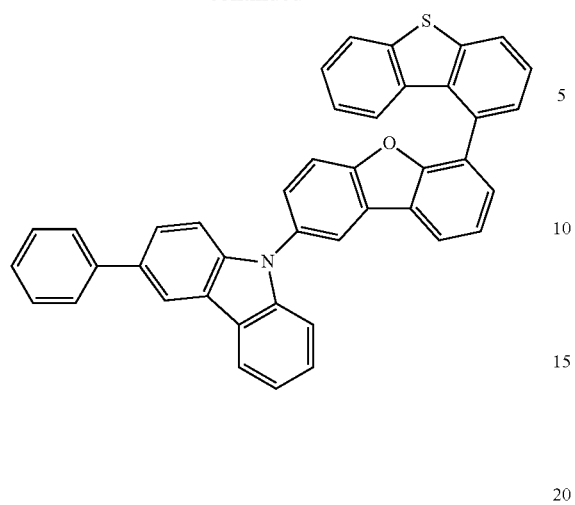
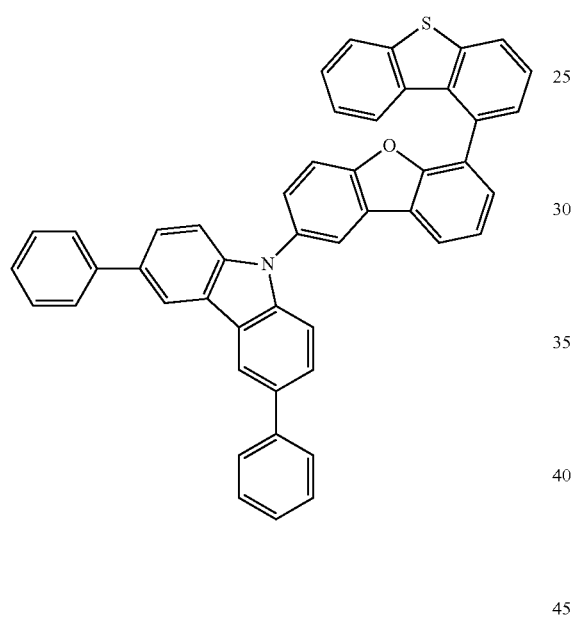
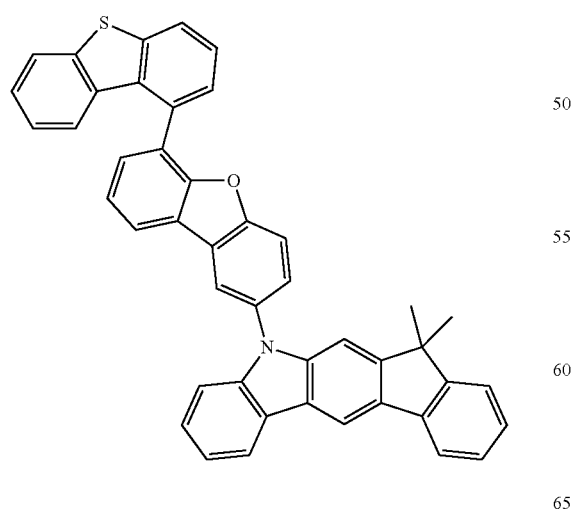
48
-continued
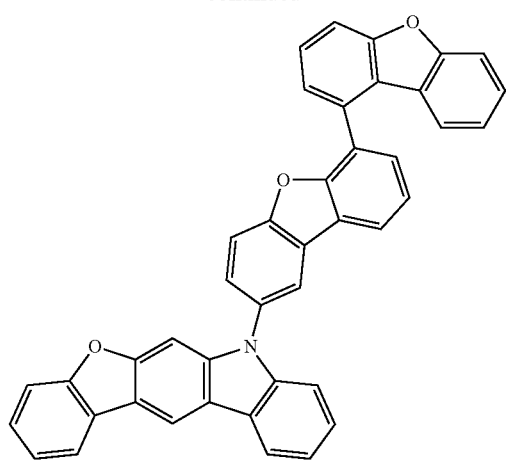
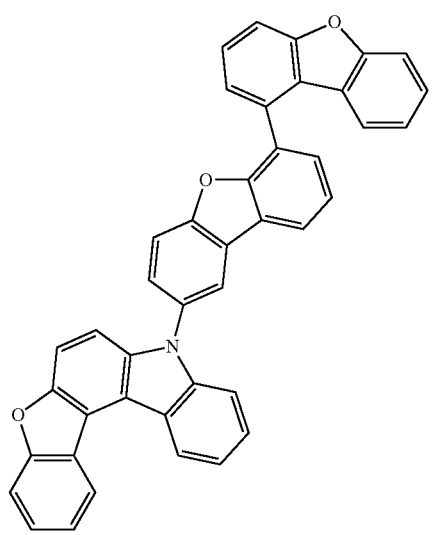
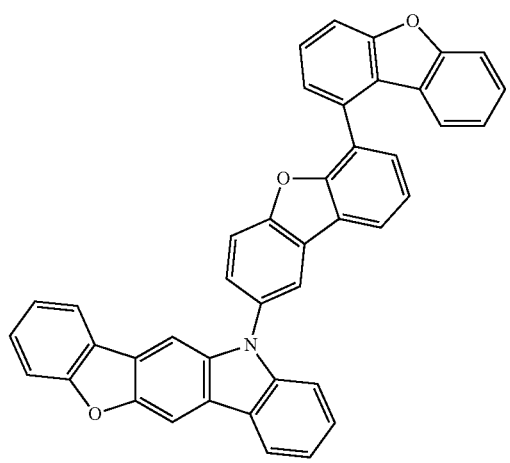

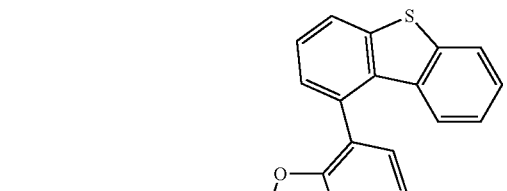
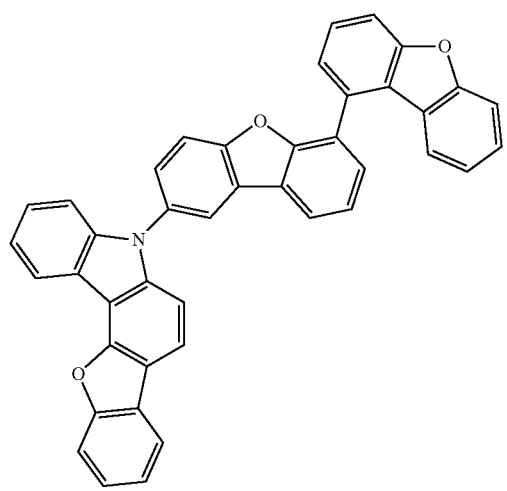
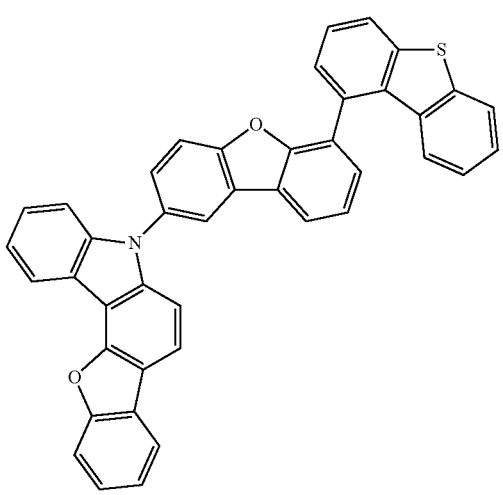
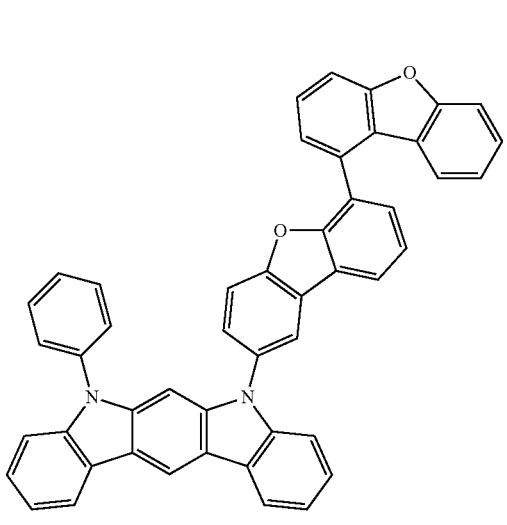

51
-continued
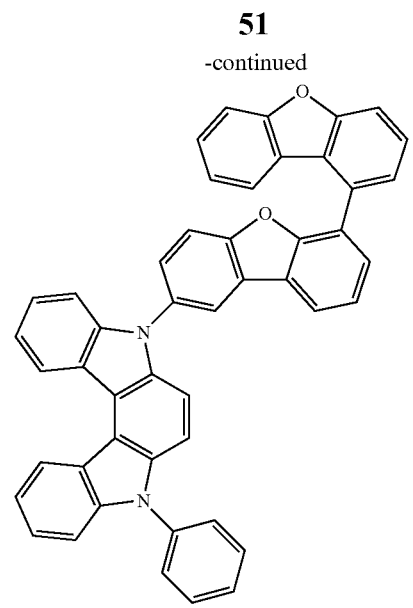
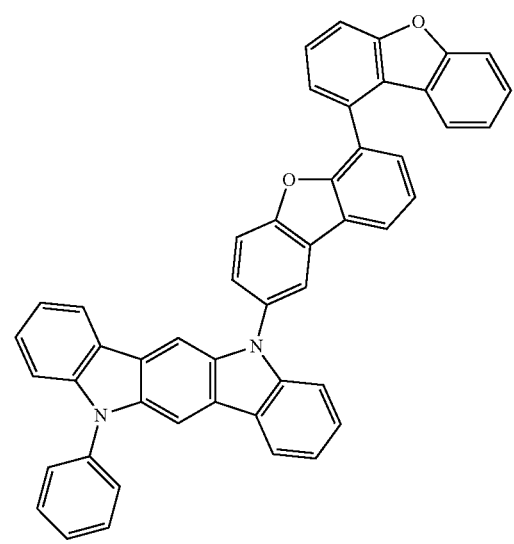
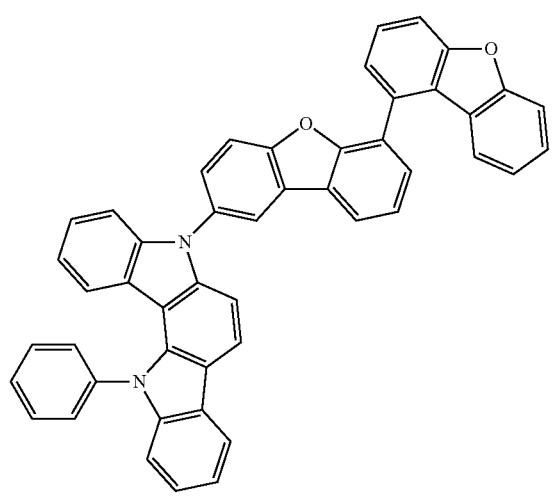
52
-continued
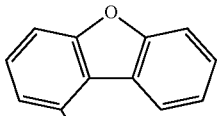
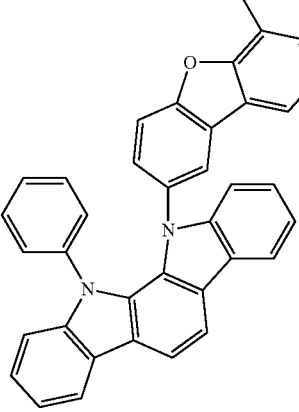
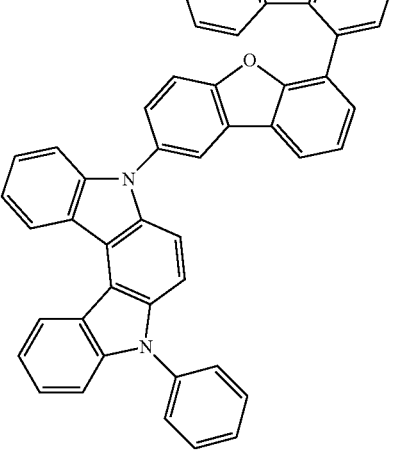

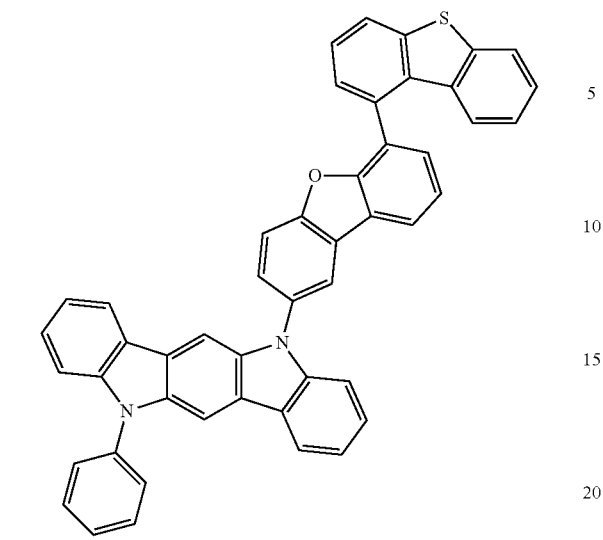
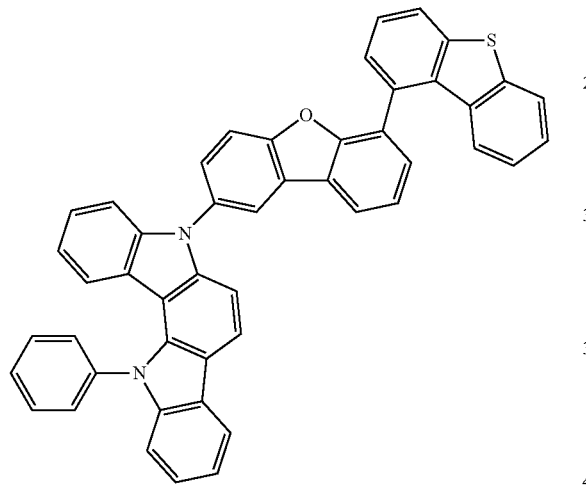
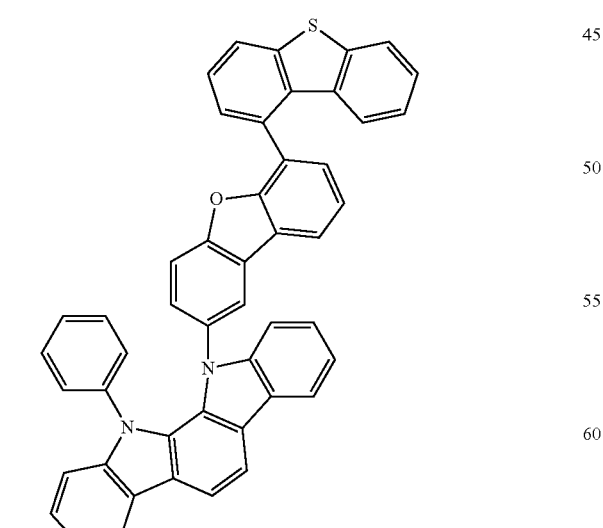
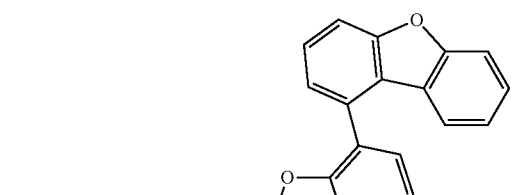

55
-continued
56
-continued
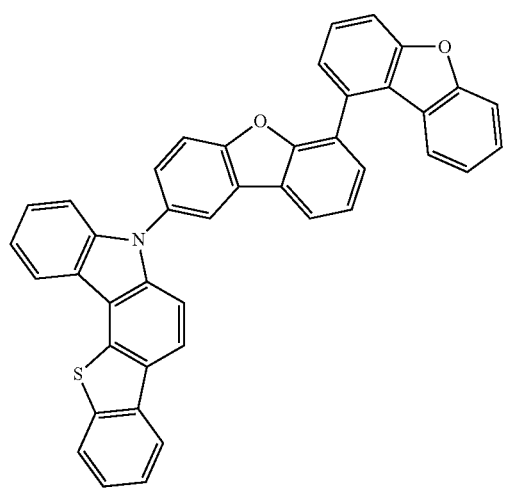
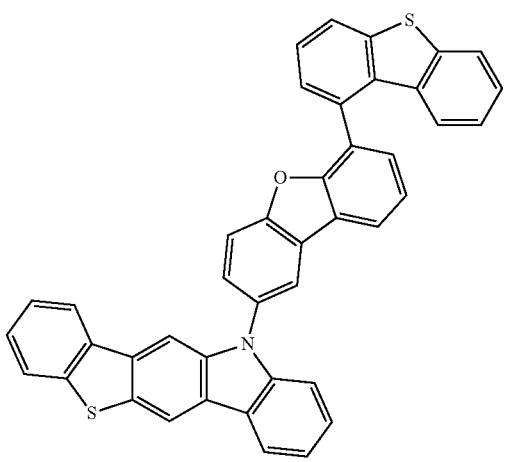
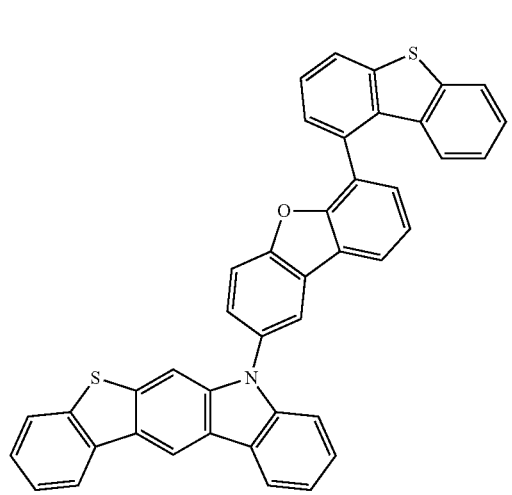
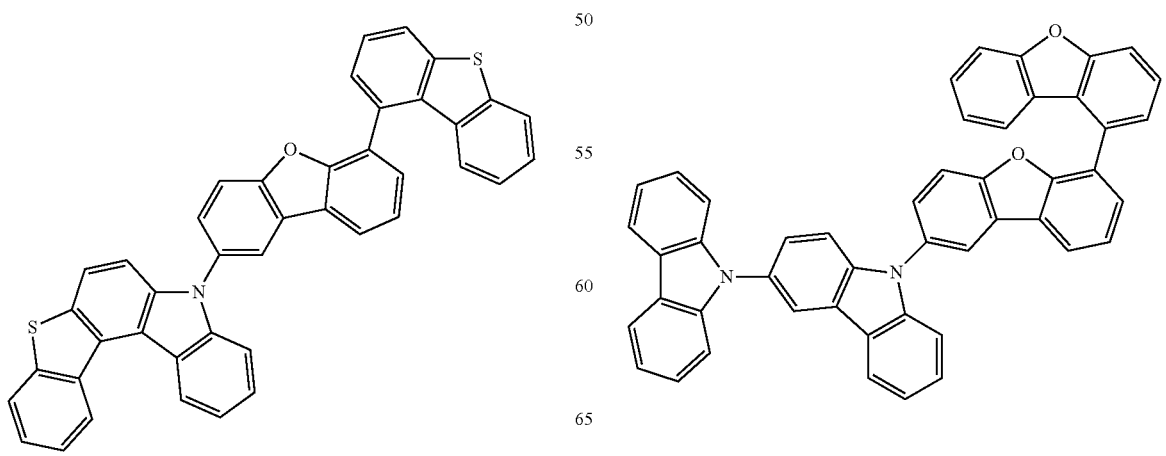

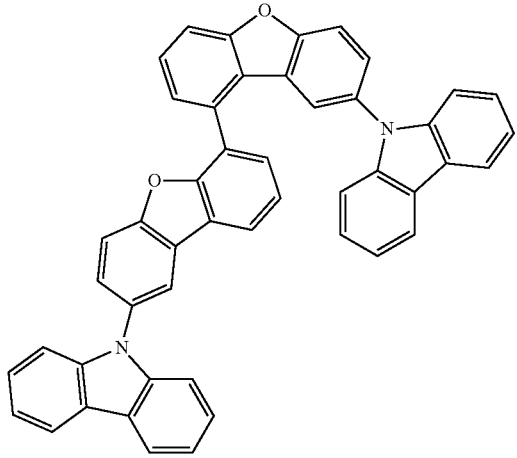
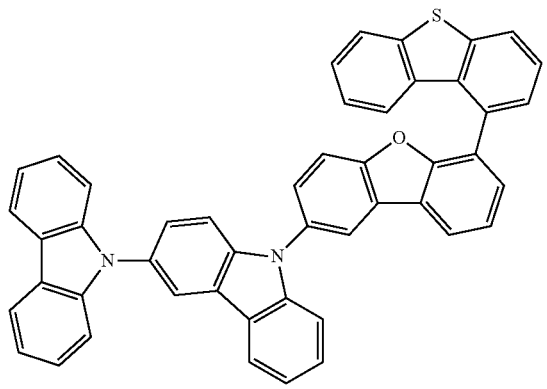
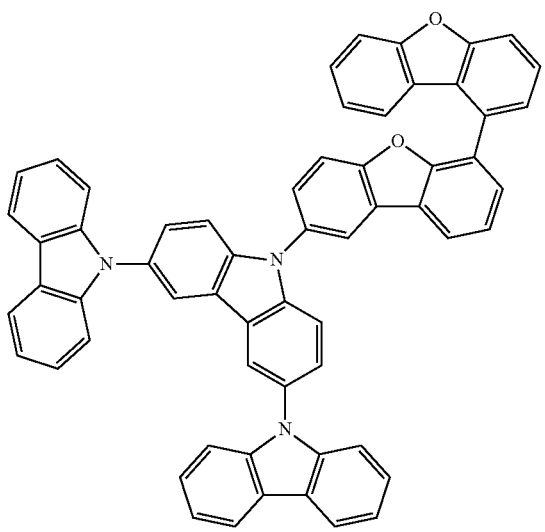
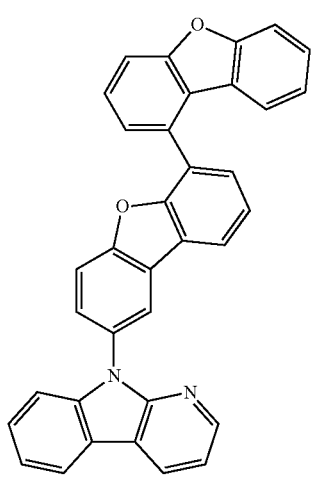
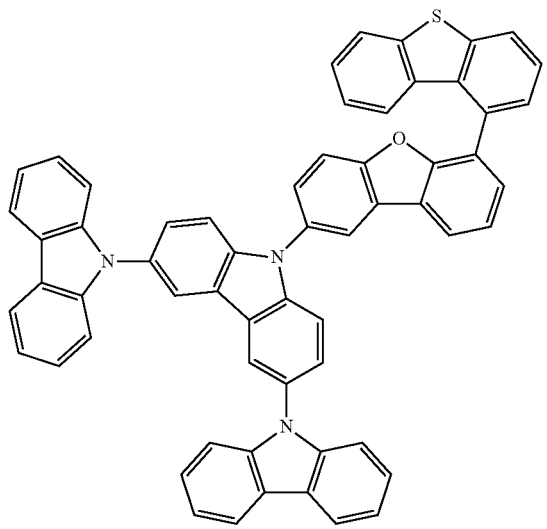

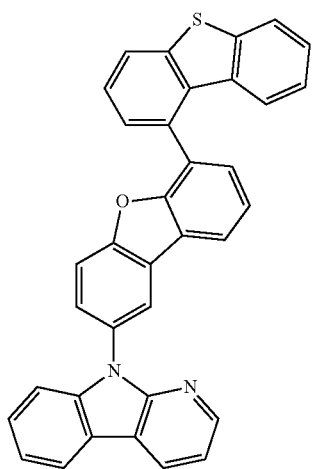
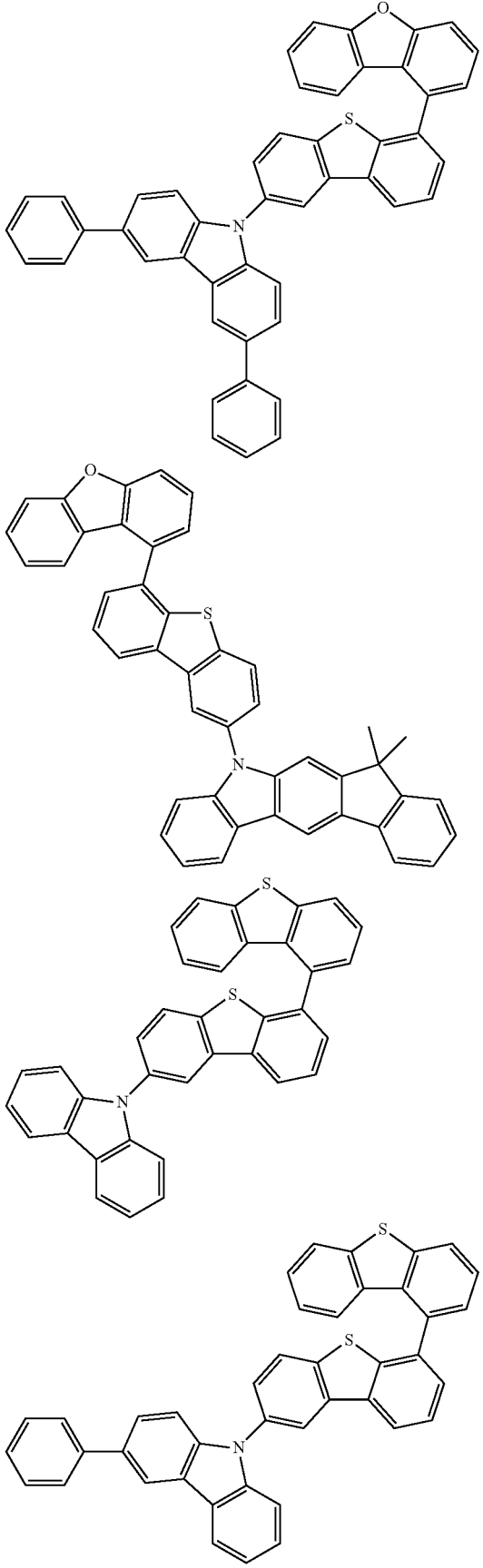

61
-continued
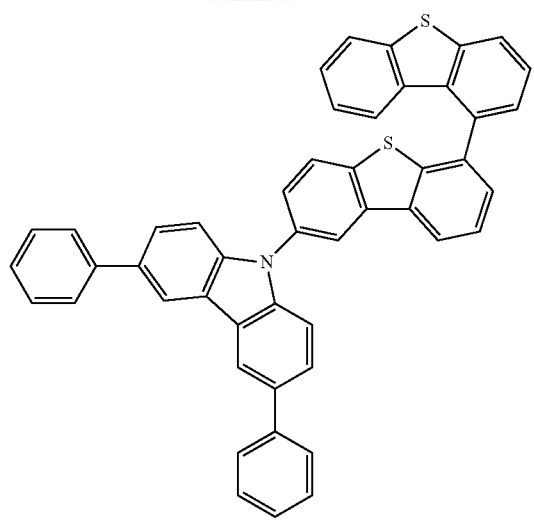
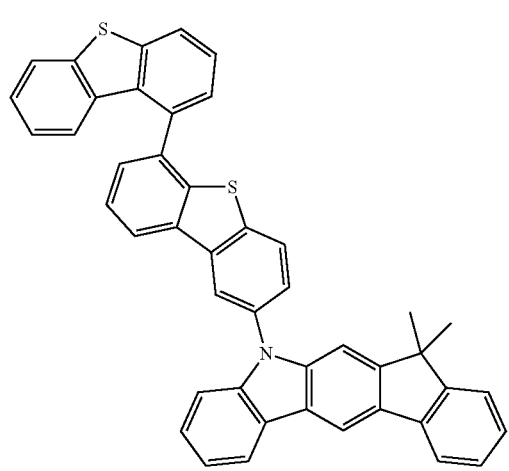
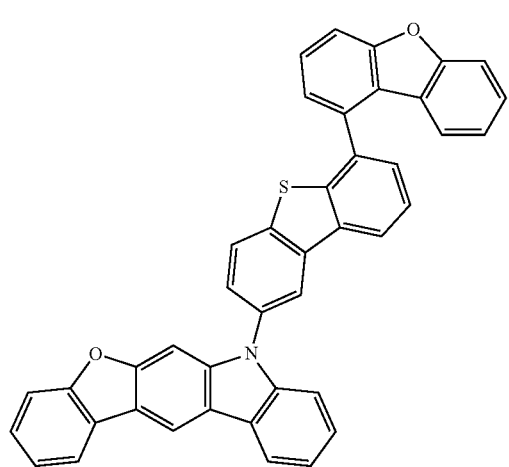
62
-continued
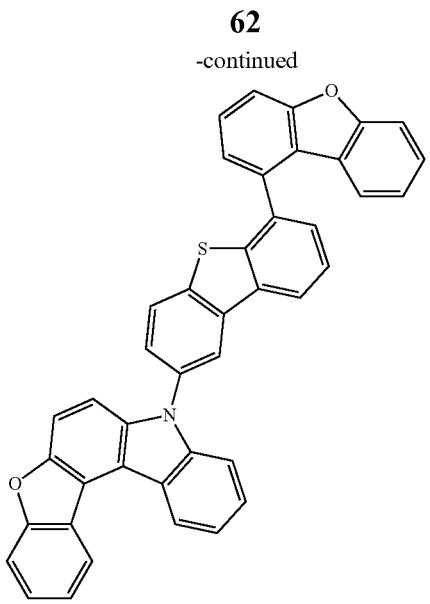
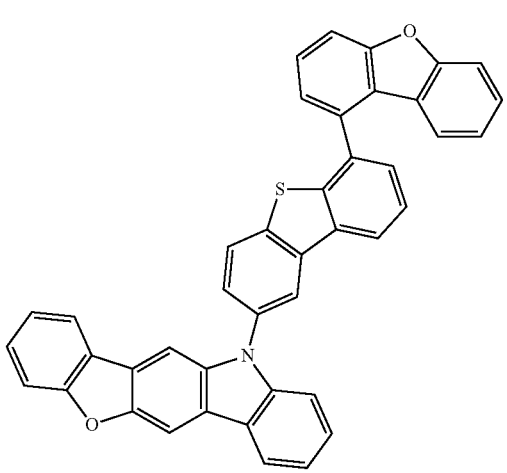
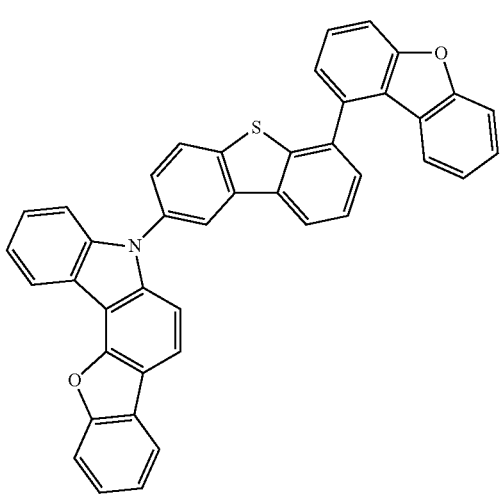

63
-continued
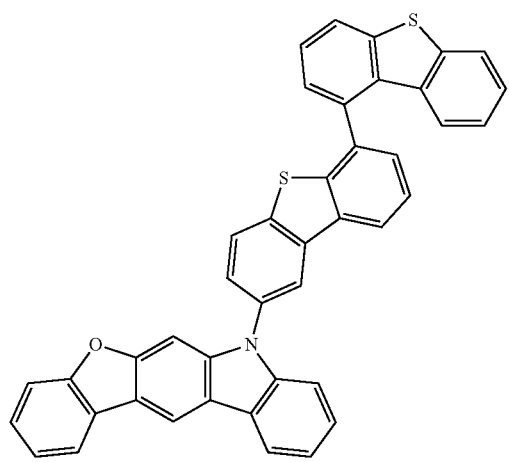
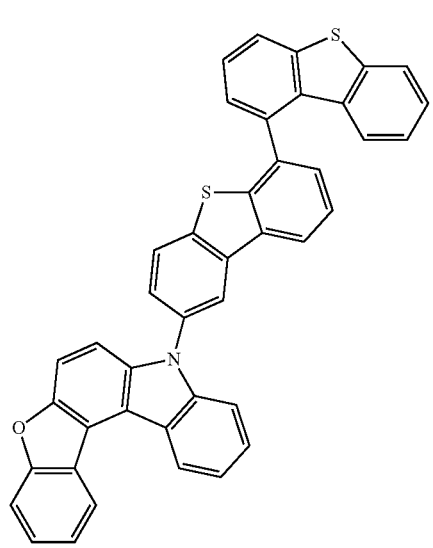
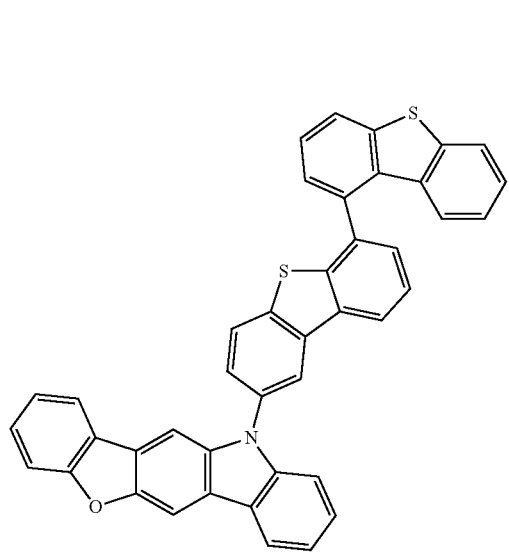
64
-continued
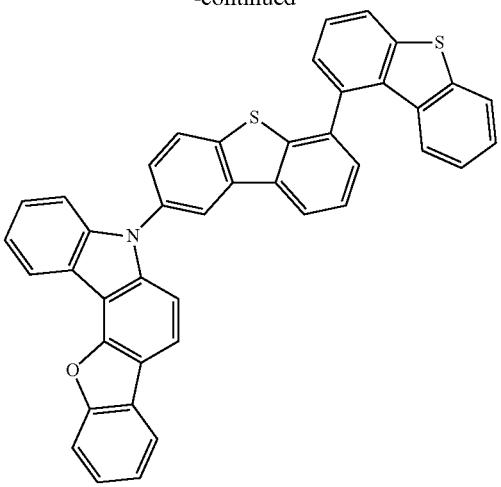
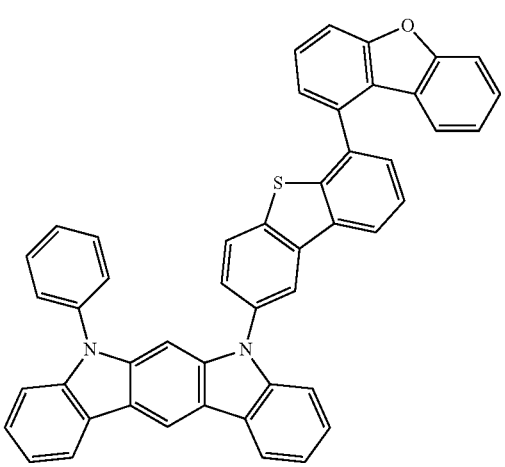
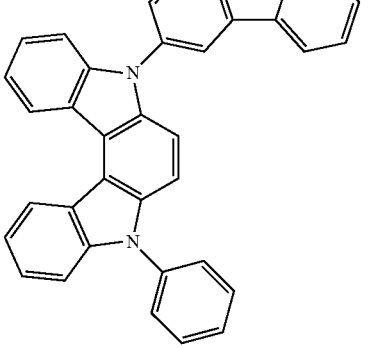

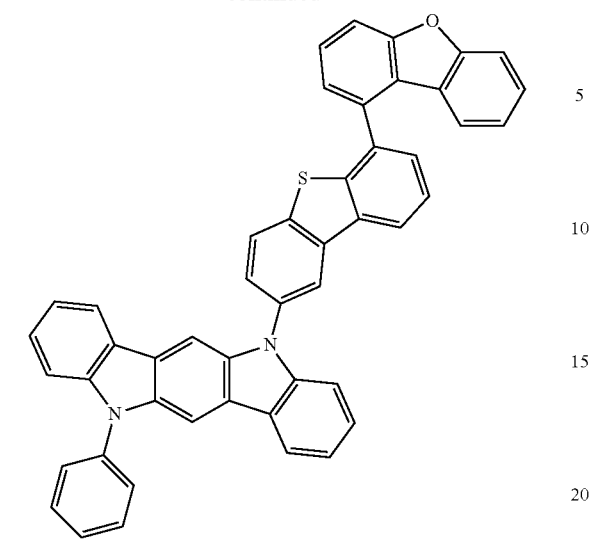
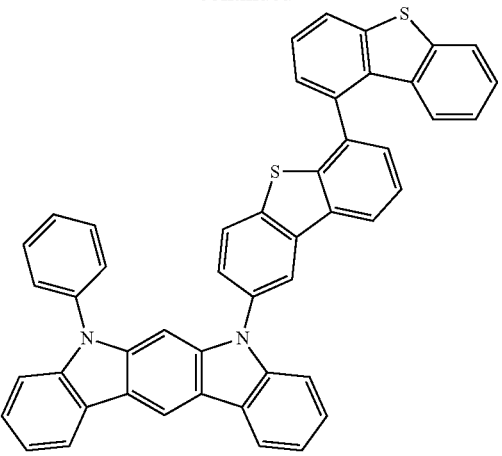

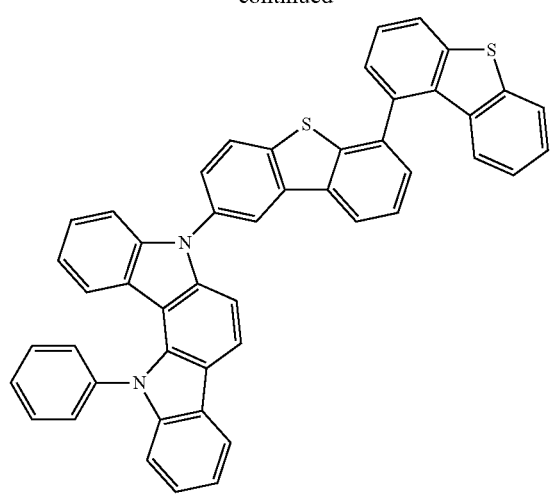
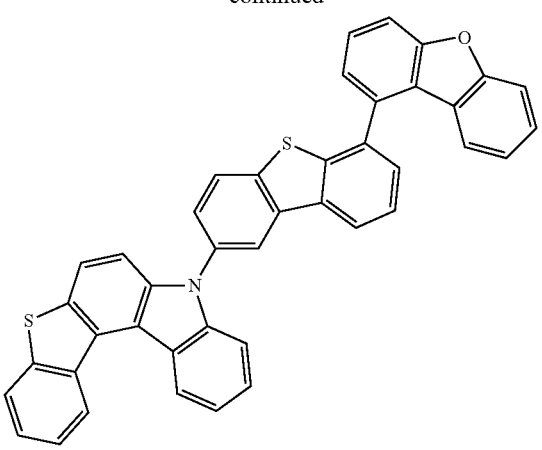
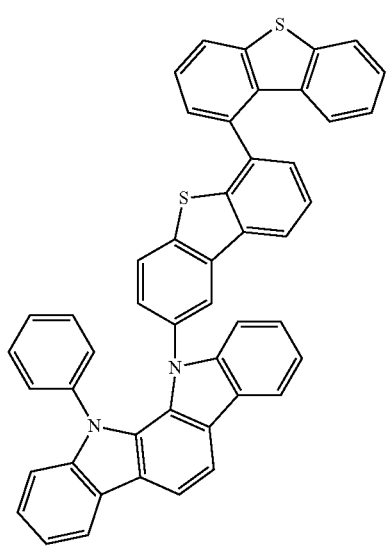
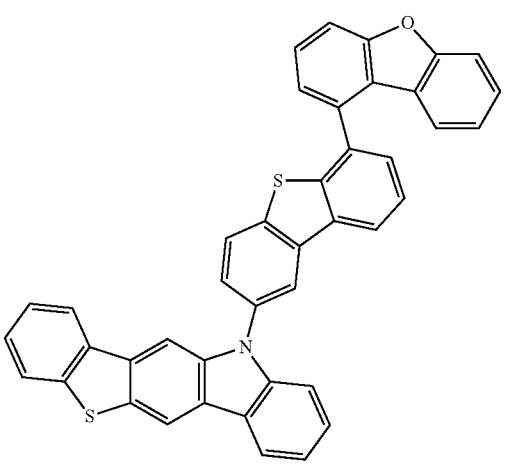
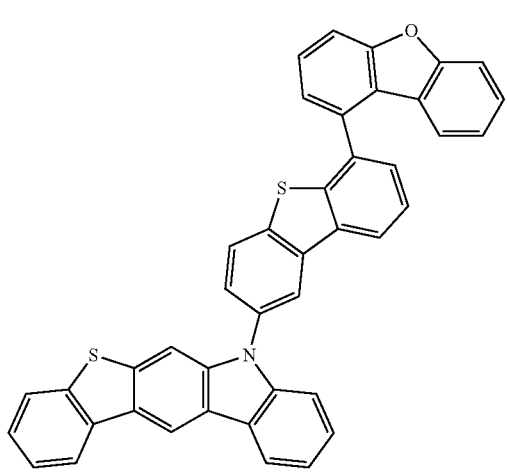
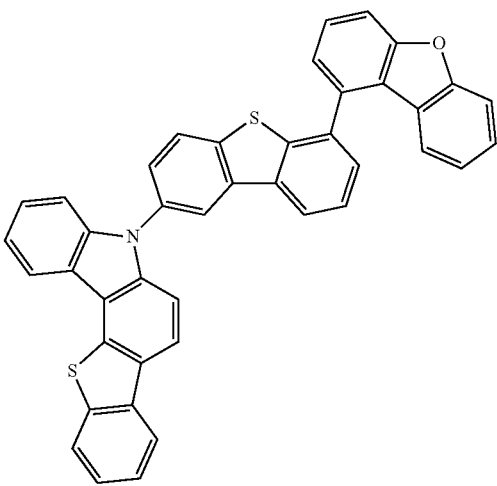

-continued
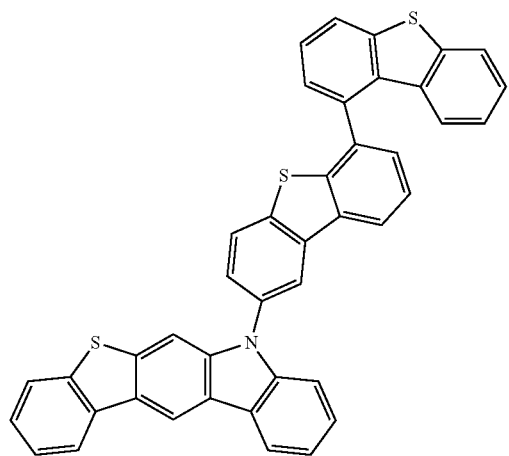
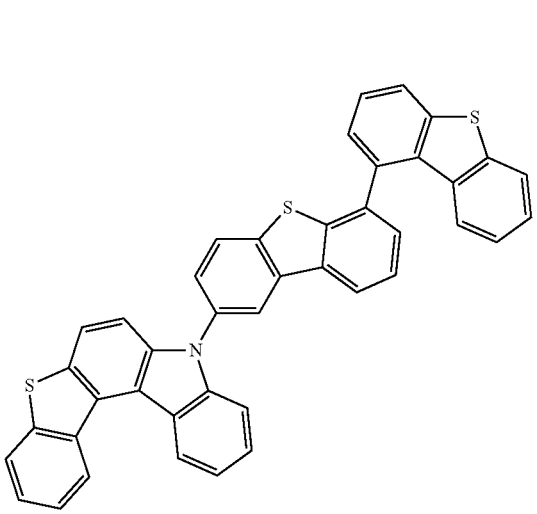
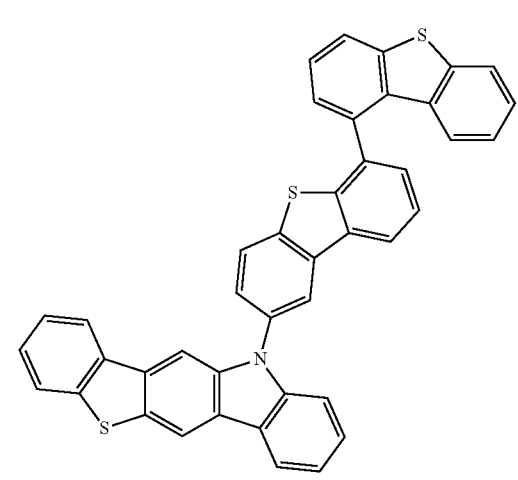
-continued
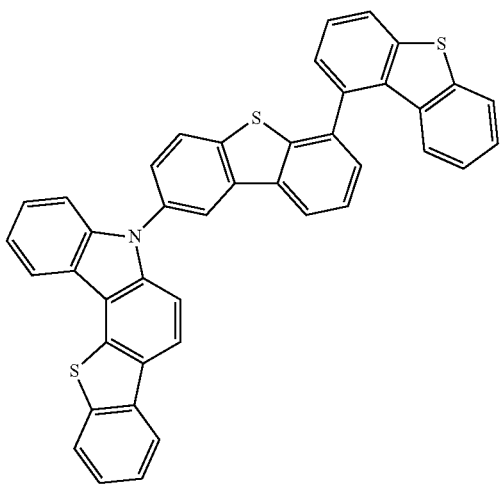
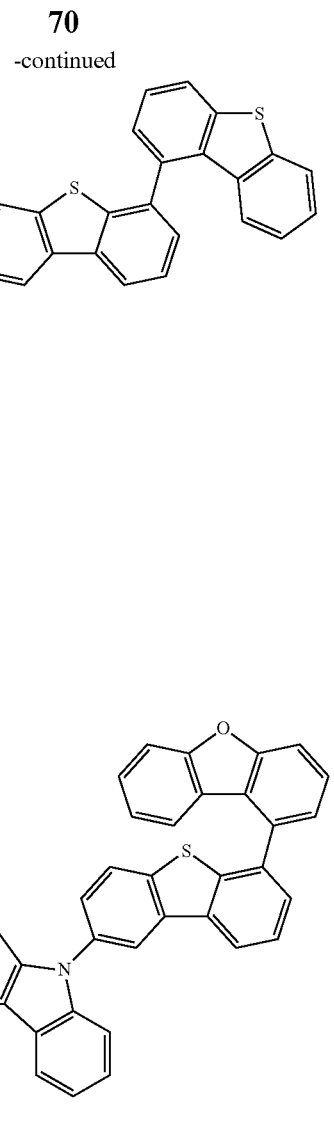
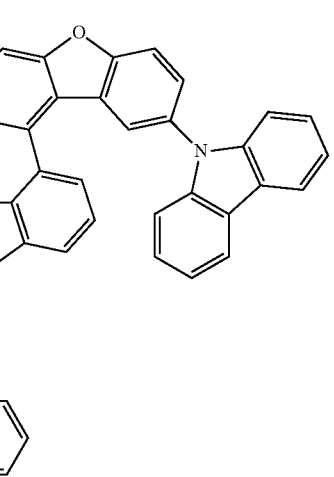

71
-continued
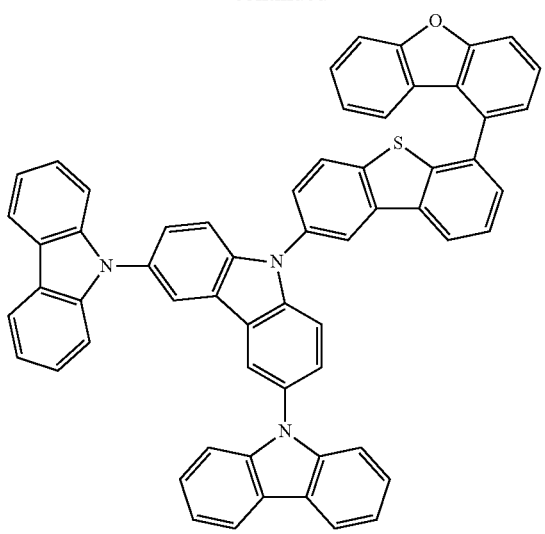
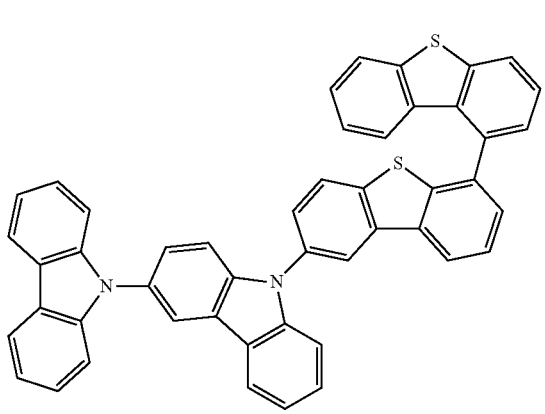
72
-continued
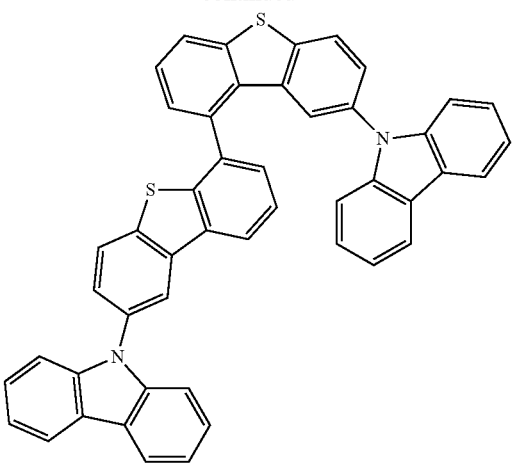
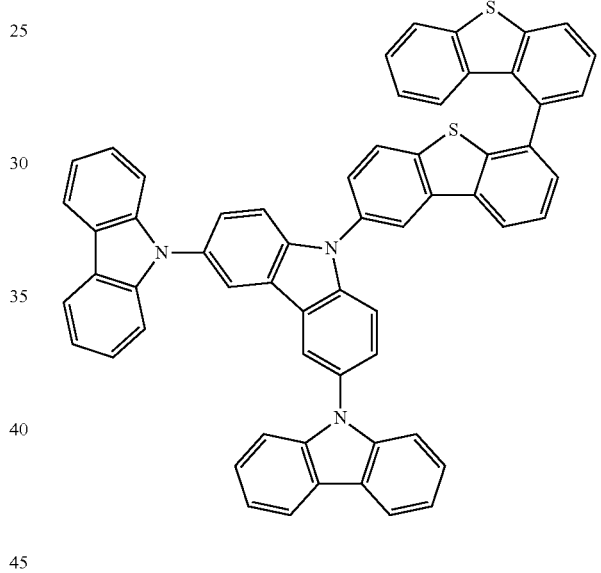
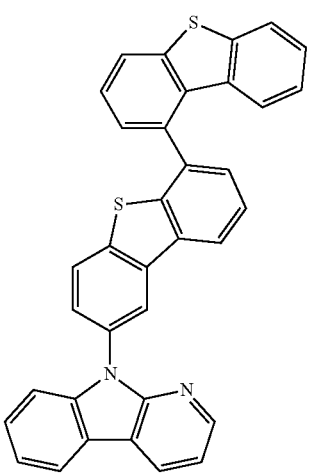

73
-continued
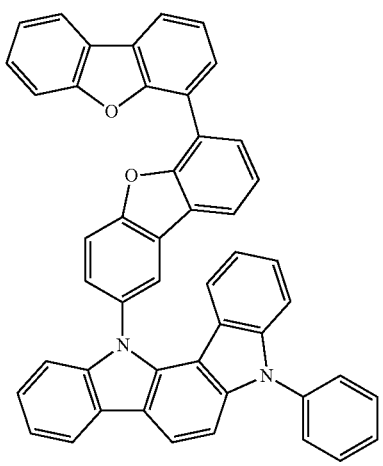
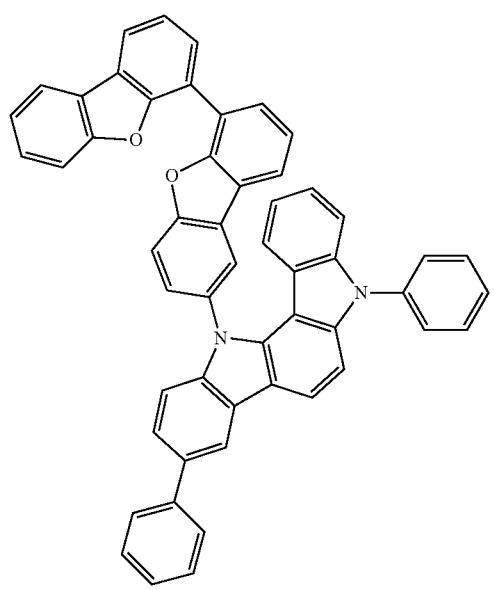
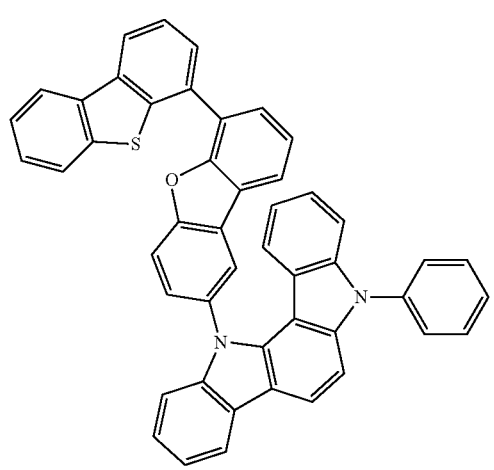
74
-continued
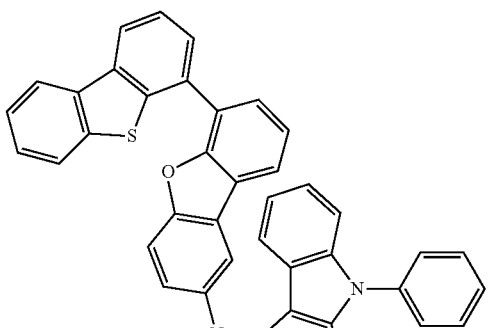
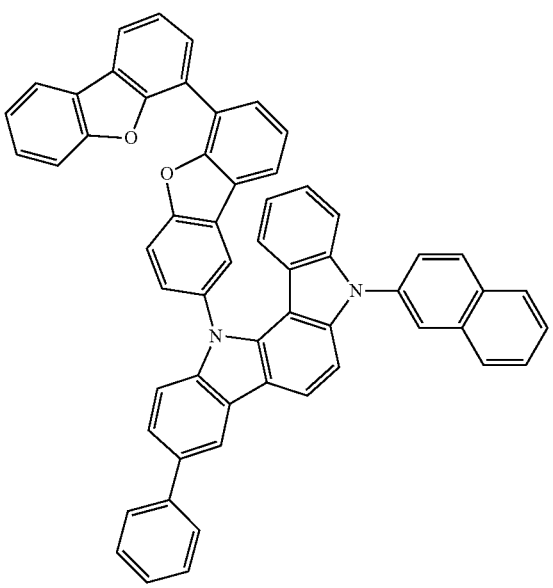

75
-continued
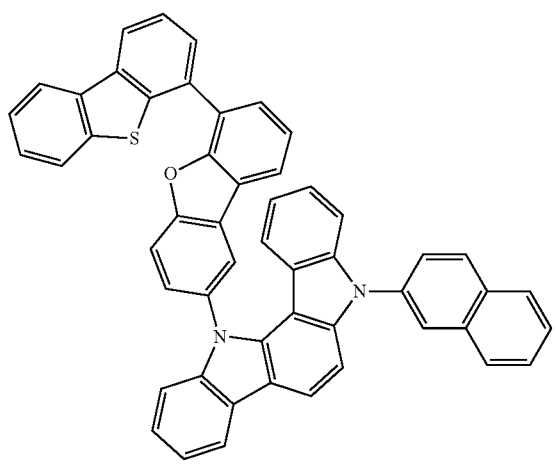
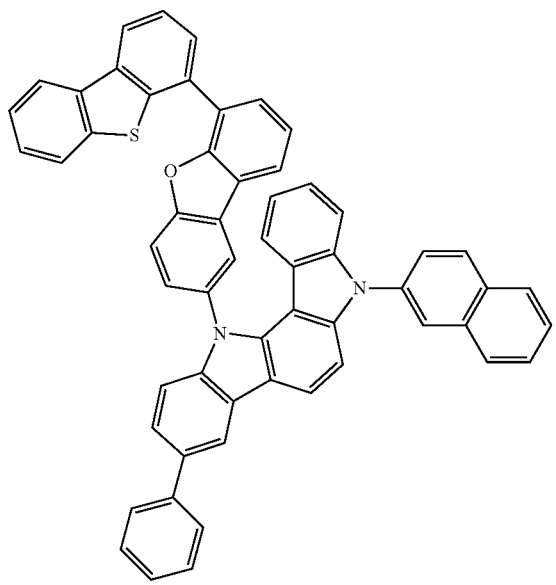
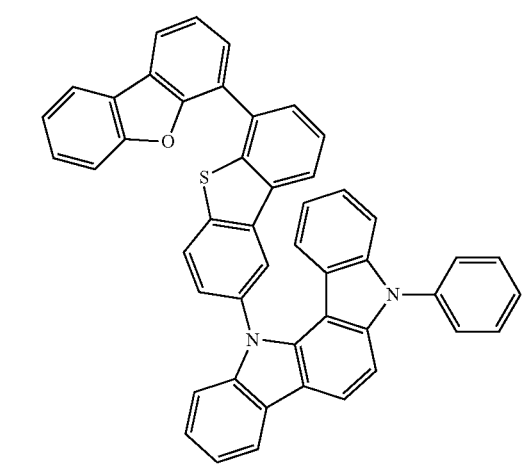
76
-continued
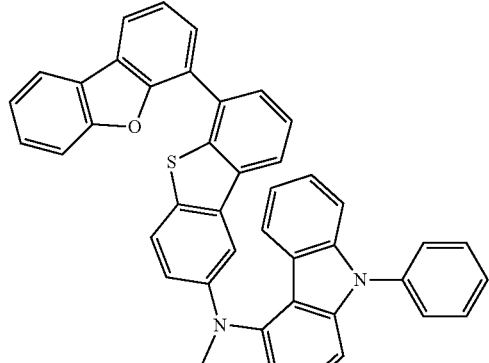
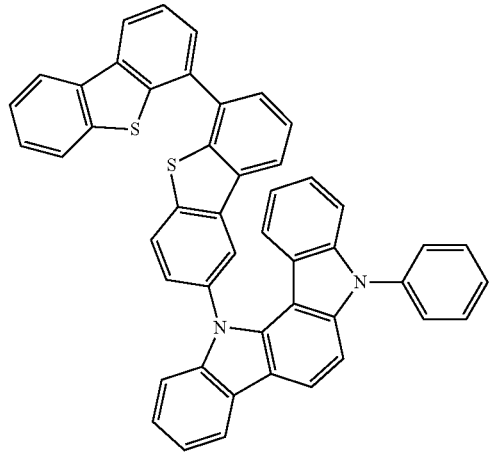
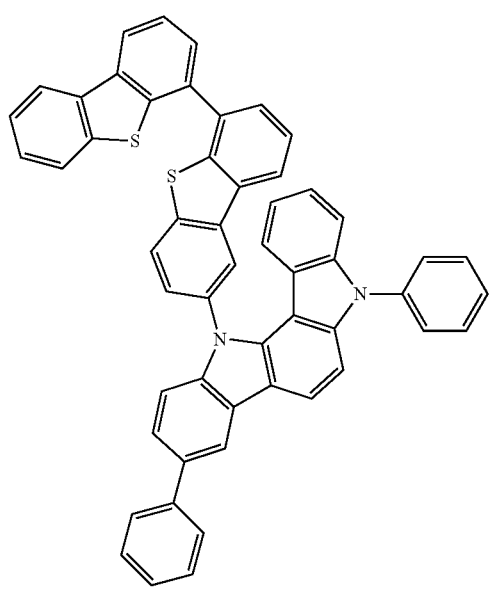

77
-continued
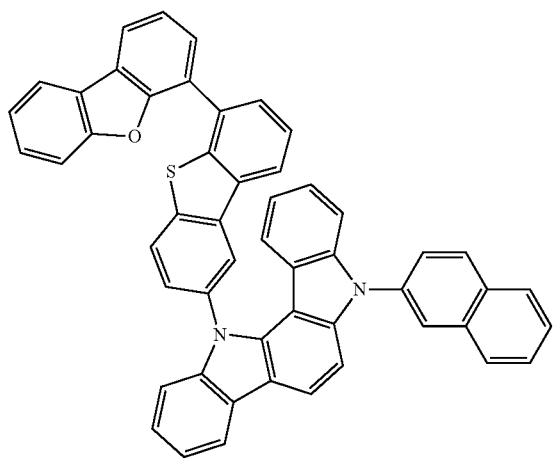
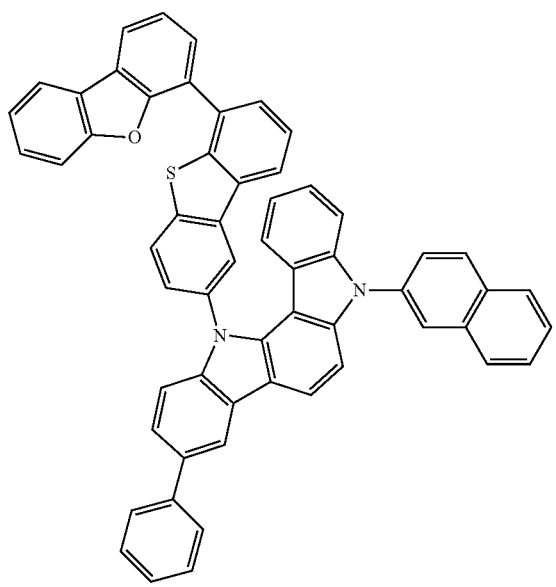
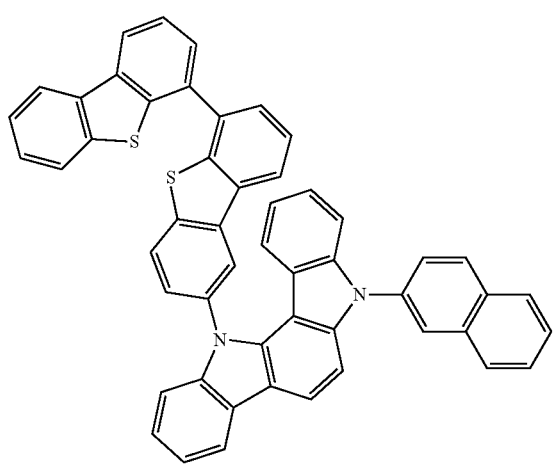
78
-continued
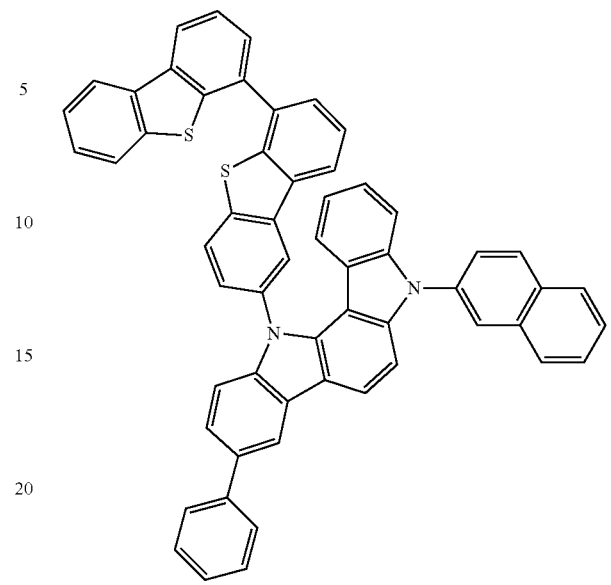
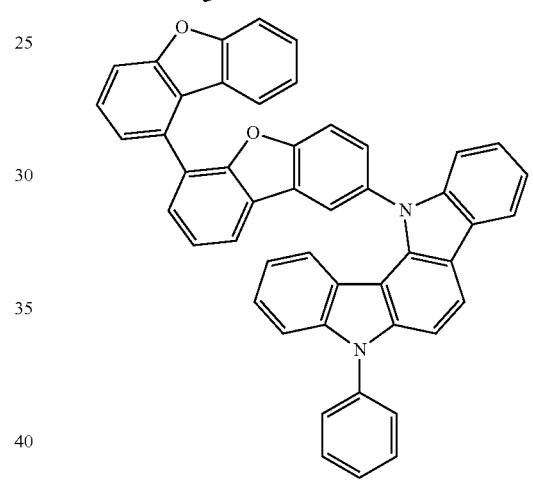
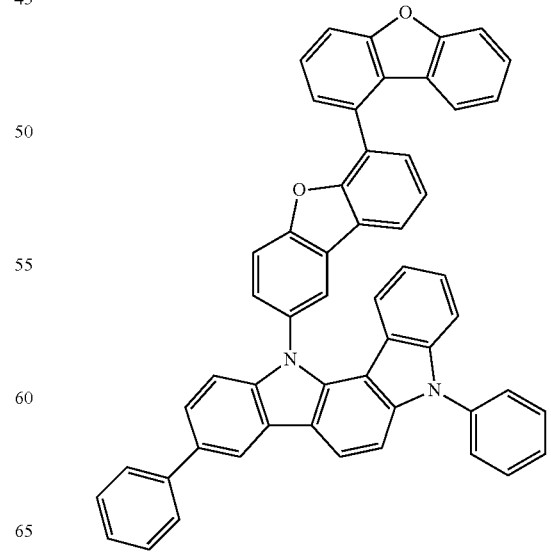

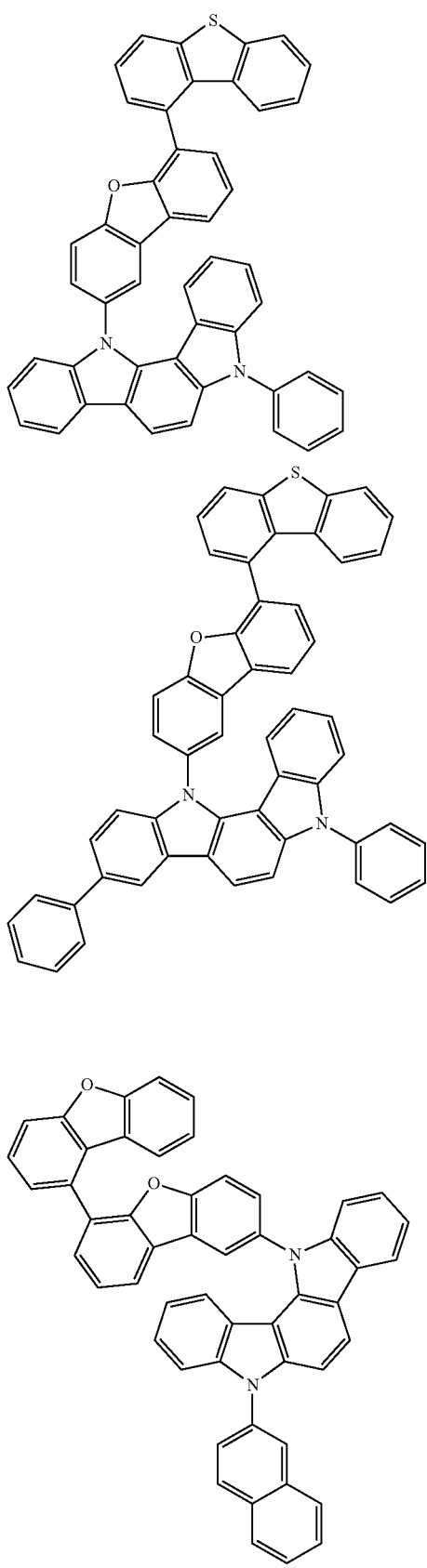
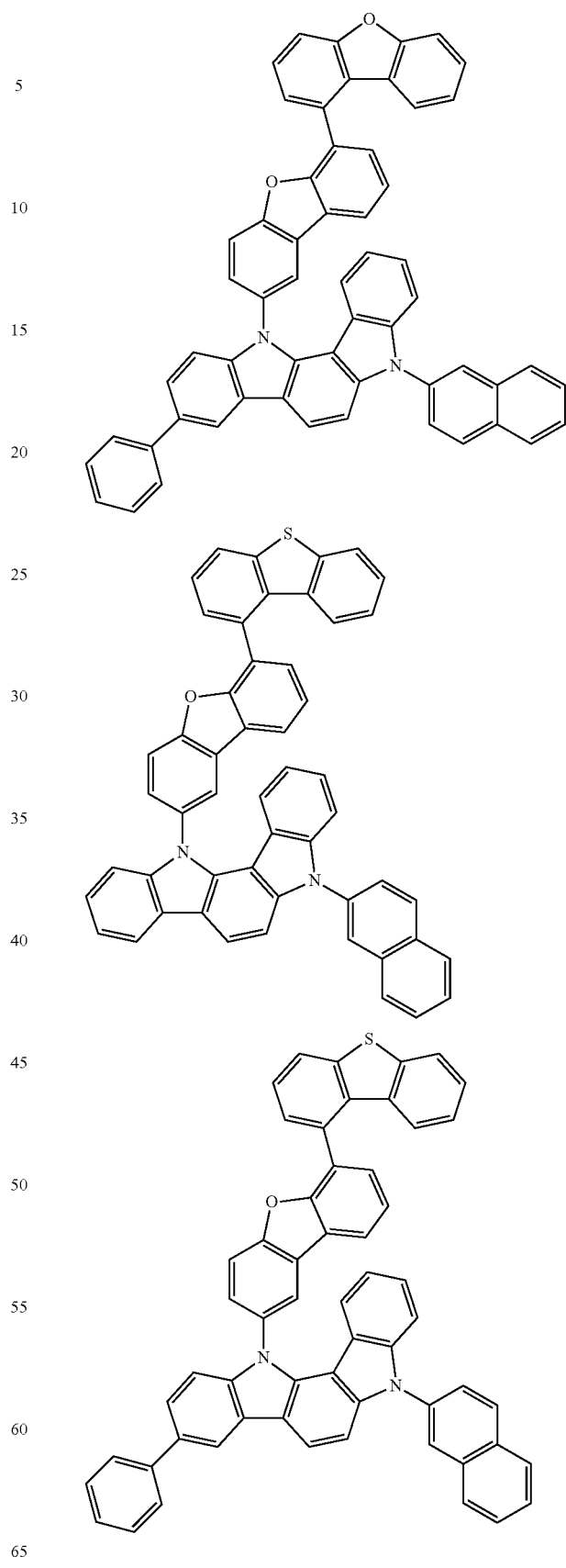

81
-continued
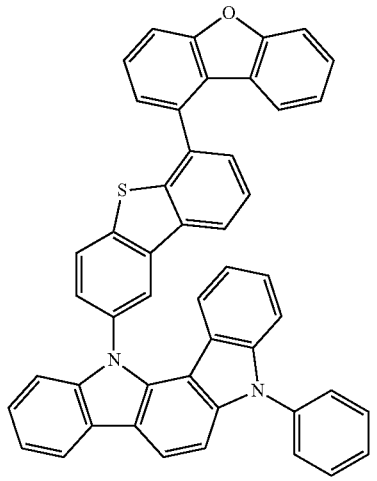
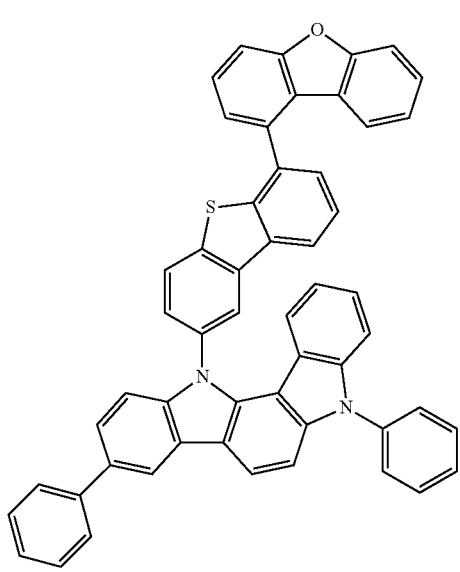
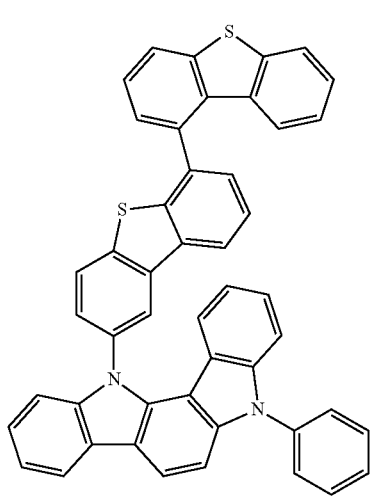
82
-continued
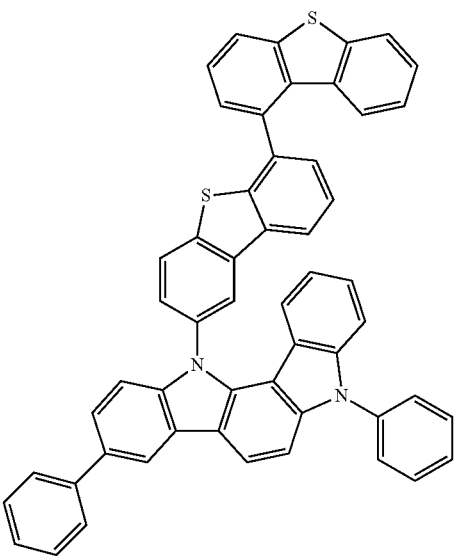
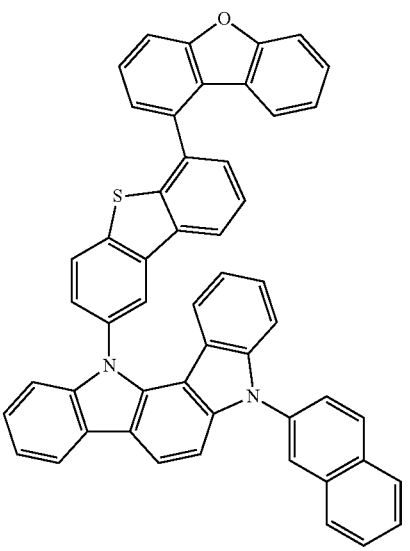
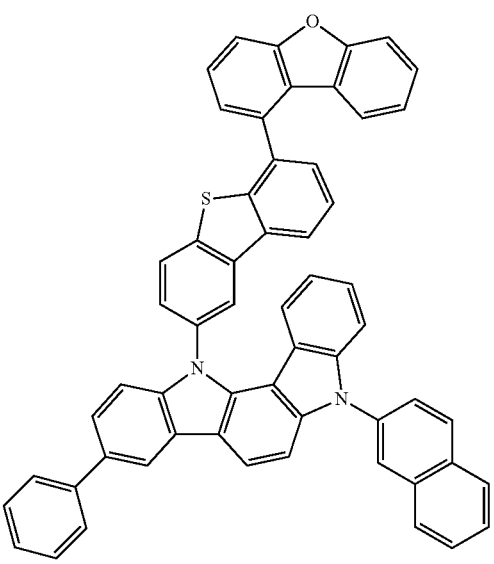

83
-continued
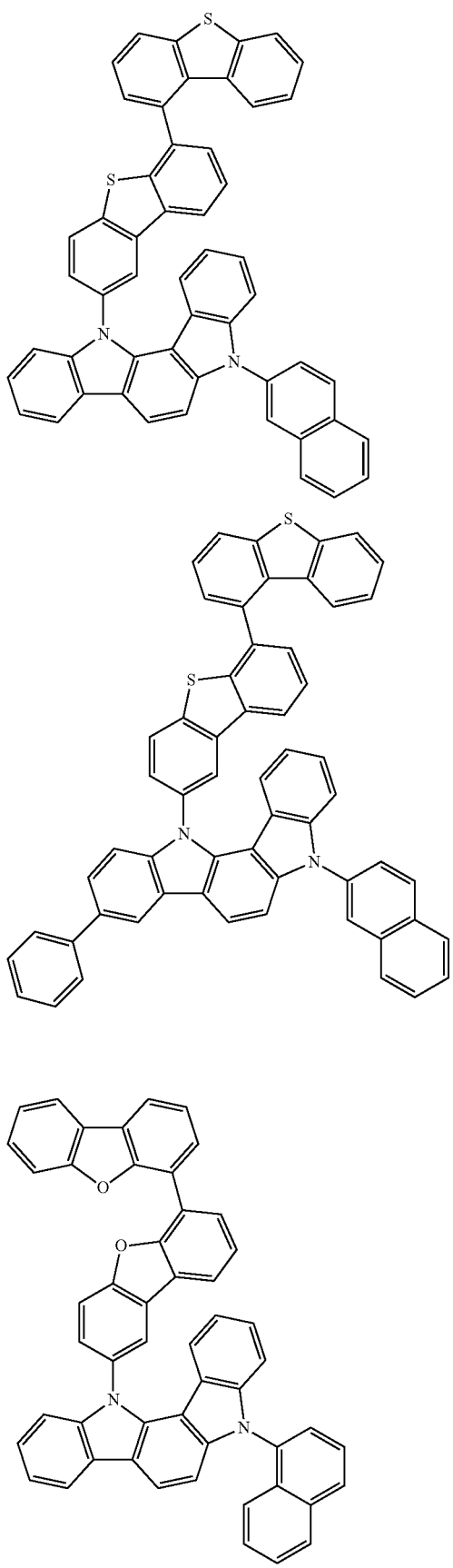 [SMILES: c1ccc2cc(-n3c4ccccc4c4c3ccc3c5ccccc5n(-c5ccc6sc7c(-c8cccc9sc%10ccccc%10c89)cccc7c6c5)c34)ccc2c1 ; c1ccc(-c2ccc3c(c2)c2ccc4c(c5ccccc5n4-c4ccc5ccccc5c4)c2n3-c2ccc3sc4c(-c5cccc6sc7ccccc7c56)cccc4c3c2)cc1 ; c1ccc2c(-n3c4ccccc4c4c3ccc3c5ccccc5n(-c5ccc6oc7c(-c8cccc9c8oc8ccccc89)cccc7c6c5)c34)cccc2c1]
84
-continued
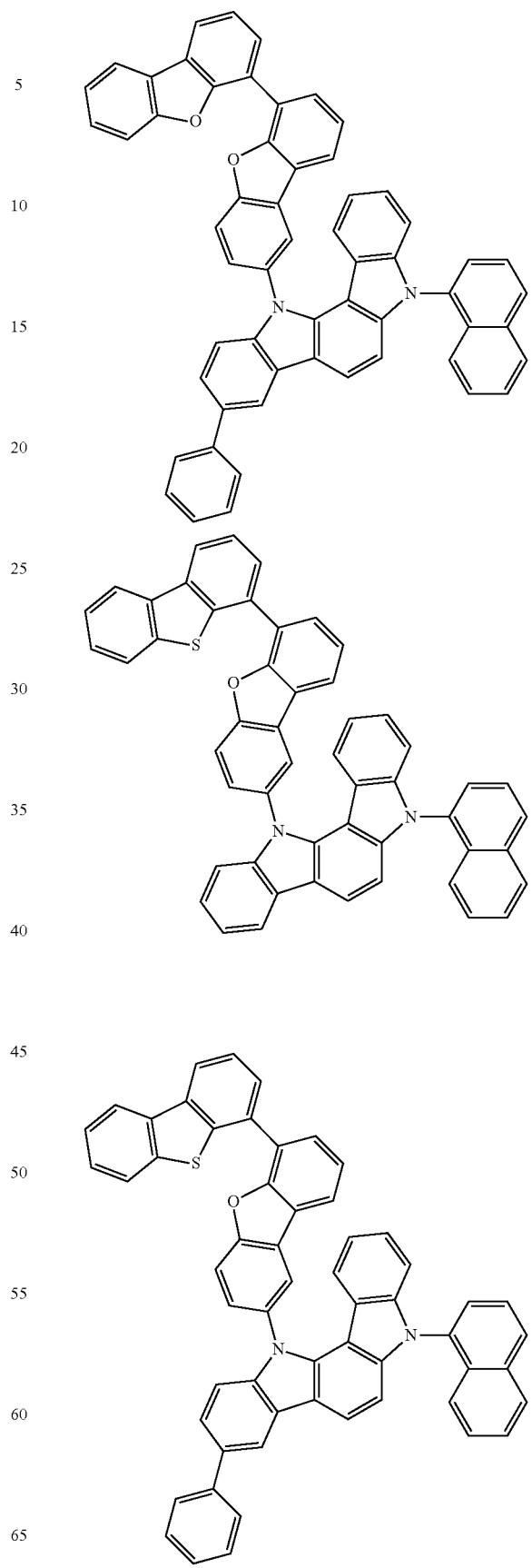

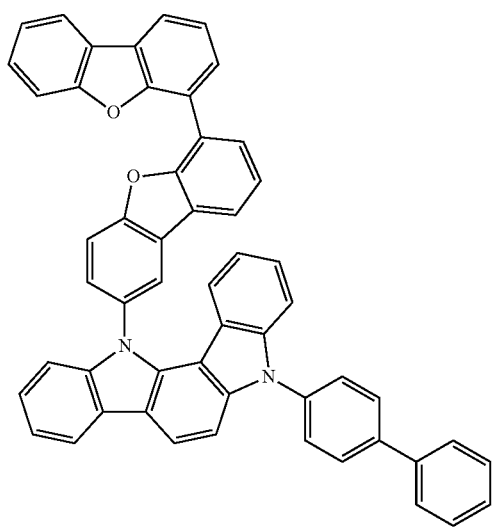
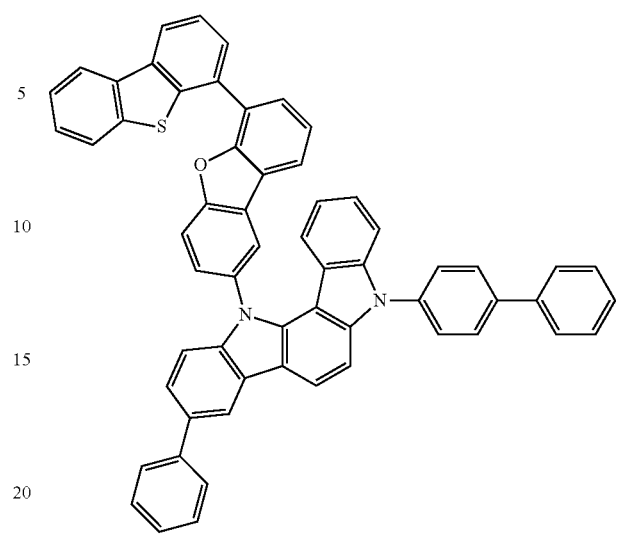
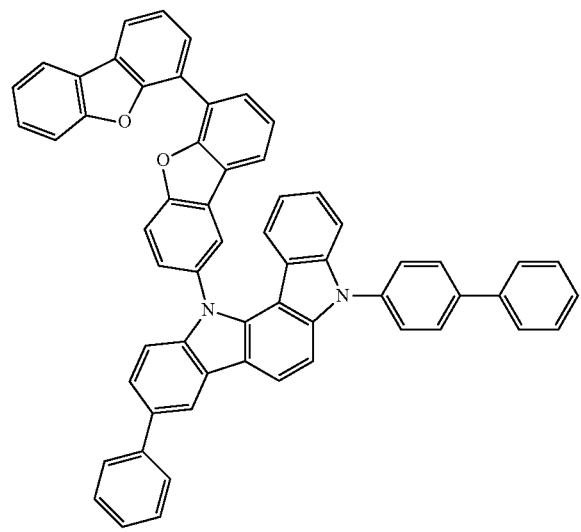
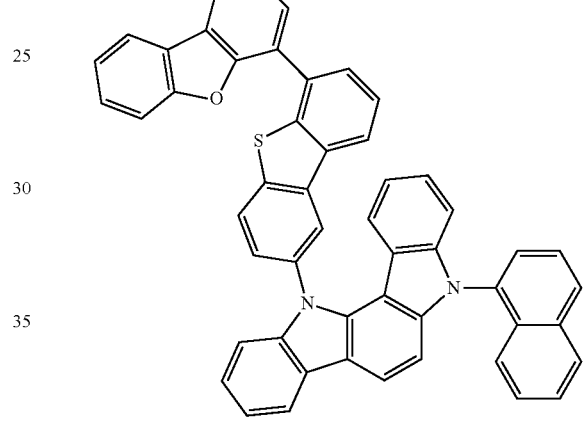
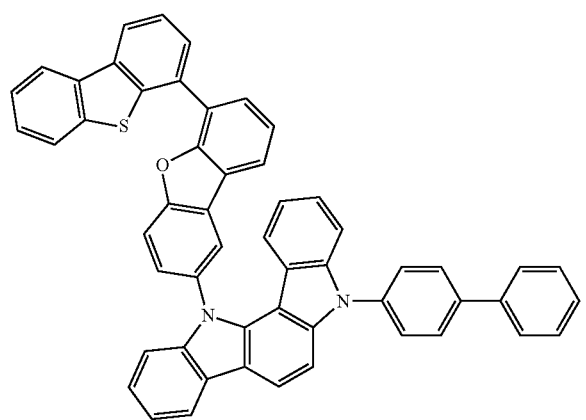
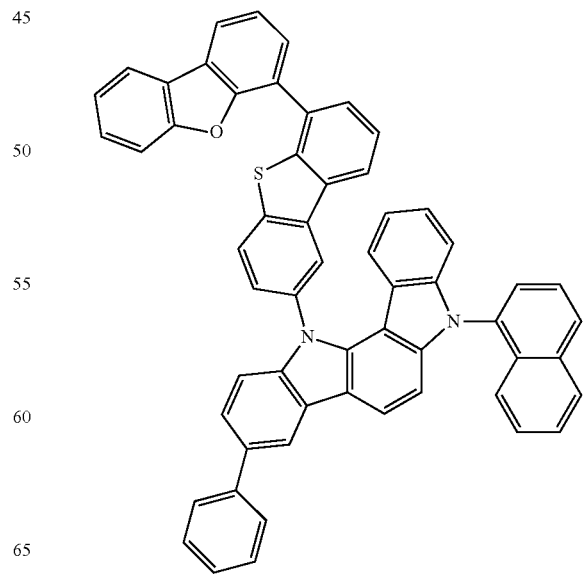

87
-continued
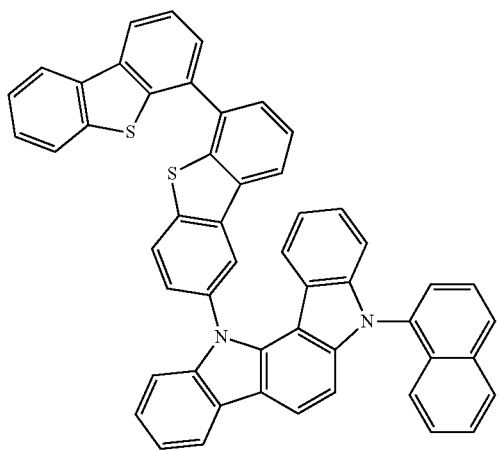
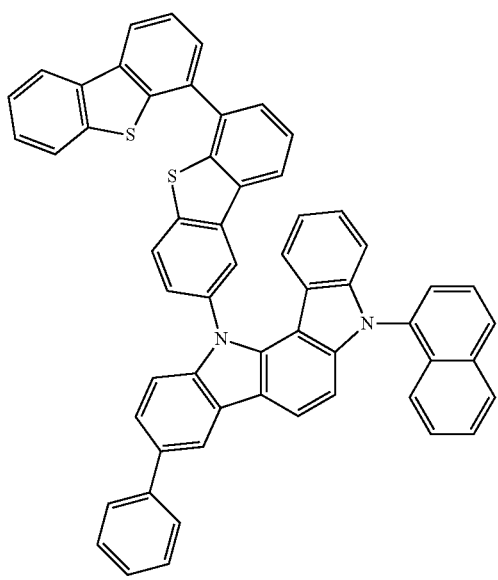
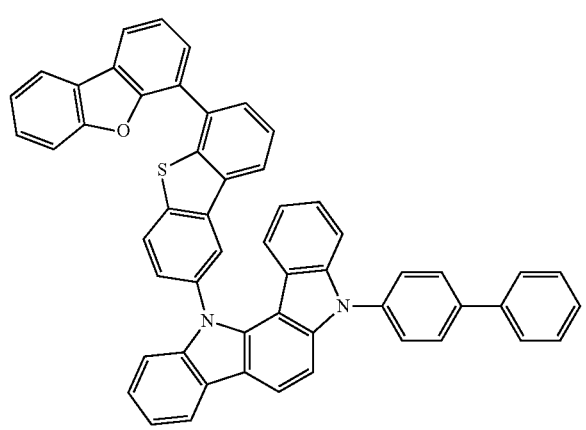
88
-continued
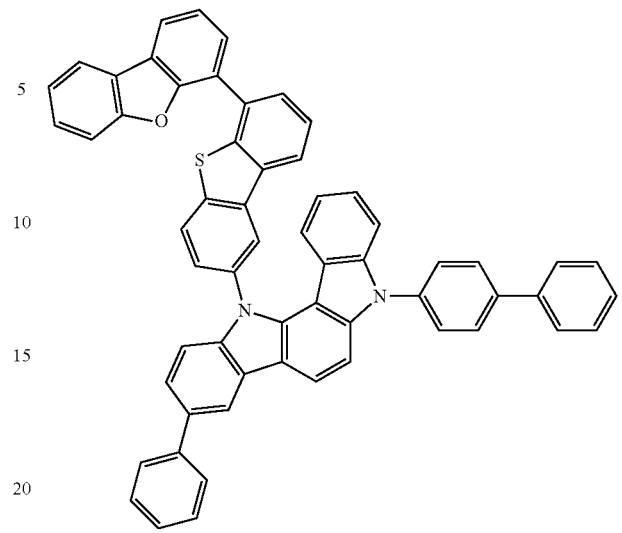
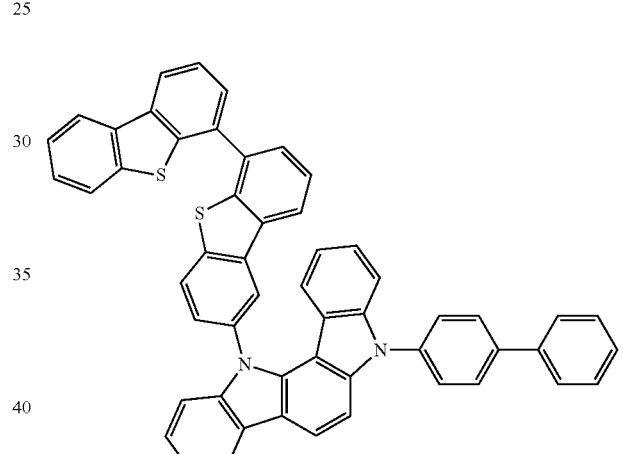
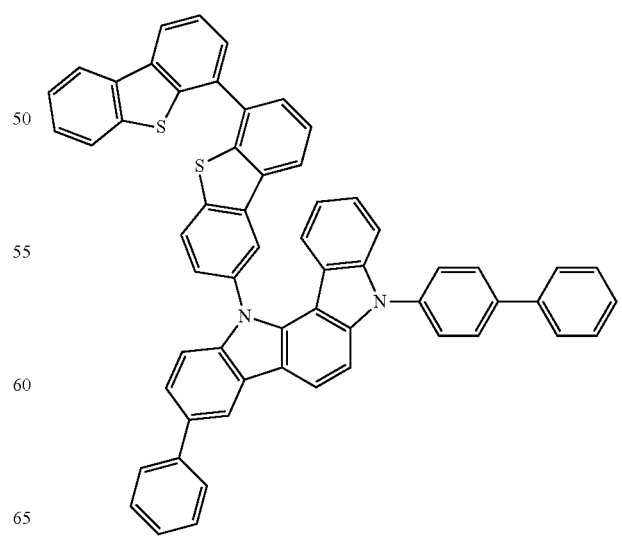

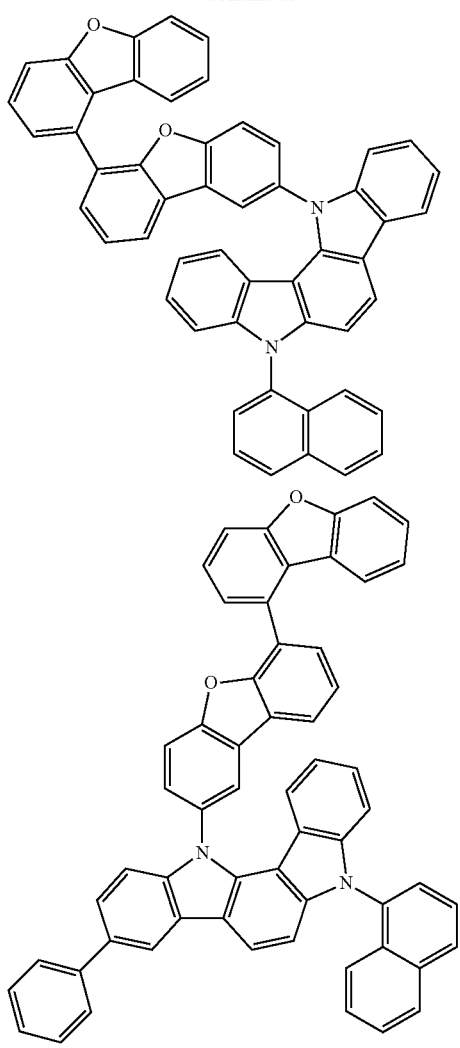
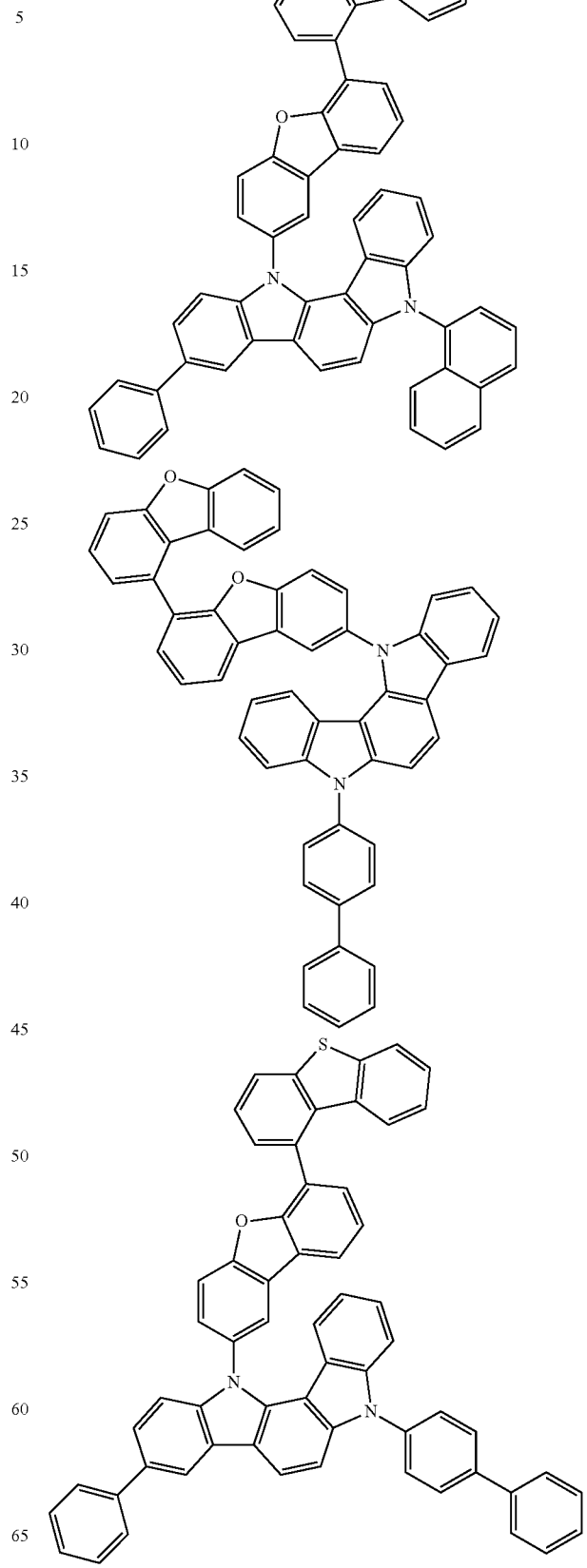

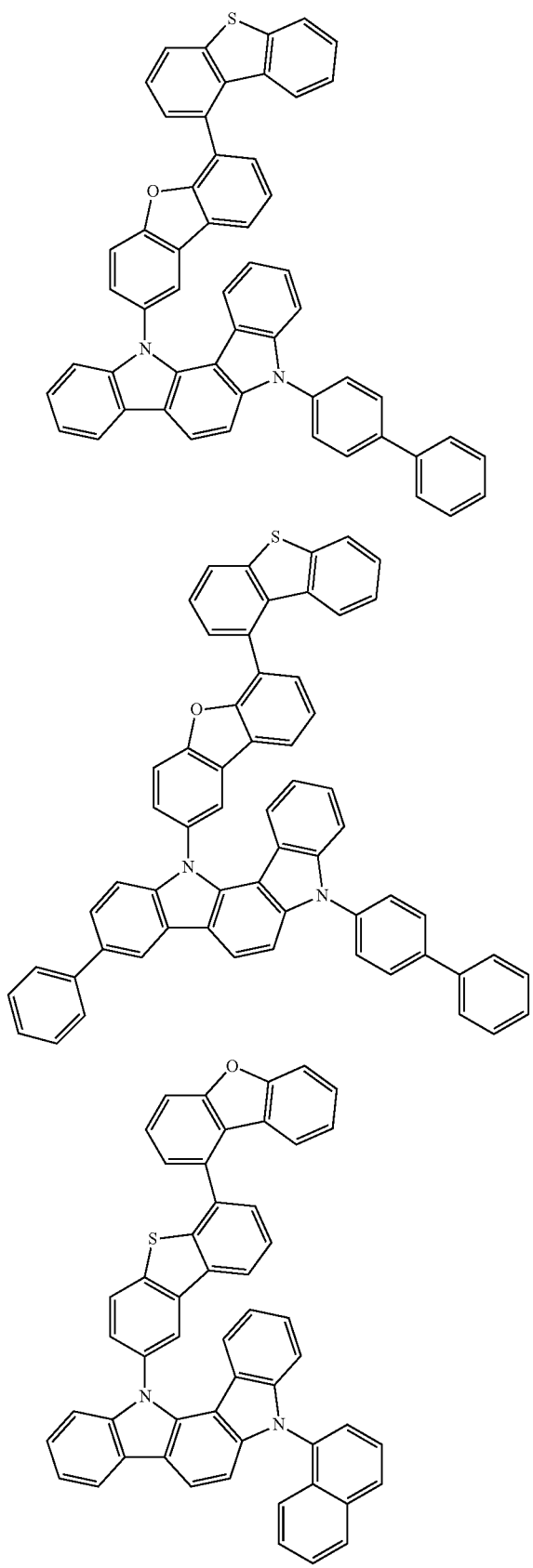
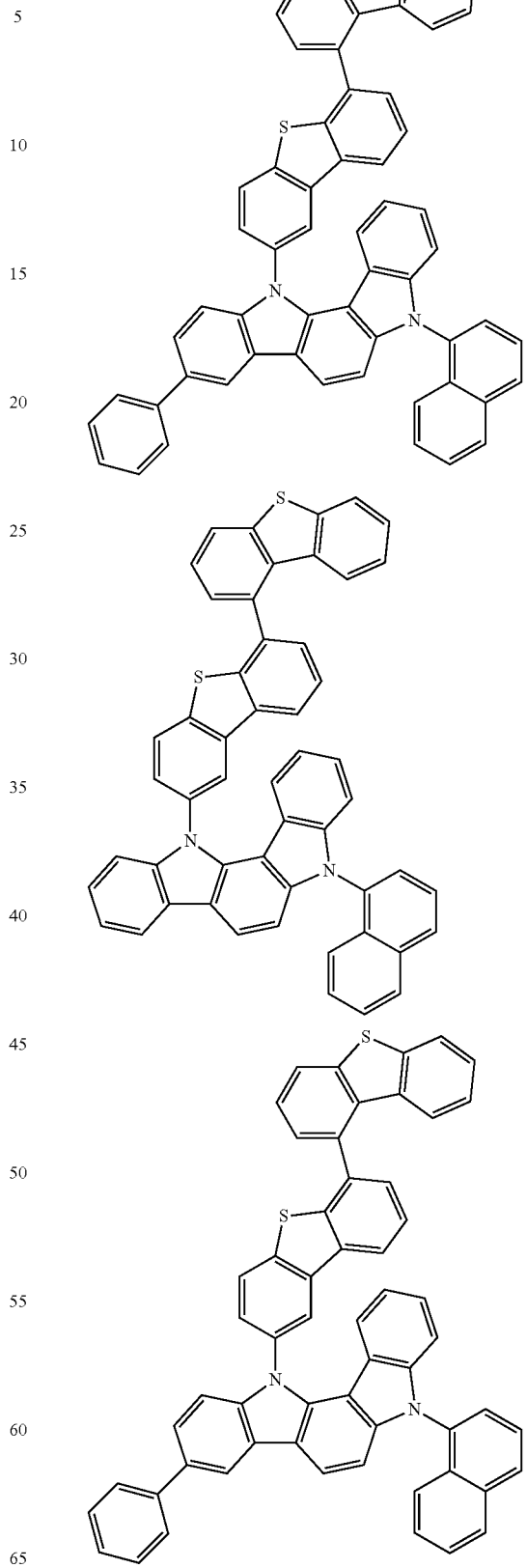

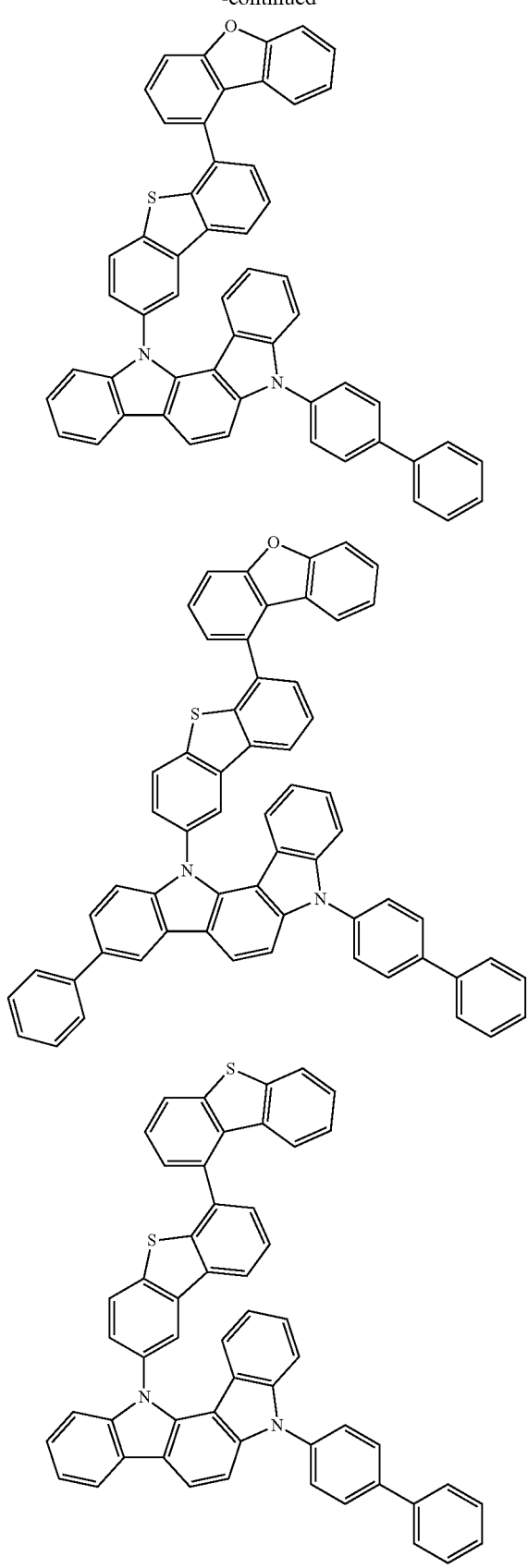

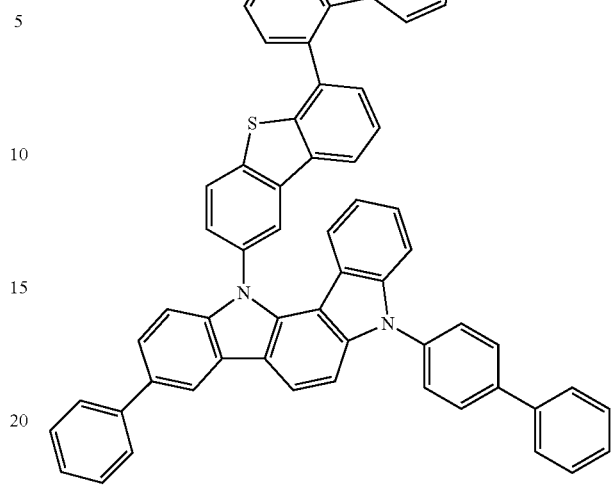

The first compound having the structure of anyone in Chemical Formulae 2 to 4 includes the carbazolyl moiety linked to the central first dibenzofuranyl/dibenzothiophenyl moiety and having p-type property, and the second dibenzofuranyl/dibenzothiophenyl moiety linked to the first dibenzofuranyl/dibenzothiophenyl moiety and having n-type property, and the carbazolyl moiety and the second dibenzofuranyl/dibenzothiophenyl moiety are linked to the first dibenzofuranyl/dibenzothiophenyl moiety asymmetrically.

In other words, each of the carbazolyl moiety having p-type property and the second dibenzofuranyl/dibenzothiophenyl moiety having n-type property is respectively bonded to an asymmetrical position in respective side benzene ring constituting the first dibenzofuranyl/dibenzothiophenyl moiety, so that the first compound having the structure of anyone in Chemical Formulae 2 to 4 may exhibit more amorphous property so as to improve extremely its heat resistance. Accordingly, the crystallization caused by Joule's heat in driving the OLED 300 is prevented, and the structure of the OLED 300 is not destroyed.

Moreover, since the first compound having the structure of anyone in Chemical Formulae 2 to 4 includes the carbazolyl moiety and dibenzofuranyl/dibenzothiophenyl moieties, each of which includes two benzene rings, the first compound has a HOMO energy level and a LUMO energy level proper for use as the host in the EML 360. Particularly, when the first compound is used together with a delayed fluorescent material and a fluorescent material in the EML 360, it is possible to transfer exciton energy to the fluorescent material without energy loss during the emission process.

In other words, the first compound having the structure of anyone in Chemical Formulae 1 to 4 can be used as the host in the EML 360 of the OLED 300 to enhance luminous efficiency, to lower driving voltage and to improve the luminous life span of the OLED 300. As an example, when the first compound having the structure of anyone in Chemical Formulae 1 to 4 is used as the host in the EML 360, it is possible to minimize exciton quenching owing to an interaction between the exciton in the host and a peripheral polaron and to prevent the luminous life span of the OLED 300 being lowered due to electro-oxidation and photo-oxidation.

Moreover, the first compound having the structure of anyone in Chemical Formulae 1 to 4 has excellent heat resistance property and a large energy level bandgap and high triplet energy level. Accordingly, when the first compound having the structure of anyone in Chemical Formulae 1 to 4 is used as the host in the EML 360, the first compound can transfer efficiently exciton energy to a fluorescent material so that the OLED 300 may have enhanced luminous efficiency. In addition, the first compound in the EML 360 is not deteriorated by heat, so that the OLED 300 having a long life span and excellent color purity can be realized.

The EML 360 includes the second compound which may be the delayed fluorescent material. As described above, each of the excited state of single energy level $S_1^{TD}$ and the excited state triplet energy level $T_1^{TD}$ of the second compound is lower than the corresponding energy levels $S_1^H$ and $T_1^H$ of the first compound (See, FIG. 4). In one exemplary embodiment, the second compound may have, but are not limited to, a triazine core. The second compound having the triazine core may have proper energy levels compared to the first compound having the structure of anyone in Chemical Formulae 1 to 4. As an example, the second compound may include, but are not limited to, an organic compound having the following structure of Chemical Formula 5:

Chemical Formula 5

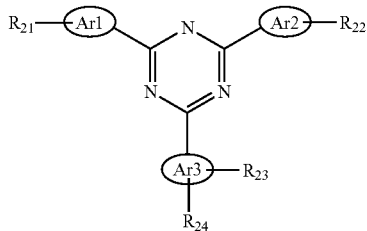

In Chemical Formula 5, each of $R_{21}$ and $R_{22}$ is independently hydrogen, deuterium, tritium, $C_5$~$C_{30}$ aryl group unsubstituted or substituted with at least one of $C_5$~$C_{30}$ aromatic group and hetero aromatic group. $R_{23}$ is hydrogen, deuterium, tritium or cyano group. $R_{24}$ is $C_{10}$~$C_{30}$ hetero aryl group having a carbazolyl moiety or a carbazole moiety, wherein each of the carbazolyl moiety and the carbazole moiety is independently unsubstituted or substituted with at least one of $C_5$~$C_{30}$ aryl group and $C_4$~$C_{30}$ hetero aryl group, respectively, wherein each of the $C_5$~$C_{30}$ aryl group and $C_4$~$C_{30}$ hetero aryl group substituted to each of the carbazole moiety and the carbazolyl moiety is unsubstituted or substituted with phenyl, respectively. Each of $Ar_1$ to $Ar_3$ is independently $C_5$~$C_{30}$ aryl group or $C_4$~$C_{30}$ hetero aryl group.

The second compound having the structure of Chemical Formula 5 includes the triazine moiety, which may act as an electron acceptor, and $R_{24}$ moiety, which may act as an electron donor, separated from the triazine moiety via linker Ar3. Accordingly, the second compound having the structure of Chemical Formula 5 may have delayed fluorescent property. In one exemplary embodiment, the substituents Ar1 and Ar2 of the triazine moiety as well as the linker Ar3 linking the triazine moiety to the $R_{24}$ moiety may be an aromatic ring. As an example, the second compound represented by Chemical Formula 5 may include, but are not limited to, an organic compound having the following structure of Chemical Formula 6:

Chemical Formula 6

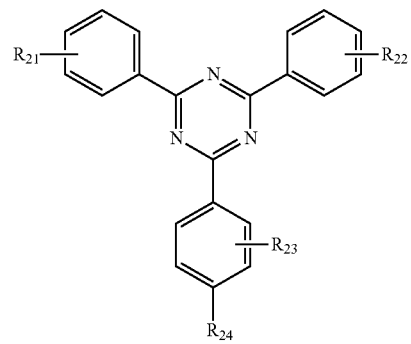

In Chemical Formula 6, each of $R_{21}$ to $R_{24}$ is identical as defined in Chemical Formula 5, respectively.

Particularly, the second compound, which has the delayed fluorescent property and proper energy levels compared to the above-described first compound and the third compound, as described below, may be, but are not limited to, anyone having following structure of Chemical Formula 7:

Chemical Formula 7

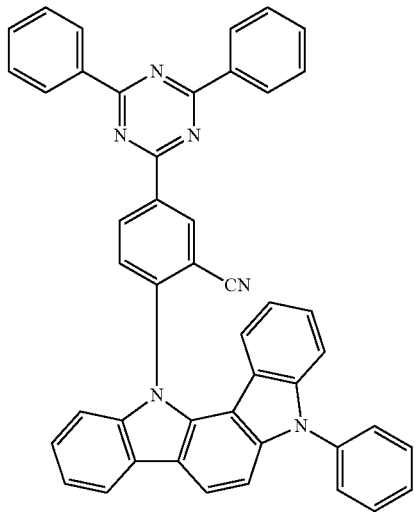

TD-1

-continued

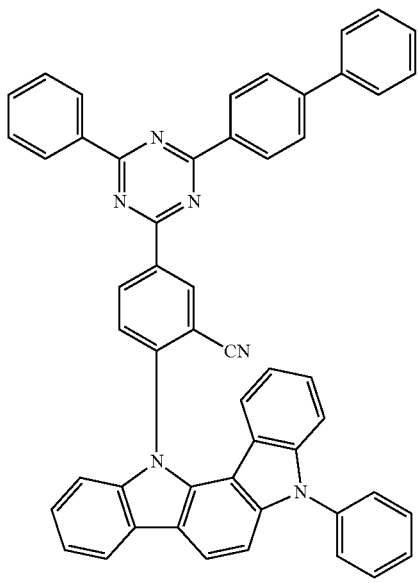

TD-2

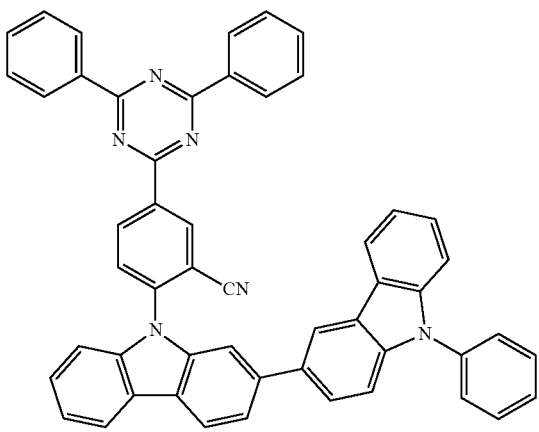

TD-3

Since the delayed fluorescent material can exhibit 100% internal quantum efficiency in theory, it can realize as high luminous efficiency as the conventional phosphorescent material including the heavy metal. However, due to the bond conformation between the electron acceptor-electron donor and the sterical twists in the delayed fluorescent material, an additional charge transfer transition (CT transition) is caused by them. As described above, the delayed fluorescent material is based upon the luminous mechanism, i.e. charge transfer (CT) luminous mechanism. Due to the luminance properties attributed to the CT luminous mechanism, the delayed fluorescent material has limit to be applied to a display device in terms of color purity, because the delayed fluorescent material has a luminescence wavelength having very broad FWHM. In other words, since the delayed fluorescent material such as TADF uses a triplet exciton, it has a short life span and has a limit in terms of color purity because it emits light by CT luminous mechanism and thus has very wide FWHM. In addition, since the delayed fluorescent material utilizes the triplet energy in the emission process, it exhibits short luminous life span.

The hyper-fluorescence for solving the delayed fluorescence utilizes the delayed fluorescent material in order to raise the generation ratio of the singlet exciton of the fluorescent material which utilizes only the singlet exciton. Since the delayed fluorescent material utilizes the triplet energy as well as the singlet energy, when the exciton energy of the delayed fluorescent material is released, the fluorescent material absorbs the energy, and the energy absorbed by the fluorescent material with 100% singlet exciton is used during emission process. Therefore, it is most important that energy transfer between the delayed fluorescent material and the fluorescent material in order to improve luminous efficiency of the OLED including the fluorescent material in which final luminescence occurs.

The EML 360 includes the third compound so as to prevent the OLED including the delayed fluorescent material from being reduced color purity and life span, and thereby realizing the hyper-fluorescence. The third compound has the HOMO energy level satisfying the relationship in Equation (2). Also, each of the excited state singlet energy level $S_1^{FD}$ and the excited state triplet energy level $T_1^{FD}$ of the third compound is less than each of the excited state singlet energy level $S_1^{TD}$ and the excited stated triplet energy level $T_1^{TD}$ of the second compound, respectively. When the energy levels of the third compound satisfies the above-described relationship, the triplet energy of the second compound, which may be the delayed fluorescent material, can be converted to the singlet energy by RISC mechanism, and the converted singlet energy of the delayed fluorescent material can be transferred efficiently to the third compound, which may be the fluorescent material in the EML 360, through Dexter transfer mechanism, which depends upon wave function overlaps among adjacent molecules by inter-molecular electron exchanges and exciton diffusions.

In one exemplary embodiment, the third compound as the fluorescent material has an absorption wavelength ranges having much overlapped regions with an emission wavelength range of the second compound as the delayed fluorescent material. In this case, the exciton energy can be transferred efficiently from the second compound to the third compound, so that the OLED 300 may maximize its luminous efficiency. In addition, the final emission in the EML 360 occurs as the exciton of the third compound drops to the ground state, the third compound includes a compound having narrow FWHM.

In one exemplary embodiment, the third compound as the fluorescent material, may have, but are not limited to, a born-dipyrromethene (BODIPY; 4,4-difluoro-4-bora-3a,4a-diaza-s-indacne) core and/or an quinolino-acridine core. As an example, the third compound as the fluorescent material may include, but are not limited to, a green fluorescent material having the BODIPY core (e.g. LGGD-FD1; LUMO: −3.5 eV; HOMO: −5.8 eV), a compound having the quinolino-acridine core such as 5,12-dimethylquinolino(2,3-b)acridine-7,14(5H, 12H)-dione (LUMO: −3.0 eV; HOMO: −5.4 eV), 5,12-diethylquinolino(2,3-b)acridine-7,14(5H, 12H)-dione (LUMO: −3.0 eV; HOMO: −5.4 eV), 5,12-dibutyl-3,10-difluoroquinolino(2,3-b)acridine-7,14 (5H, 12H)-dione (LUMO: −3.1 eV; HOMO: −5.5 eV), 5,12-dibutyl-3,10-bis(trifluromethyl)quinolino(2,3-b)acridine-7,14(5H, 121H)-dione (LUMO: −3.1 eV; HOMO: −5.5 eV) and combination thereof.

In one exemplary embodiment, the weight ratio of the first compound, which may be the host in the EML 360, is larger than each of the weight ratios of the second and third compounds, each of which may be the dopant in the EML 360. Also, the weight ratio of the second compound may be larger than the weight ratio of the third compound. Alternatively, the weight ratio of the first compound is larger than the weight ratio of the second compound, and the weight ratio of the second compound is larger than the weight ratio of the third compound. As an example, when the weight ratio of the second compound is larger than the weight ratio of the third compound, enough energy can be transferred from the second compound to the third compound via Dexter transfer mechanism.

In an alternative embodiment, the EML 360 may include the first compound of about 60% to about 75% by weight, the second compound of about 20% to about 40% by weight, and the third compound of about 0.1% to about 5% by weight.

In an exemplary embodiment, the EML 360 may be laminated with a thickness of, but are not limited to, about 20 nm to about 100 nm, preferably about 30 nm to about 50 nm.

Returning to FIG. 2, The ETL 370 and the EIL 380 are laminated sequentially between the EML 360 and the second electrode 320. The ETL 370 includes a material having high electron mobility so as to provide electrons stably with the EML 360 by fast electron transportation.

In one exemplary embodiment, the ETL 370 may include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes.

For example, the ETL 370 may include, but are not limited to, tris-(8-hydroxyquinoline aluminum ($Alq_3$), 2-biphenyl-4-yl-5-(4-t-butylphenyl)-1,3,4-oxadiazole (PBD), spiro-PBD, lithium quinolate (Liq), 1,3,5-Tris(N-phenyl-benzimidazol-2-yl)benzene (TPBi), Bis(2-methyl-8-quinolinolato-N1,O8)-(1,1'-biphenyl-4-olato)aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl) 1,3,5-triazine (TmPPPyTz), Poly[9,9-bis(3'-((N,N-dimethyl)-N-ethylammonium)-propyl)-2,7-fluorene]-alt-2,7-(9,9-dioctylfluorene)](PFNBr) and/or tris(phenylquinoxaline) (TPQ).

The EIL 380 is disposed between the second electrode 320 and the ETL 370, and can improve physical properties of the second electrode 320 and therefore, can enhance the life span of the OLED 300. In one exemplary embodiment, the EIL 380 may include, but are not limited to, an alkali halide such as LiF, CsF, NaF, $BaF_2$ and the like, and/or an organic metal compound such as lithium benzoate, sodium stearate, and the like.

In one exemplary embodiment, each of the ETL 370 and the EIL 380 may be respectively laminated with a thickness of, but are not limited to, about 10 nm to about 200 nm, preferably about 10 nm to about 100 nm.

Figure 6:
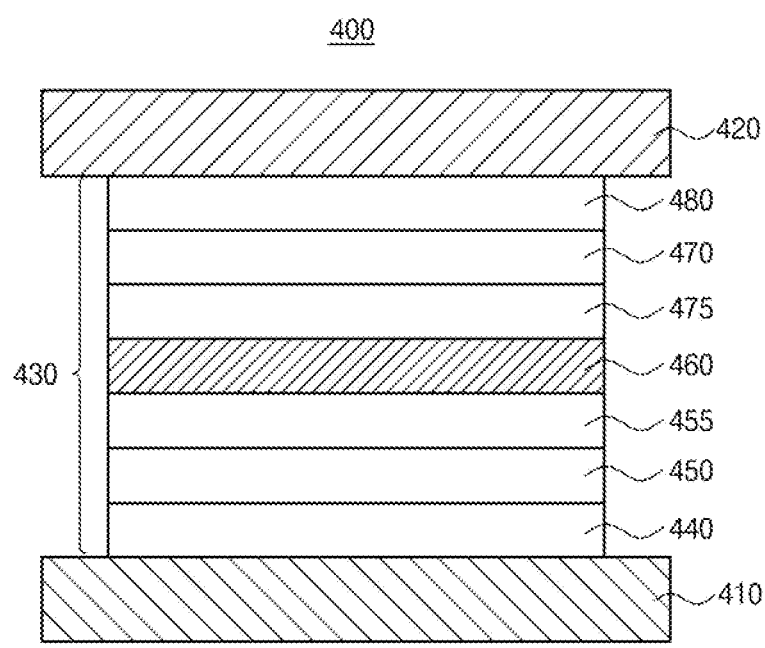
FIG. 6 is a schematic cross-sectional view illustrating an organic light emitting diode in accordance with another exemplary embodiment of the present disclosure.

An OLED may further comprise at least one exciton blocking layers. FIG. 6 is a cross-sectional view illustrating an organic light emitting diode in accordance with another exemplary embodiment of the present disclosure. As illustrated in FIG. 6, the OLED 400 in accordance with the second embodiment of the present disclosure includes first and second electrodes 410 and 420 facing each other and an emitting unit 430 as an emissive layer disposed between the first and second electrodes 410 and 420.

In an exemplary embodiment, the emitting unit 430 includes an HIL 440, an HTL 450, an EML 460, an ETL 470 and an EIL 480 each of which is laminated sequentially above the first electrode 410. Besides, the emitting unit 430 further include a first exciton blocking layer, i.e. an electron blocking layer (EBL) 455 disposed between the HTL 450 and the EML 460 and/or a second exciton blocking layer, i.e., a hole blocking layer (HBL) 475 disposed between the EML 460 and the ETL 470.

As mentioned above, the first electrode 410 may be an anode and include, but is not limited to, a conductive material having a relatively large work function values such as ITO, IZO, SnO, ZnO, ICO, AZO, and the like. The second electrode 420 may be a cathode and may include, but is not limited to, a conductive material having a relatively small work function values such as Al, Mg, Ca, Ag, alloy thereof or combination thereof. Each of the first electrode 410 and the second electrode 420 may be respectively laminated with a thickness of, but are not limited to, about 30 nm to about 300 nm.

The HIL 440 is disposed between the first electrode 410 and the HTL 450. The HIL 440 may include, but is not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 440 may be omitted in compliance with the structure of the OLED 400.

The HTL 450 is disposed adjacent to the EML 260 between the first electrode 410 and the EML 460. The HTL 450 may include, but are not limited to, aromatic amine compounds such as TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine. Each of the HIL 440 and the HTL 450 may be respectively laminated with a thickness of, but are not limited to, of about 5 nm to about 200 nm, preferably about 5 nm to about 10 nm.

The EML 460 may include the first compound, which may be the host, the second compound, which may be the delayed fluorescent material, and the third compound, which may be the fluorescent material. In one exemplary embodiment, each of the excited state singlet energy level $S_1^H$ and the excited state triplet energy level $T_1^H$ of the first compound may be higher than each of the excited state singlet energy level $S_1^{TD}$ and an excited state triplet energy level $T_1^{TD}$ of the second compound, respectively (see, FIG. 4). As an example, the excited state triplet energy level $T_1^H$ of the first compound may be high by at least 0.2 eV compared to the excited state triplet energy level $T_1^{TD}$ of the second compound.

The energy level bandgap $\Delta E_{ST}^H$ between the excited stated singlet energy level $S_1^{TD}$ and the excited state triplet energy level $T_1^{TD}$ of the second compound, which may be the delayed fluorescent material, may be equal to or less than about 0.3 eV in order to realized delayed fluorescence (see, FIG. 3). On the contrary, each of the energy level bandgap $\Delta E_{ST}^H$ between the excited state singlet energy level $S_1^H$ and the excited state triplet energy level $T_1^H$ of the first compound and the energy level bandgap $\Delta E_{ST}^{FD}$ between an excited state singlet energy level $S_1^{FD}$ and an excited state triplet energy level $T_1^{FD}$ of the third compound may be more than about 0.3 eV, respectively.

In addition, each of the excited state singlet energy level $S_1^{TD}$ and the excited state triplet energy level $T_1^{TD}$ of the second compound may be higher than each of the excited state singlet energy level $S_1^{FD}$ and the excited state triplet energy level $T_1^{FD}$ of the third compound, which may the fluorescent material, respectively, in order to transfer exciton energy efficiently from the second compound to the third compound.

Also, the LUMO energy level bandgap $\Delta E^{LUMO}$ between the LUMO energy level $LUMO^H$ of the first compound and the LUMO energy level $LUMO^{TD}$ of the second compound satisfies the relationship in Equation (1) above, and the HOMO energy levels $HOMO^H$, $HOMO^{TD}$ and $HOMO^{FD}$ of the first, second and third compounds satisfy the relationship in Equation (2) above.

Moreover, the energy level bandgap ($|HOMO^H-HOMO^{TD}|$) between the HOMO energy level ($HOMO^H$) of the first compound and the HOMO energy level ($HOMO^{TD}$) of the second compound, or an energy level bandgap ($|LUMO^H-LUMO^{TD}|$) between the LUMO energy level ($LUMO^H$) of the first compound and the LUMO energy level ($LUMO^{TD}$) of the second compound may be equal to or less than about 0.5 eV, for example, between about 0.1 eV to about 0.5 eV.

In one exemplary embodiment, the energy level bandgap $Eg^H$ between the HOMO energy level $HOMO^H$ and the LUMO energy level $LUMO^H$ of the first compound is larger than an energy level bandgap $Eg^{TD}$ between the HOMO energy level $HOMO^{TD}$ and the LUMO energy level $LUMO^{TD}$ of the second compound. Besides, the energy level bandgap $Eg^{TD}$ between the HOMO energy level $HOMO^{TD}$ and the LUMO energy level $LUMO^{TD}$ of the second compound is larger than an energy level bandgap $Eg^{FD}$ between the HOMO energy level $HOMO^{FD}$ and the LUMO energy level $LUMO^{FD}$ of the third compound. When the LUMO energy levels $LUMO^H$ and $LUMO^{TD}$ of the first and second compounds and the HOMO energy levels $HOMO^H$, $HOMO^{TD}$ and $HOMO^{FD}$ of the first, second and third compounds satisfy the relationships in Equations (1) and (2), and/or energy level bandgaps $Eg^H$, $Eg^{TD}$ and $Eg^{FD}$ among the first, second and third compounds satisfy the above-described conditions, the charges can be transported efficiently from the first compound to the third compound via the second compound, so that the EML 360 may maximize its luminous efficiency.

In one exemplary embodiment, the first compound, which can be used as a host, may include, but are not limited to, an organic compound having the structure of anyone in Chemical Formulae 1 to 4. The organic compound having the structure of anyone in Chemical Formulae 1 to 4 has a bi-polar property and excellent heat resistance property owing to its rigid conformational structure. Accordingly, the organic compound is suitable for use as a host of the EML 460.

The second compound may be a delayed fluorescent material, for example, may be, but are not limited to, anyone of the organic compound having the structure of Chemical Formulae 5 to 7. Since the organic compound having the structure of Chemical Formulae 5 to 7 includes an electron acceptor moiety and an electron donor moiety separated from the electron acceptor moiety, it exhibits delayed fluorescence property and has an adequate energy level with respect to the first compound having the structure of Chemical Formulae 1 to 4.

The third compound may be a fluorescent material. Particularly, the third compound may be an organic compound that has an energy level satisfying the relationship in Equation (2) above with respect to the first and second compound and narrow FWHM. In one exemplary embodiment, the third compound may have, but are not limited to, a dipyrromethene (BODIPY) core and/or a quinolino-acridine core. As an example, the third compound may include, but are not limited to, a green fluorescent material having the BODIPY core (LGGD-FD1), a compound having the quinolino-acridine core such as 5,12-dimethylquinolino(2,3-b)acridine-7,14(5H, 12H)-dione, 5,12-diethylquinolino(2,3-b)acridine-7,14(5H, 12H)-dione, 5,12-dibutyl-3,10-difluoroquinolino(2,3-b)acridine-7,14(5H, 12H)-dione 5,12-dibutyl-3,10-bis(trifluromethyl)quinolino(2,3-b)acridine-7,14(5H, 12H)-dione and combination thereof.

As an example, the weight ratio of the first compound, which may be the host in the EML 460, may be larger than each of the weight ratios of the second and third compound, each of which may be the dopant in the EML 460. In addition, the weight ratio of the second compound may be larger than the weight ratio of the third compound.

In an alternative embodiment, the weight ratio of the first compound may be larger than the weight ratio of the second compound, and the weight ratio of the second compound may be larger than the weight ratio of the third compound. As an example, when the weight ratio of the second compound is larger than the weight ratio of the third compound, enough energy can be transferred from the second compound to the third compound via Dexter transfer mechanism. In an alternative embodiment, the EML 460 may include the first compound of about 60% to about 75% by weight, the second compound of about 20% to about 40% by weight, and the third compound of about 0.1% to about 5% by weight.

In an exemplary embodiment, the EML 460 may be laminated with a thickness of, but are not limited to, about 20 nm to about 100 nm, preferably about 30 nm to about 50 nm.

The ETL 470 is disposed between the EML 460 and the EIL 480. As an example, the ETL 470 may include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes. Particularly, the ETL 470 may include, but are not limited to, Alq$_3$, PBD, spiro-PBD, Liq, BAlq, Bphen, NBphen, BCP, TAZ, NTAZ, TaPyPB, TmPPPyTz, PFNBr and/or TPQ.

The EIL 480 is disposed between the second electrode 420 and the ETL 470. In one example, the EIL 480 may include, but are not limited to, an alkali halide such as LiF, CsF, NaF, BaF$_2$ and the likes, and/or an organic metal compound such as lithium benzoate, sodium stearate, and the likes.

In one exemplary embodiment, each of the ETL 470 and the EIL 480 may be respectively laminated with a thickness of, but are not limited to, about 10 nm to about 200 nm, preferably about 10 nm to about 100 nm.

When holes are transferred to the second electrode 420 via the EML 460 and/or electrons are transferred to the first electrode 410 via the EML 460, the OLED 400 may have short lifespan and reduced luminous efficiency. In order to prevent these phenomena, the OLED 400 in accordance with the second embodiment of the present disclosure has at least one exciton blocking layer adjacent to the EML 460.

For example, the OLED 400 of the exemplary embodiment includes the EBL 455 between the HTL 450 and the EML 460 so as to control and prevent electron transfers. In one exemplary embodiment, the EBL 455 may include, but are not limited to. TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, 1,3-Bis(carbazol-9-yl)benzene (mCP), 3,3'-bis(N-carbazolyl)-1,1'-biphenyl (mCBP), CuPc, N,N'-bis[4-

(bis(3-methylphenyl)amino)phenyl]-N,N'-diphenyl-[1,1'-biphenyl]-4,4'-diamine (DNTPD) and/or TDAPB.

In addition, the OLED 400 further includes the HBL 475 as a second exciton blocking layer between the EML 460 and the ETL 470 so that holes cannot be transferred from the EML 460 to the ETL 470. In one exemplary embodiment, the HBL 475 may include, but are not limited to, oxadiazole-based compounds, triazole-based compounds, phenanthroline-based compounds, benzoxazole-based compounds, benzothiazole-based compounds, benzimidazole-based compounds, and triazine-based compounds.

As an example, the EBL 475 may include a compound having a relatively low HOMO energy level compared to the emitting material in EML 460. For example, the HBL 475 may include, but are not limited to, BCP, BAlq, Alq$_3$, PBD, spiro-PBD, Liq, Bis-4,5-(3,5-di-3-pyridylphenyl)-2-methylpyrimidine (B3PYMPM) and combination thereof.

As an example, each of the EBL 455 and the HBL 475 may be respectively laminated with a thickness of, but are not limited to, about 5 nm to about 200 nm, preferably about 10 nm to about 100 nm.

The EML 460 of the OLED 400 in accordance with the second embodiment of the present disclosure includes the first, second and third compounds whose energy levels satisfy the predetermined conditions. Accordingly, it is possible to realize the OLED 400 that enables hyper-fluorescence having excellent luminous efficiency and color purity, reduced driving voltage and improved luminous life span.

In addition, the OLED 400 in accordance with the second embodiment of the present disclosure further includes at least one exciton blocking layers 455 and 475. The luminous efficiency and the life span of the OLED 400 can be further improved by preventing light emission at the interface between the EML 460 and the charge transporting layers 450 and 470, each of which is disposed adjacently to the EML 460.

Figure 7:
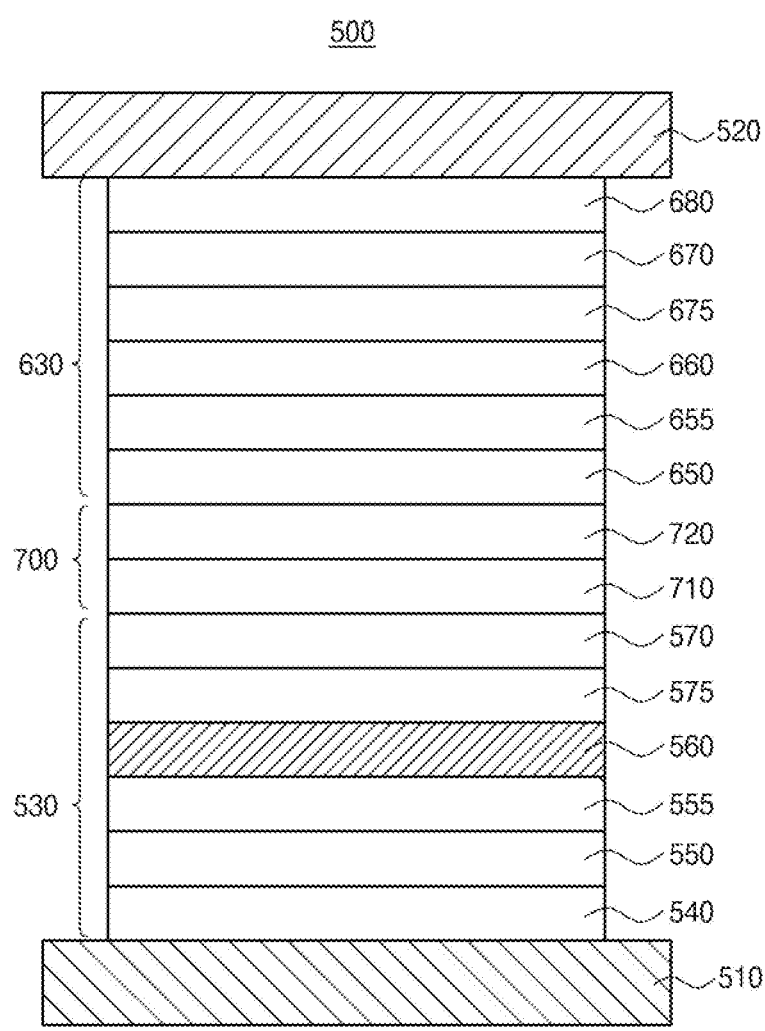
FIG. 7 is a schematic cross-sectional view illustrating an organic light emitting diode in accordance with another exemplary embodiment of the present disclosure.

In the above embodiments, the OLED having only one emitting unit is described. Unlike the above embodiment, the OLED may have multiple emitting units so as to form a tandem structure. FIG. 7 is a cross-sectional view illustrating an organic light emitting diode in accordance with still another embodiment of the present disclosure.

As illustrated in FIG. 7, the OLED 500 in accordance with the third embodiment of the present disclosure includes first and second electrodes 510 and 520 facing each other, a first emitting unit 530 as a first emission layer disposed between the first and second electrodes 510 and 520, a second emitting unit 630 as a second emission layer disposed between the first emitting unit 530 and the second electrode 520, and a charge generation layer 700 disposed between the first and second emitting units 530 and 630.

As mentioned above, the first electrode 510 may be a anode and include, but are not limited to, a conductive material having a relatively large work function values such as ITO, IZO, SnO, ZnO, ICO, AZO, and the likes. The second electrode 520 may be a cathode and may include, but are not limited to, a conductive material having a relatively small work function values such as Al, Mg, Ca, Ag, alloy thereof or combination thereof. Each of the first electrode 510 and the second electrode 520 may be respectively laminated with a thickness of, but are not limited to, about 30 nm to about 300 nm.

The first emitting unit 530 includes a HIL 540, a first HTL (a lower HTL) 550, a first EML (a lower EML) 560 and a first ETL (a lower ETL) 570. The first emitting unit 530 may further include a first EBL (a lower EBL) 555 disposed between the first HTL 550 and the first EML 560 and/or a first HBL (a lower HBL) 575 disposed between the first EML 560 and the first ETL 570.

The second emitting unit 630 includes a second HTL (an upper HTL) 650, a second EML (an upper EML) 660, a second ETL (an upper ETL) 670 and an EIL 680. The second emitting unit 630 may further include a second EBL (an upper EBL) 655 disposed between the second HTL 650 and the second EML 660 and/or a second HBL (an upper HBL) 675 disposed between the second EML 660 and the second ETL 670.

As an example, one of the first EML 560 and the second EML 660 may emit green light and the other of the first EML 560 and the second EML 660 may emit blue and/or red lights. Hereinafter, the OLED 500, where the first EML 560 emit green light and the second EML 660 emit blue and/or red lights, will be described.

The HIL 540 is disposed between the first electrode 510 and the first HTL 550 and improves an interface property between the inorganic first electrode 510 and the organic first HTL 550. In one exemplary embodiment, the HIL 540 may include, but are not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 540 may be omitted in compliance with a structure of the OLED 500.

Each of the first and second HTLs 550 and 650 may include, but are not limited to, TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine, respectively. Each of the HIL 540 and the first and second HTLs 550 and 650 may be respectively laminated with a thickness of, but are not limited to, about 5 nm to about 200 nm, preferably about 5 nm to about 100 nm.

Each of the first ETL 570 and the second ETL 670 facilitates electron transportations in the first emitting unit 530 and the second emitting unit 630, respectively. Each of the first and second ETLs 570 and 670 may include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes, respectively.

As an example, each of the first and second ETLs 570 and 670 may independently include, but are not limited to, Alq$_3$, BAlq, Bphen, NBphen, BCP, TAZ, NTAZ, TaPyPB, TmPP-PyTz, PFNBr and/or TPQ.

The EIL 680 is disposed between the second electrode 520 and the second ETL 570, and can improve physical properties of the second electrode 520 and therefore, can enhance the life span of the OLED 500. In one exemplary embodiment, the EIL 580 may include, but are not limited to, an alkali halide such as LiF, CsF, NaF, BaF$_2$ and the likes, and/or an organic metal compound such as lithium benzoate, sodium stearate, and the likes.

Each of the first and second EBLs 555 and 655 may independently include, but are not limited to, TCTA, Tris [4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD and/or TDAPB.

Each of the first and second HBLs 575 and 675 may independently include, but are not limited to, oxadiazole-based compounds, triazole-based compounds, phenanthroline-based compounds, benzoxazole-based compounds, benzothiazole-based compounds, benzimidazole-based compounds, and triazine-based compounds. Particularly, each of the first and second HBLs 575 and 675 may independently include, but are not limited to, BCP, BAlq, Alq$_3$, PBD, spiro-PBD, Liq, Bis-4,5-(3,5-di-3-pyridylphenyl)-2-methylpyrimidine (B3PYMPM) and combination thereof.

In one exemplary embodiment, when the second EML 660 emits red light, the second EML 660 may be an phosphorescent emitting material layer that includes a host (e.g. CBP and the likes) and a dopant, which may be selected from, but are not limited to Bis(1-phenylisoquinoline)acetylacetonate iridium (PIQIr(acac)), Bis(1-phenylquinoline)acetylacetonate iridium (PQIr(acac)), Tris(1-phneylquinoline)iridium (PQIr), Octaethylporphyrin platinum (PtOEP) and combination thereof. Alternatively, the second EML 660 may be a fluorescent emitting material layer that includes PBD:Eu(DBM)$_3$(phen) (PBD:Tris(dibenzoylmethane) mono(1,10-phenathroline) europium (III), perylene and derivatives thereof as a fluorescent material. In this case, the second EML 660 may emit red light having, but are not limited to, emission wavelength ranges of about 600 nm to about 650 nm.

In another exemplary embodiment, when the second EML 660 emits blue light, the second EML 660 may be a phosphorescent emitting material layer including, but are not limited to, a host (e.g. CBP and the likes) and iridium-based dopants. Alternatively, the second EML 660 may a fluorescent emitting material layer that includes spiro-DPVBi (spiro-4,4'-bis(2,2-diphenylvinyl)biphenyl), spiro-CBP, distyrylbenzene (DSB), distyrylarylene (DSA), polyfluorene (PFO)-based polymers, poly-phenylenevinylene (PPV)-based polymers ant combination thereof as a fluorescent material. Alternatively, the second EML 600 may emit sky blue light or deed blue light as well as blue light. In this case, the second EML 660 may emit blue light having, but are not limited to, emission wavelength ranges of about 440 nm to about 480 nm.

In still another embodiment, the second emitting unit 630 multiple EMLs, for example, blue EML and red EML in order to improve emission efficiency of red light. in this case the EML 660 may emit light having, but are not limited to, emission wavelength ranges of about 440 nm to about 650 nm.

The charge generation layer (CGL) 700 is disposed between the first emitting unit 530 and the second emitting unit 630. The CGL 700 include an N-type CGL 710 disposed adjacently to the first emitting unit 530 and a P-type CGL 720 disposed adjacently to the second emitting unit 630. The N-type CGL 710 injects electrons into the first emitting unit 530 and the P-type CGL 720 injects holes into the second emitting unit 630.

As an example, the N-type CGL 710 may be a layer doped with an alkali metal such as Li, Na, K and/or Cs and/or an alkaline earth metal such as Mg, Sr, Ba and/or Ra. For example, a host used in the N-type CGL 710 may include, but are not limited to, an organic compound such as Bphen or MTDATA. The alkali metal or the alkaline earth metal may be doped by about 0.01 wt % to about 30 wt %.

The P-type CGL 720 may include, but are not limited to, an inorganic material selected from the group consisting of tungsten oxide (WO$_x$), molybdenum oxide (MoO$_x$), beryllium oxide (Be$_2$O$_3$), vanadium oxide (V$_2$O$_5$) and combination thereof, and/or an organic material selected from the group consisting of NPD, HAT-CN, 2,3,5,6-Tetrafluoro-7,7,8,8-tetracyanoquinodimethane (F4TCNQ), TPD, N,N,N',N'-Tetranaphthalenyl-benzidine (TNB), TCTA, N,N'-dioctyl-3,4,9,10-perylenedicarboximide (PTCDI-C8) and combination thereof.

The first EML 560 may include the first compound, which may be the host, the second compound, which may be the delayed fluorescent material, and the third compound, which may be the fluorescent material. In one exemplary embodiment, each of the excited state singlet energy level $S_1^H$ and the excited state triplet energy level $T_1^H$ of the first compound may be higher than each of the excited state singlet energy level $S_1^{TD}$ and an excited state triplet energy level $T_1^{TD}$ of the second compound, respectively (See, FIG. 4). As an example, the excited state triplet energy level $T_1^H$ of the first compound may be high by at least 0.2 eV compared to the excited state triplet energy level $T_{ITD}$ of the second compound.

The energy level bandgap $\Delta E_{ST}^{TD}$ between the excited stated singlet energy level $S_1^{TD}$ and the excited state triplet energy level $T_1^{TD}$ of the second compound, which may be the delayed fluorescent material, may be equal to or less than about 0.3 eV in order to realized delayed fluorescence (see, FIG. 3). On the contrary, each of the energy level bandgap $\Delta E_{ST}^H$ between the excited state singlet energy level $S_1^H$ and the excited state triplet energy level $T_1^H$ of the first compound, which may be the host, and the energy level bandgap $\Delta E_{ST}^{FD}$ between an excited state singlet energy level $S_1^{FD}$ and an excited state triplet energy level $T_1^{FD}$ of the third compound, which may be the fluorescent material, may be more than about 0.3 eV, respectively.

In addition, each of the excited state singlet energy level $S_1^{TD}$ and the excited state triplet energy level $T_1^{TD}$ of the second compound may be higher than each of the excited state singlet energy level $S_1^{FD}$ and the excited state triplet energy level $T_1^{FD}$ of the third compound, which may the fluorescent material, respectively, in order to transfer exciton energy efficiently from the second compound to the third compound.

Also, the LUMO energy level bandgap $\Delta E^{LUMO}$ between the LUMO energy level LUMO$^H$ of the first compound and the LUMO energy level LUMO$^{TD}$ of the second compound satisfies the relationship in Equation (1) above, and the HOMO energy levels HOMO$^H$, HOMO$^{TD}$ and HOMO$^{FD}$ of the first, second and third compounds satisfy the relationship in Equation (2) above.

Moreover, the energy level bandgap (|HOMO$^H$–HOMO$^{TD}$|) between the HOMO energy level (HOMO$^H$) of the first compound and the HOMO energy level (HOMO$^{TD}$) of the second compound, or an energy level bandgap (|LUMO$^H$–LUMO$^{TD}$|) between the LUMO energy level (LUMO$^H$) of the first compound and the LUMO energy level (LUMO$^{TD}$) of the second compound may be equal to or less than about 0.5 eV, for example, between about 0.1 eV to about 0.5 eV.

In one exemplary embodiment, the energy level bandgap Eg$^H$ between the HOMO energy level HOMO$^H$ and the LUMO energy level LUMO$^H$ of the first compound is larger than an energy level bandgap Eg$^{TD}$ between the HOMO energy level HOMO$^{TD}$ and the LUMO energy level LUMO$^{TD}$ of the second compound. Besides, the energy level bandgap Eg$^{TD}$ between the HOMO energy level HOMO$^{TD}$ and the LUMO energy level LUMO$^{TD}$ of the second compound is larger than an energy level bandgap Eg$^{TD}$ between the HOMO energy level HOMO$^{FD}$ and the LUMO energy level LUMO$^{FD}$ of the third compound. When the LUMO energy levels LUMO$^H$ and LUMO$^{TD}$ of the first and second compounds and the HOMO energy levels HOMO$^H$, HOMO$^{TD}$ and HOMO$^{FD}$ of the first, second and third compounds satisfy the relationships in Equations (1) and (2), and/or energy level bandgaps $Eg^H$, $Eg^{TD}$ and $Eg^{FD}$ among the first, second and third compounds satisfy the above-described conditions, the charges can be transported efficiently from the first compound to the third compound via the second compound, so that the EML 360 may maximize its luminous efficiency.

In one exemplary embodiment, the first compound, which can be used as a host, may include, but are not limited to, an organic compound having the structure of anyone in Chemical Formulae 1 to 4. The organic compound having the structure of anyone in Chemical Formulae 1 to 4 has a bi-polar property and excellent heat resistance property owing to its rigid conformational structure. Accordingly, the organic compound is suitable for use as a host of the first EML 560.

The second compound may be a delayed fluorescent material, for example, may be, but are not limited to, anyone of the organic compound having the structure of Chemical Formulae 5 to 7. Since the organic compound having the structure of Chemical Formulae 5 to 7 includes an electron acceptor moiety and an electron donor moiety separated from the electron acceptor moiety, it exhibits delayed fluorescence property and has an adequate energy level with respect to the first compound having the structure of Chemical Formulae 1 to 4.

The third compound may be a fluorescent material. Particularly, the third compound may be an organic compound that has an energy level satisfying the relationship in Equation (2) above with respect to the first and second compound and narrow FWHM. In one exemplary embodiment, the third compound may have, but are not limited to, a dipyrromethene (BODIPY) core and/or a quinolino-acridine core. As an example, the third compound may include, but are not limited to, a green fluorescent material having the BODIPY core (LGGD-FD1), a compound having the quinolino-acridine core such as 5,12-dimethylquinolino(2,3-b)acridine-7,14(5H, 12H)-dione, 5,12-diethylquinolino(2,3-b)acridine-7,14(5H, 12H)-dione, 5,12-dibutyl-3,10-difluoroquinolino(2,3-b)acridine-7,14(5H, 12H)-dione 5,12-dibutyl-3,10-bis(trifluromethyl)quinolino(2,3-b)acridine-7,14(5H, 12H)-dione and combination thereof.

As an example, the weight ratio of the first compound, which may be the host in the first EML 560, may be larger than each of the weight ratios of the second and third compound, each of which may be the dopant in the first EML 560. In addition, the weight ratio of the second compound may be larger than the weight ratio of the third compound.

In an alternative embodiment, the weight ratio of the first compound may be larger than the weight ratio of the second compound, and the weight ratio of the second compound may be larger than the weight ratio of the third compound. As an example, when the weight ratio of the second compound is larger than the weight ratio of the third compound, enough energy can be transferred from the second compound to the third compound via Dexter transfer mechanism. In an alternative embodiment, the EML 460 may include the first compound of about 60% to about 75% by weight, the second compound of about 20% to about 40% by weight, and the third compound of about 0.1% to about 5% by weight.

In an exemplary embodiment, the EML 460 may be laminated with a thickness of, but are not limited to, about 20 nm to about 100 nm, preferably about 30 nm to about 50 nm.

The first EML 560 of the OLED 500 in accordance with the third embodiment of the present disclosure includes the first, second and third compounds whose energy levels satisfy the predetermined conditions. Accordingly, it is possible to realize the OLED 500 that enables hyper-fluorescence having excellent luminous efficiency and color purity, reduced driving voltage and improved luminous life span.

In another exemplary embodiment, an OLED of the present disclosure may further include a third emitting unit disposed between the second emitting unit 630 and the second electrode 520 and a second CGL disposed between the second emitting unit 630 and the third emitting unit. The third emitting material layer may include a third EML. In this case, one of the first EML 560, the second EML 660 and the third EML may include the first, second and third compounds.

Synthesis Example 1: Synthesis of Compound 1

(1) Synthesis of Intermediate 1-1

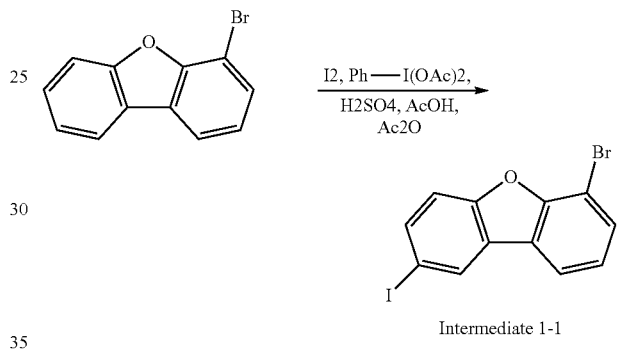

Intermediate 1-1

10.0 g (40.65 mmol) of 4-bromo dibenzofuran, 5.1 g (20.32 mmol) of iodine and 6.6 g (20.32 mmol) of phenyl iodide diacetate were placed in a mixed solvent of 150 mL of acetic acid and 150 mL of acetic anhydride under nitrogen atmosphere. Three drops of sulfuric acid were added in the solution and then stirred 10 hours at room temperature. After the reaction was completed, ethyl acetate was added into the mixed solution, and then the solution was washed with water and organic layer was separated from aqueous layer. Anhydrous magnesium sulfate was added to the organic solution and the solution was stirred again. After the solution was filtered with silica pad, the solution was concentrated under reduced pressure and purified by column chromatography to give an Intermediate 1-1 (yield: 65%).

(2) Synthesis of Intermediate 1-2

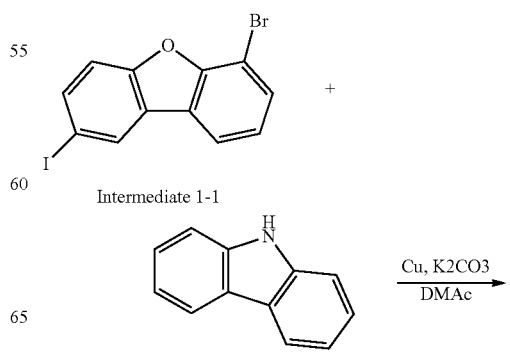

Intermediate 1-1

-continued

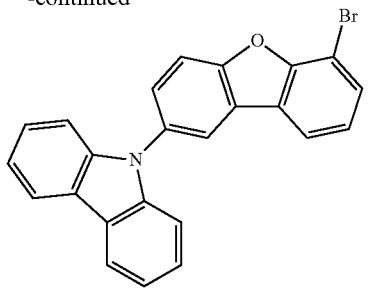

Intermediate 1-2

9.8 g (26.35 mmol) of Intermediate 1-1, 2.2 g (13.18 mmol) of carbazole, 2 g (32.53 mmol) of copper powder and 3.6 g (26.36 mmol) of potassium carbonate was added into 70 mL of dimethyl acetoamide, and the solution was stirred for 24 hours at 130° C. After the reaction was completed, the temperature was dropped to room temperature. The solution was filtered with silica pad to remove copper powder. The obtained solution was washed with water to separate an organic layer from aqueous layer. Anhydrous magnesium sulfate was added into the organic solution and the solution was stirred again. After the solution was filtered with silica pad, the solution was concentrated under reduced pressure and purified by column chromatography to give an Intermediate 1-2 (yield: 78%).

(3) Synthesis of Compound 1

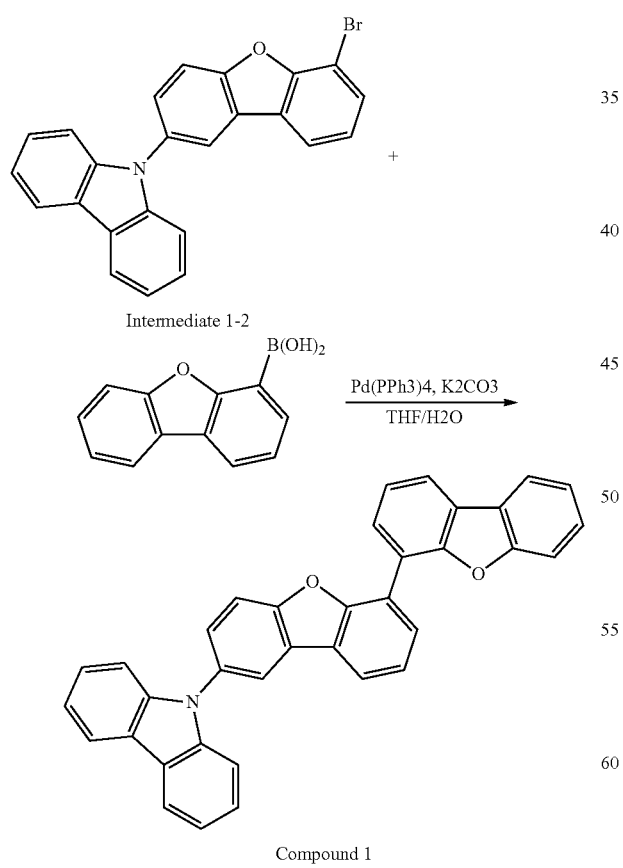

Compound 1 g (20.43 mmol) of Intermediate 1-2, 4.76 g (22.47 mmol) of dibenzo[b,d]furan-4-yl-boronic acid and 2 mol % of Tetrakis(triphenylphosphine) palladium (Pd(PPh$_3$)$_4$) was added into 50 mL of Tetrahydrofuran. 40.86 mmol of potassium carbonate was dissolved in 25 mL of water and the aqueous solution was mixed with the organic solution. The mixed solution was stirred for 12 hours at 80° C. After the reaction was completed, and then the temperature was dropped to room temperature to separate an organic layer from an aqueous layer. Anhydrous magnesium sulfate was added into the organic solution and the organic solution was stirred again. After the organic solution was filtered with silica pad, the solution was concentrated under reduced pressure and purified by column chromatography to give Compound 1 (yield: 60%).

Synthesis Example 2: Synthesis of Compound 2

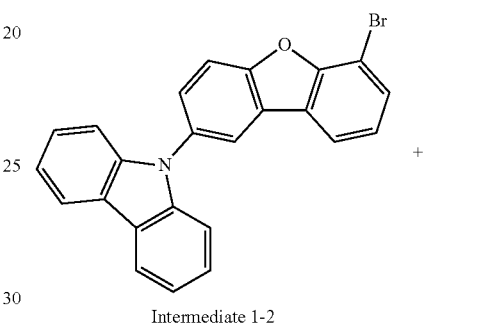

Intermediate 1-2

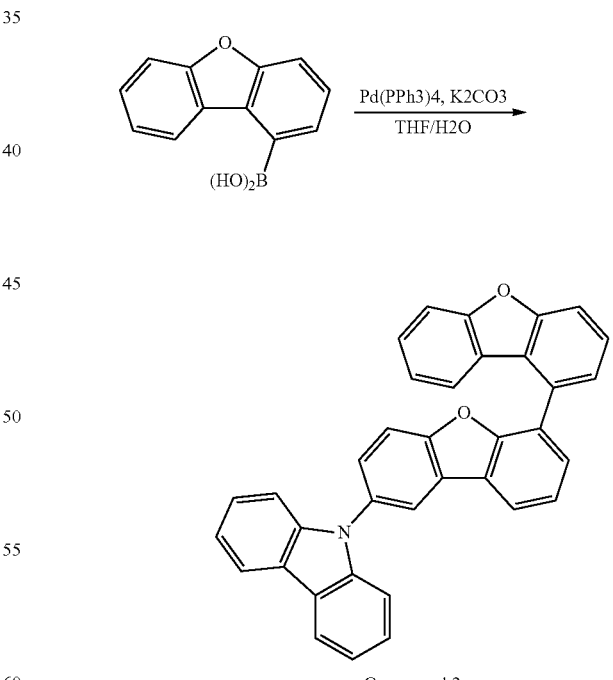

Compound 2

Synthetic reaction was performed as the same process and condition as Example 1 except that 8.4 g (20.43 mmol) of Intermediated 1-2 and 4.76 g (22.47 mmol) of dibenzo[b,d]furan-1-yl-bornic acid were used as reactants to give Compound 2 (yield: 57%).

Synthesis Example 3: Synthesis of Compound 3

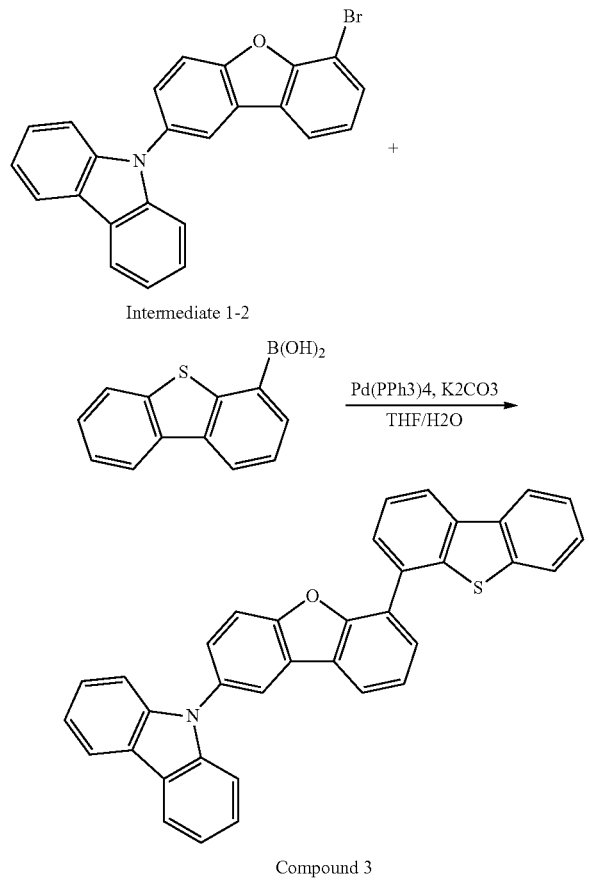

Intermediate 1-2

Compound 3

Synthetic reaction was performed as the same process and condition as Example 1 except that 8.4 g (20.43 mmol) of Intermediated 1-2 and 5.12 g (22.47 mmol) of dibenzo[b,d]thiophen-4-yl-bornic acid were used as reactants to give Compound 3 (yield: 62%).

Synthesis Example 4: Synthesis of Compound 4

(1) Synthesis of Intermediate 4-1

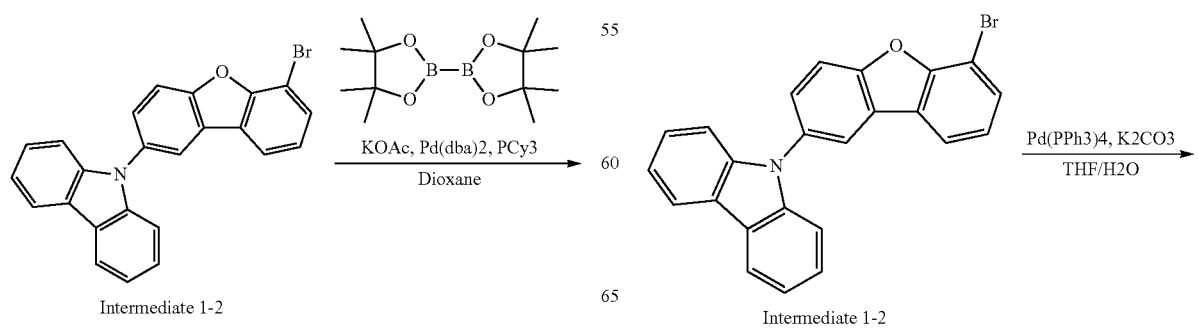

Intermediate 1-2

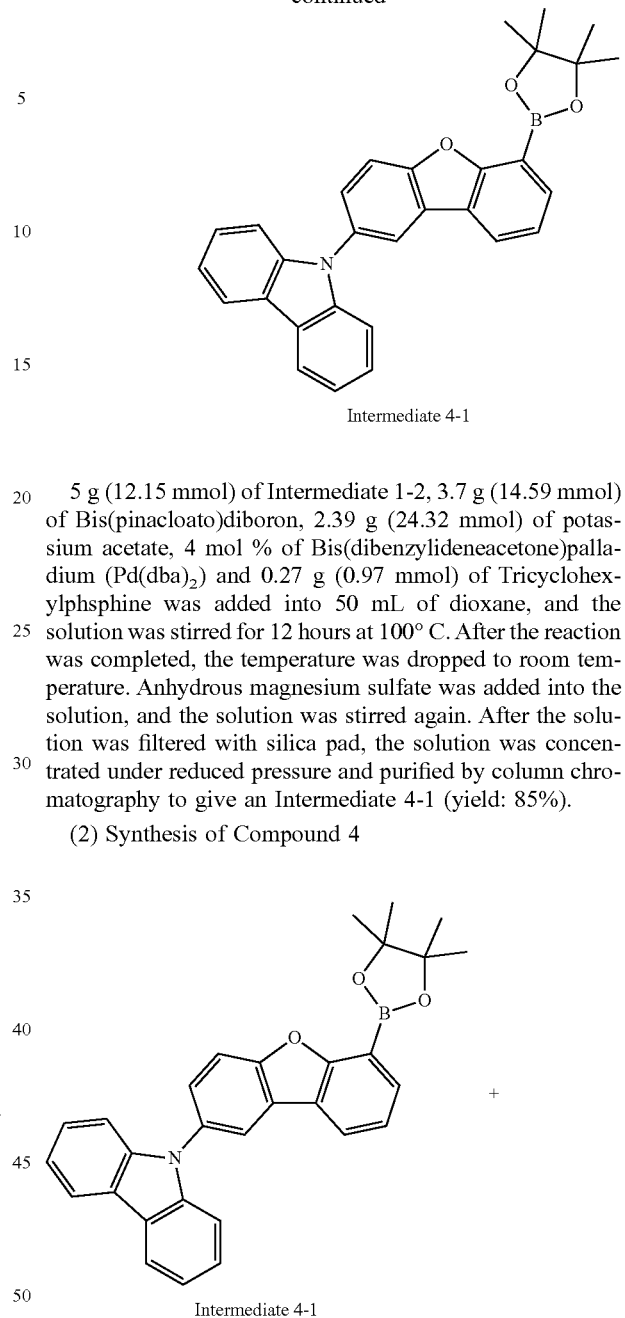

Intermediate 4-1

5 g (12.15 mmol) of Intermediate 1-2, 3.7 g (14.59 mmol) of Bis(pinacloato)diboron, 2.39 g (24.32 mmol) of potassium acetate, 4 mol % of Bis(dibenzylideneacetone)palladium (Pd(dba)₂) and 0.27 g (0.97 mmol) of Tricyclohexylphsphine was added into 50 mL of dioxane, and the solution was stirred for 12 hours at 100° C. After the reaction was completed, the temperature was dropped to room temperature. Anhydrous magnesium sulfate was added into the solution, and the solution was stirred again. After the solution was filtered with silica pad, the solution was concentrated under reduced pressure and purified by column chromatography to give an Intermediate 4-1 (yield: 85%).

(2) Synthesis of Compound 4

Intermediate 4-1

113

-continued

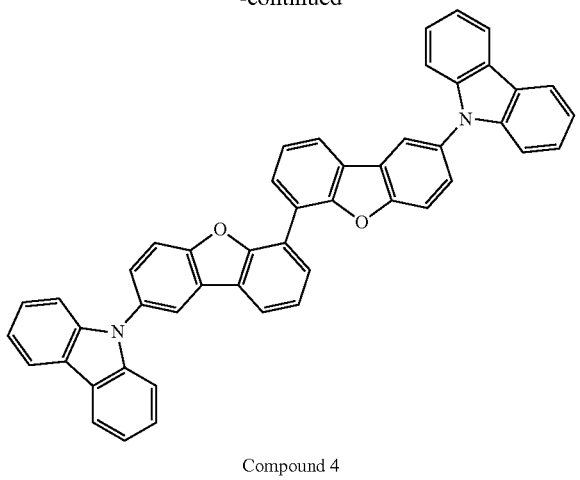

Compound 4

Synthetic reaction was performed as the same process and condition as Example 1 except that 4.75 g (10.34 mmol) of Intermediated 4-1 and 4.25 g (10.34 mmol) of Intermediate 1-2 were used as reactants to give Compound 4 (yield: 70%).

Synthesis Example 5: Synthesis of Compound 5

(1) Synthesis of Intermediate 5-1

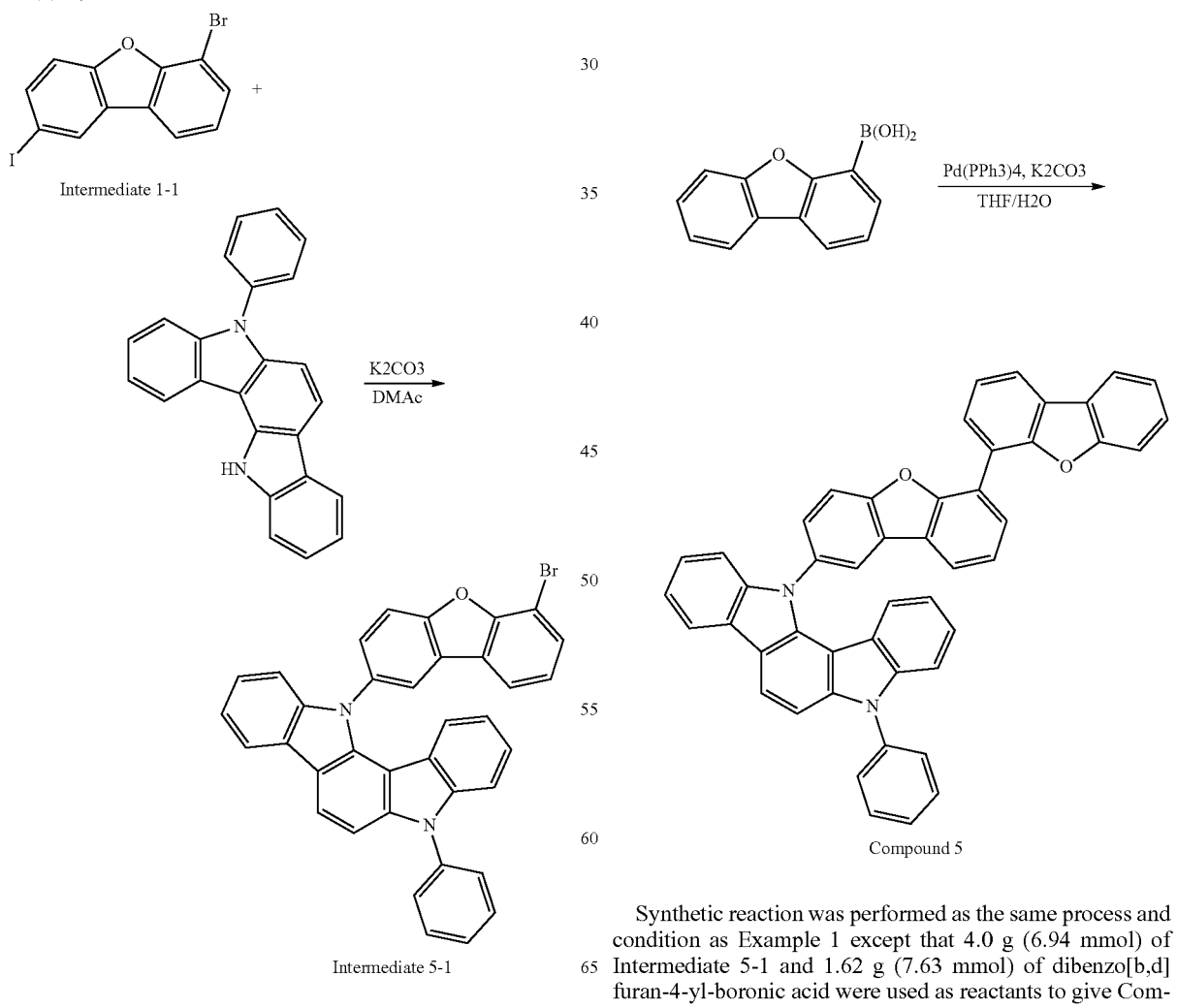

Intermediate 1-1

Intermediate 5-1

Intermediate 5-1

114

Synthetic reaction was performed as the same process and condition as the reaction scheme of synthesizing the Intermediate 1-2 in Example 1 except that 5.0 g (13.45 mmol) of Intermediate 1-1 and 4.47 g (13.45 mmol) of 5-phenyl-5,12-dihydroindolo[3,2-a]carbazole (CAS Registration No: 1247053-55-9) were used as reactants to give Intermediate 5-1 (yield: 51%).

(2) Synthesis of Compound 5

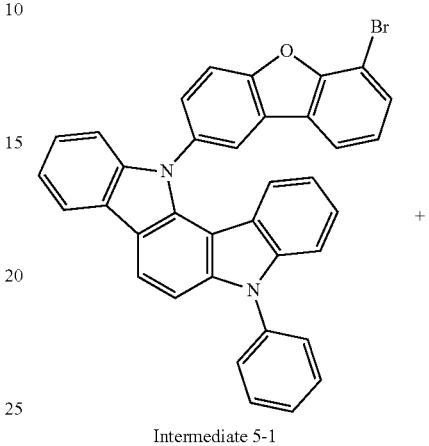

Compound 5

Synthetic reaction was performed as the same process and condition as Example 1 except that 4.0 g (6.94 mmol) of Intermediate 5-1 and 1.62 g (7.63 mmol) of dibenzo[b,d]furan-4-yl-boronic acid were used as reactants to give Compound 5 (yield: 64%).

Synthesis Example 6: Synthesis of Compound 6

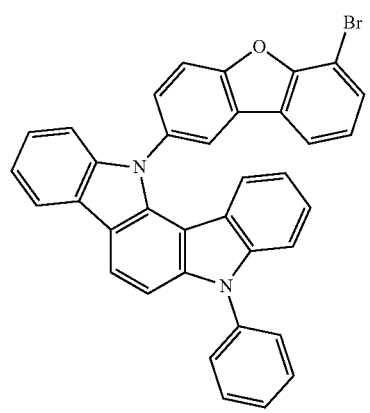

Intermediate 5-1

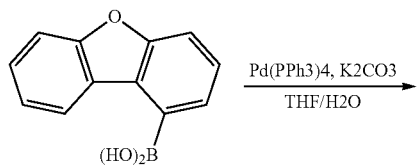

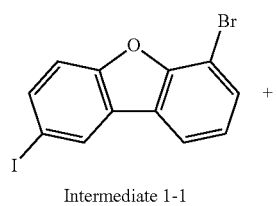

Compound 6

Synthetic reaction was performed as the same process and condition as Example 1 except that 4.0 g (6.94 mmol) of Intermediate 5-1 and 1.62 g (7.63 mmol) of dibenzo[b,d]furan-1-yl-boronic acid were used as reactants to give Compound 6 (yield: 60%).

Synthesis Example 7: Synthesis of Compound 7

(1) Synthesis of Intermediate 7-1

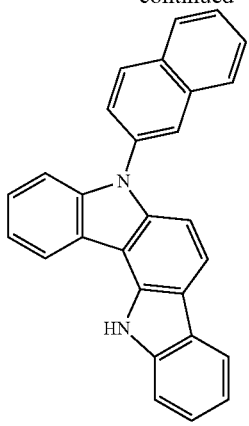

Intermediate 1-1

-continued

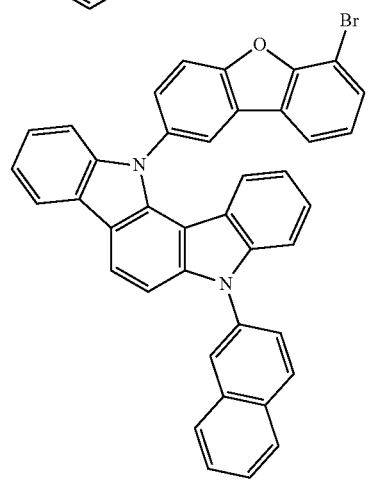

Intermediate 7-1

Synthetic reaction was performed as the same process and condition as the reaction scheme of synthesizing the Intermediate 1-2 in Example 1 except that 5.0 g (13.45 mmol) of Intermediate 1-1 and 5.14 g (13.45 mmol) of 5-(naphthalene-2-yl)-5,12-dihydroinodolo[3,2-a]carbazole were used as reactants to give an Intermediate 7-1 (yield: 57%).

(2) Synthesis of Compound 7

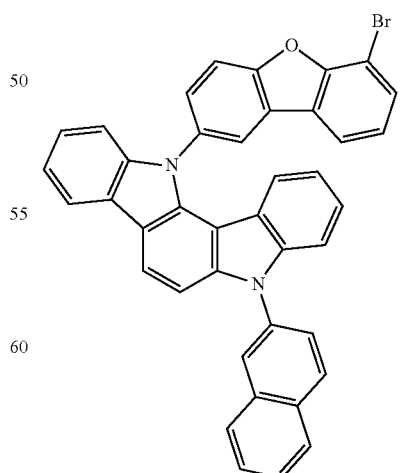

Intermediate 7-1

117

-continued

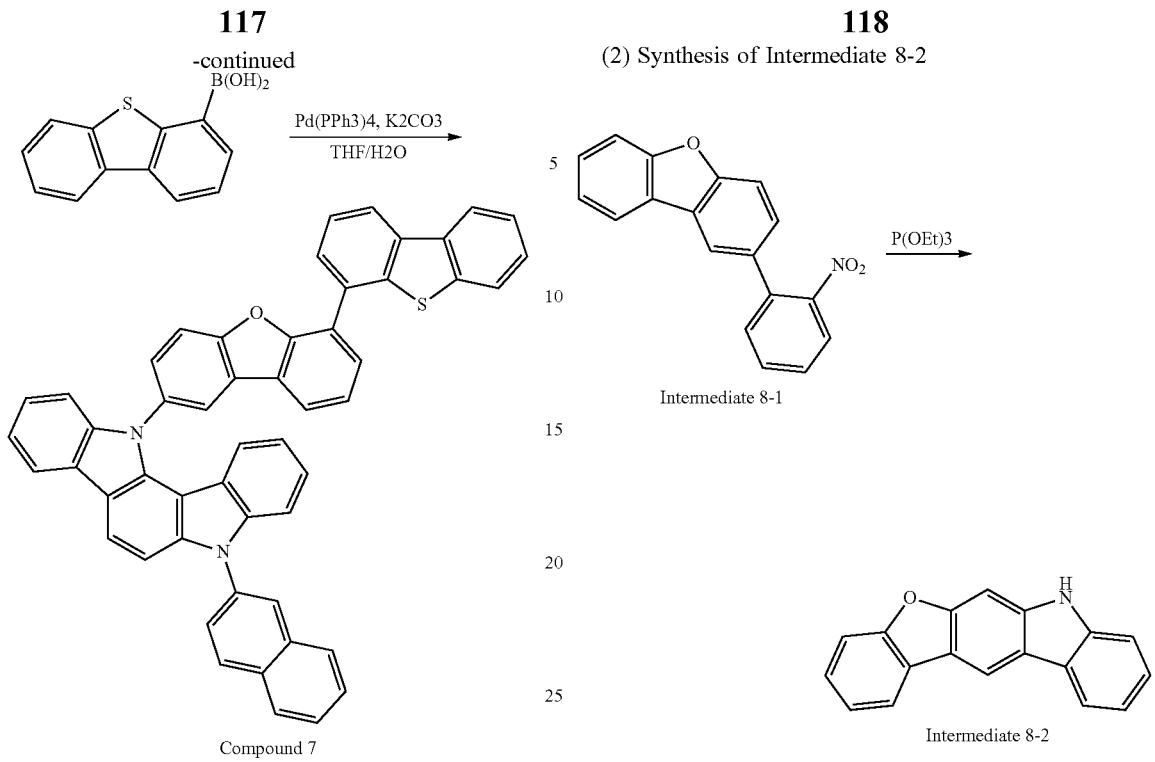

Compound 7

Synthetic reaction was performed as the same process and condition as Example 1 except that 4.8 g (7.67 mmol) of Intermediate 7-1 and 1.92 g (8.44 mmol) of dibenzo[b,d]thiophene-4-yl-boronic acid were used as reactants to give Compound 7 (yield: 60%).

Synthesis Example 8: Synthesis of Compound 8

(1) Synthesis of Intermediate 8-1

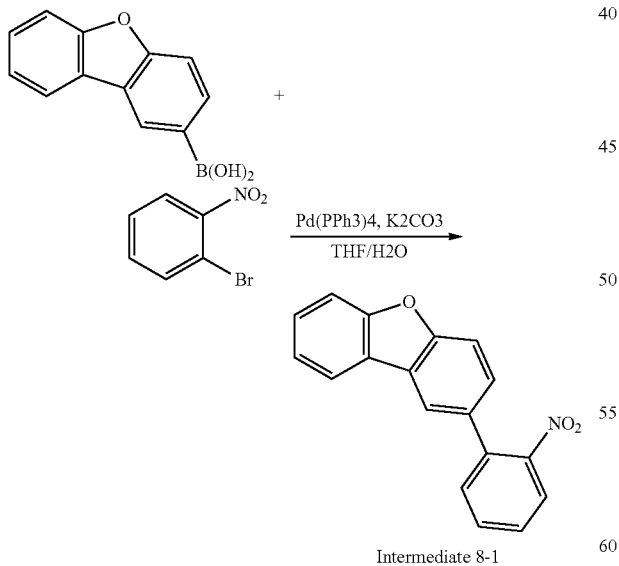

Synthetic reaction was performed as the same process and condition in Example 1 except that 10.0 g (47.16 mmol) of dibenzo[b,d]furan-2-yl-boronic acid and 9.48 g (47.16 mmol) of 1-bromo-2-nitorbenzne were used as reactants to give an Intermediate 8-1 (yield: 78%).

118

(2) Synthesis of Intermediate 8-2

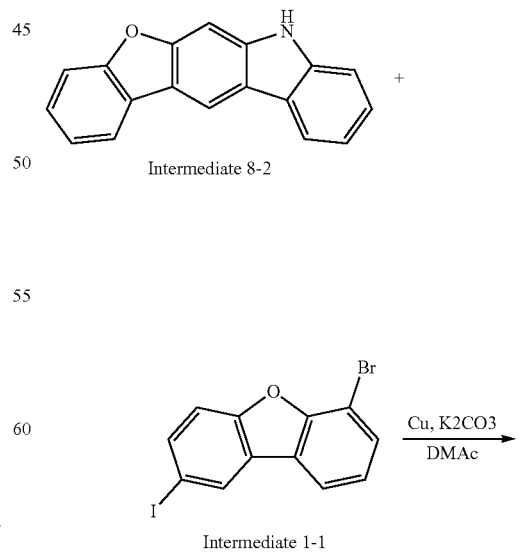

10.6 g (36.78 mmol) of Intermediated 8-1 was added into 90 mL of triethyl phosphate, and the solution was refluxed and stirred for 10 hours. The temperature was cooled and concentrated under reduced pressure. The solution was washed with water and extracted with ethyl acetate to separate an organic layer from an aqueous layer. Anhydrous magnesium sulfate was added into the organic solution and the solution was stirred again. The organic solution was filtered with silica pad, concentrated under reduced pressure and purified by column chromatography to give an Intermediate 8-2 (yield: 66%).

(3) Synthesis of Intermediate 8-3

119
-continued

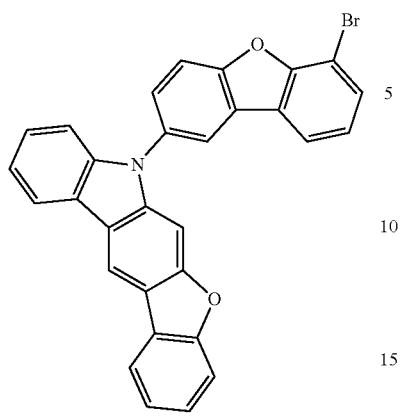
Intermediate 8-3

120
-continued

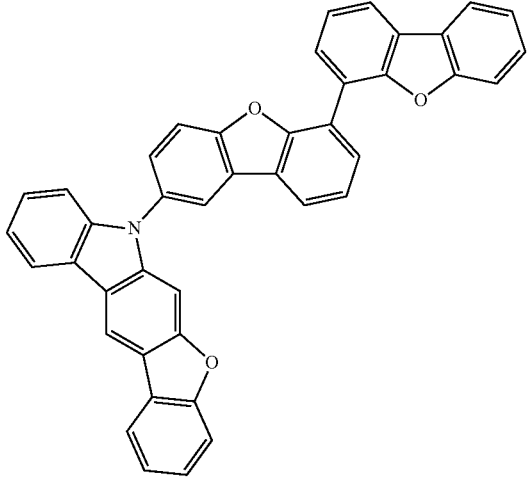
Compound 8

Synthetic reaction was performed as the same process and condition as the reaction scheme of synthesizing the Intermediated 1-2 in Example 1 except that 6.24 g (24.27 mmol) of Intermediate 8-2 and 9.02 g (24.27 mmol) of Intermediate 1-1 were used as reactants to give an Intermediate 8-3 (yield: 55%).

(4) Synthesis of Compound 8

Synthetic reaction was performed as the same process and condition in Example 1 except that 6.69 g (13.35 mmol) of Intermediate 8-3 and 3.12 g (14.69 mmol) of dibenzo[b,d]-furan-4-yl-boronic acid were used as reactants to give Compound 8 (yield: 72%).

Synthesis Example 9: Synthesis of Compound 9

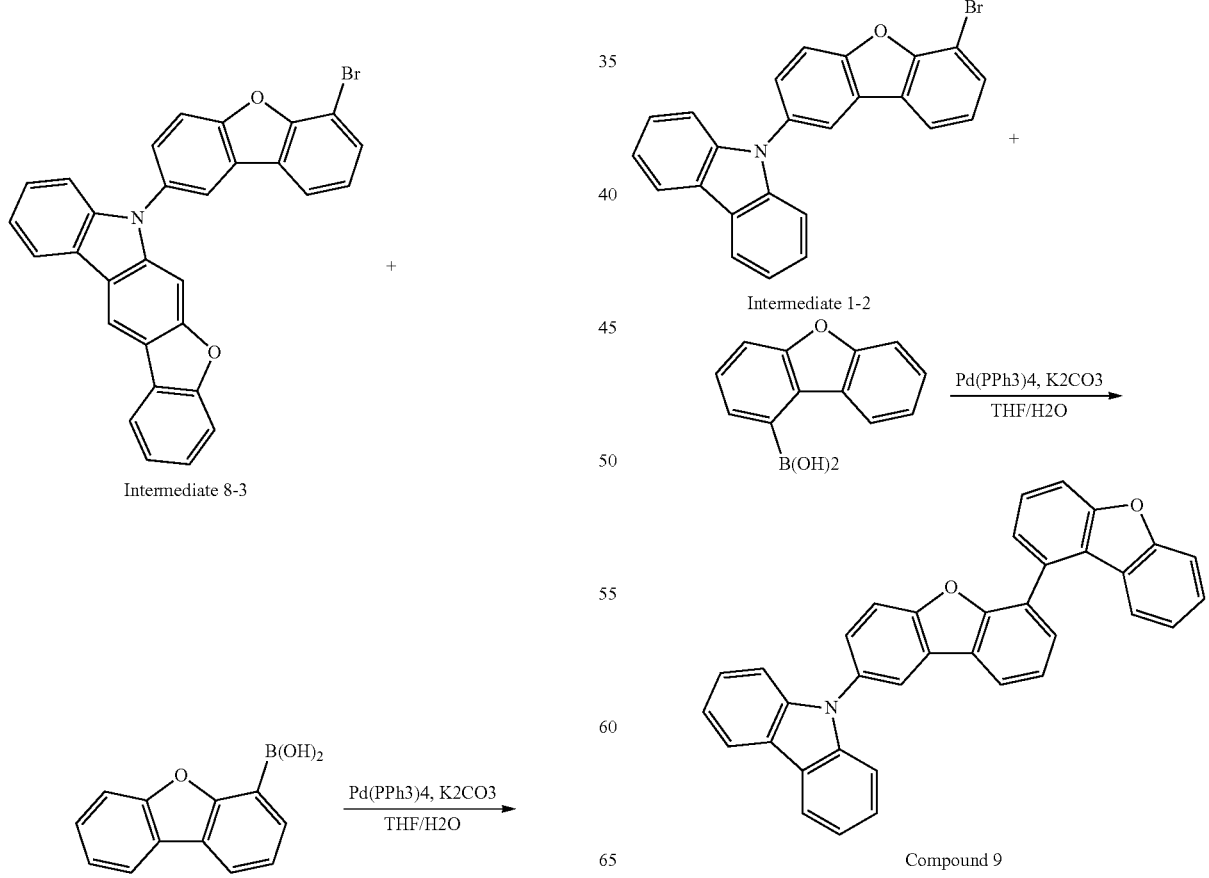

Synthetic reaction was performed as the same process and condition as Example 1 except that 8.4 g (20.43 mmol) of Intermediate 1-2 and 4.76 g (22.47 mmol) of dibenzo[b,d]furan-1-yl-boronic acid were used as reactants to give Compound 9 (yield: 57%). Experimental Example 1: Measurement of Energy Levels of Organic Compound LUMO energy levels and HOMO energy levels were measured each for the Compounds 1, 4 and 9 (hereinafter, referred as "TH-1", "TH-2" and "TH-3", respectively), each of which can be used as the host, TD-1, TD-2 and TD-3 in Chemical Formula 7, each of which is delayed fluorescent material), and green fluorescent material (LGGD-FD1), which has a boron-dipyrromethene core and is fluorescent material). Also, HOMO energy levels and LUMO energy levels were measured for the reference compounds "RTH and "RTD" as indicated below. Table 1 indicates the measurement results.

[Reference Compound]

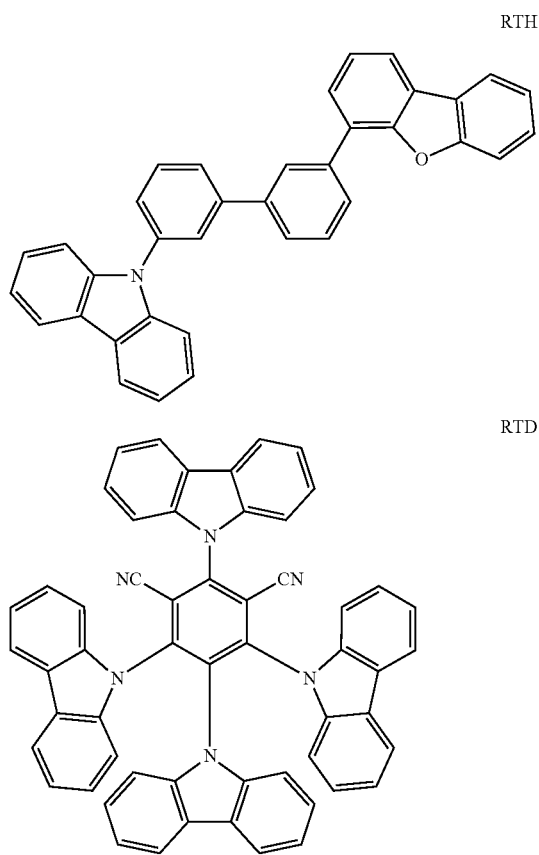

RTH

RTD

TABLE 1

Energy Level of Organic Compounds

| Compounds | HOMO (eV) | LUMO (eV) | Eg (eV) |
|---|---|---|---|
| TH-1 | −5.9 | −2.5 | 3.4 |
| TH-2 | −6.0 | −2.6 | 3.4 |
| TH-3 | −5.8 | −2.3 | 3.5 |
| TD-1 | −5.8 | −3.2 | 2.6 |
| TD-2 | −6.0 | −3.3 | 2.7 |
| TD-3 | −6.0 | −3.4 | 2.6 |

TABLE 1-continued

Energy Level of Organic Compounds

| Compounds | HOMO (eV) | LUMO (eV) | Eg (eV) |
|---|---|---|---|
| FD | −5.8 | −3.5 | 2.3 |
| RTH | −5.8 | −2.2 | 3.6 |
| RTD | −6.0 | −3.4 | 2.6 |

HOMO: Film (100 nm/ITO), by AC3;
LUMO: Calculated at Film absorption edge;
Eg: LUMO − HOMO Example 1: Manufacture of Organic Light Emitting Diode (OLED)

An organic light emitting diode was manufactured using "TH-1" as a host ($1^{st}$ compound), "TD-1" as a delayed fluorescent material ($2^{nd}$ compound), and "FD" as a fluorescent dopant ($3^{rd}$ compound) in the EML. An energy level bandgap between LUMO energy level of "TH-1" and LUMO energy level of "TD-1" is 0.7 eV. HOMO energy level of "TH-1" is less than HOMO energy level of "TD-1" and HOMO energy level of "TD-1" is less than HOMO energy level of "FD".

A glass substrate, to which ITO electrode (including a reflective plate) was attached and which has a size of 40 nm×40 nm×0.5 mm, was washed by ultra-sonication using isopropyl alcohol, acetone and DI (distilled water) as a cleaning solvent for 5 minutes and dried in an oven at 100° C. After cleaning the substrate, the substrate was treated $O_2$ plasma for 2 minutes and was transferred to a vacuum chamber for depositing emitting layer. Subsequently, an emitting layer and a cathode were deposited by evaporation from a heating boat under $10^{-7}$ Torr vacuum condition as the following order: A hole injection layer (HIL) (HAT-CN; 10 nm); a hole transport layer (HTL) (NPB, 75 nm); an electron blocking layer (EBL) (mCBP; 15 nm); an emitting material layer (EML) (TH-1 69.5 wt %, TD-1 30 wt %, and FD 0.5 wt %; 35 nm); a hole blocking layer (HBL) (B3PYMPM; 10 nm); an electron transport layer (ETL) (TPBi; 20 nm); an electron injection layer (EIL) (LiF; 80 nm); and a cathode (Al; 100 nm).

And then, cappling layer (CPL) was deposited over the cathode and the device was encapsualted by glass. After deposition of emissive layer and the cathode, the OLED was transferred from the deposition chamber to a dry box for film formation, followed by encapsulation using UV-curable epoxy and moisture getter. The manufacture organic light emitting diode had an emission area of 9 $mm^2$.

Example 2: Manufacture of OLED

An OLED was manufactured as the same process and the same material as Example 1, except that "TH-2" as a host and "TD-1" as a delayed fluorescent material in the EML were used. An energy level bandgap between LUMO energy level of "TH-2" and LUMO energy level of "TD-1" is 0.6 eV. HOMO energy level of "TH-2" is less than HOMO energy level of "TD-2" and HOMO energy level of "TD-2" is less than HOMO energy level of "FD".

Example 3: Manufacture of OLED

An OLED was manufactured as the same process and the same material as Example 1, except that "TH-2" as a host and "TD-2" as a delayed fluorescent material in the EML were used. An energy level bandgap between LUMO energy level of "TH-2" and LUMO energy level of "TD-2" is 0.7 eV. HOMO energy level of "TH-2" is the same as HOMO energy level of "TD-2" and HOMO energy levels of "TH-2" and "TD-2" are less than HOMO energy level of "FD".

Comparative Example 1: Manufacture of OLED

An OLED was manufactured as the same process and the same material as Example 1, except that "RTH" as a host (70 wt %) and "RTD" as a delayed fluorescent material (30 wt %) without FD in the EML were used (Ref. 1). An energy level bandgap between LUMO energy level of "RTH" and LUMO energy level of "RTD" is 1.2 eV. HOMO energy level of "RTH" is more than HOMO energy level of "RTD".

Comparative Example 2: Manufacture of OLED

An OLED was manufactured as the same process and the same material as Example 1, except that "RTH" as a host (70 wt %) and "TD-1" as a delayed fluorescent material (30 wt %) without FD in the EML were used (Ref. 2). An energy level bandgap between LUMO energy level of "RTH" and LUMO energy level of "TD-1" is 1.0 eV. HOMO energy level of "RTH" is the same as HOMO energy level of "TD-1".

Comparative Example 3: Manufacture of OLED

An OLED was manufactured as the same process and the same material as Example 1, except that "RTH" as a host and "RTD" as a delayed fluorescent material in the EML were used (Ref. 3). An energy level bandgap between LUMO energy level of "RTH" and LUMO energy level of "RTD" is 1.2 eV. HOMO energy level of "RTH" is more than HOMO energy level of "RTD". In addition, HOMO energy level of "FD" is more than HOMO energy level of "RTD".

Comparative Example 4: Manufacture of OLED

An OLED was manufactured as the same process and the same material as Example 1, except that "TH-1" as a host and "RTD" as a delayed fluorescent material in the EML were used (Ref. 4). An energy level bandgap between LUMO energy level of "TH-1" and LUMO energy level of "RTD" is 0.9 eV. HOMO energy level of "TH-1" is more than HOMO energy level of "RTD". In addition, HOMO energy level of "FD" is more than HOMO energy level of "RTD".

Comparative Example 5: Manufacture of OLED

An OLED was manufactured as the same process and the same material as Example 1, except that "TH-3" as a host and "TD-1" as a delayed fluorescent material in the EML were used (Ref. 5). An energy level bandgap between LUMO energy level of "TH-3" and LUMO energy level of "TD-1" is 0.9 eV. HOMO energy level of "TH-3" is the same as HOMO energy level of "TD-1". In addition, HOMO energy level of "FD" is the same as HOMO energy level of "TD-1".

Comparative Example 6: Manufacture of OLED

An OLED was manufactured as the same process and the same material as Example 1, except that "TH-1" as a host and "TD-2" as a delayed fluorescent material in the EML were used (Ref. 6). An energy level bandgap between LUMO energy level of "TH-1" and LUMO energy level of "TD-2" is 0.8 eV. HOMO energy level of "TH-1" is more than HOMO energy level of "TD-2". In addition, HOMO energy level of "FD" is more than HOMO energy level of "TD-2".

Comparative Example 7: Manufacture of OLED

An OLED was manufactured as the same process and the same material as Example 1, except that "TH-3" as a host and "TD-2" as a delayed fluorescent material in the EML were used (Ref. 7). An energy level bandgap between LUMO energy level of "TH-3" and LUMO energy level of "TD-2" is 1.0 eV. HOMO energy level of "TH-3" is more than HOMO energy level of "TD-2". In addition, HOMO energy level of "FD" is more than HOMO energy level of "TD-2".

Comparative Example 8: Manufacture of OLED

An OLED was manufactured as the same process and the same material as Example 1, except that "TH-1" as a host and "TD-3" as a delayed fluorescent material in the EML were used (Ref. 8). An energy level bandgap between LUMO energy level of "TH-1" and LUMO energy level of "TD-3" is 0.9 eV. HOMO energy level of "TH-1" is more than HOMO energy level of "TD-3". In addition, HOMO energy level of "FD" is more than HOMO energy level of "TD-3".

Comparative Example 9: Manufacture of OLED

An OLED was manufactured as the same process and the same material as Example 1, except that "TH-2" as a host and "TD-3" as a delayed fluorescent material in the EML were used (Ref. 9). An energy level bandgap between LUMO energy level of "TH-2" and LUMO energy level of "TD-3" is 0.8 eV. HOMO energy level of "TH-2" the same as HOMO energy level of "TD-3". In addition, HOMO energy level of "FD" is more than HOMO energy level of "TD-3".

Comparative Example 10: Manufacture of OLED

An OLED was manufactured as the same process and the same material as Example 1, except that "TH-3" as a host and "TD-3" as a delayed fluorescent material in the EML were used (Ref. 10). An energy level bandgap between LUMO energy level of "TH-3" and LUMO energy level of "TD-3" is 1.1 eV. HOMO energy level of "TH-3" is more than HOMO energy level of "TD-3". In addition, HOMO energy level of "FD" is more than HOMO energy level of "TD-3".

Experimental Example 2: Measurement of Luminous Properties of OLED

Each of the OLED manufactured in Examples 1 to 3 and Ref. 1 to 10 was connected to an external power source, and luminous properties of all the diodes were evaluated using a constant current source (KEITHLEY) and a photometer PR650 at room temperature. In particular, driving voltage (V), current efficiency (cd/A), power efficiency (lm/W), external quantum efficiency (EQE; %), color coordinates, maximum electro-luminescence ($\lambda_{max}$; nm) and FWHM at a current density of 10 mA/cm$^2$ and luminous life span, i.e. a time period until brightness is reduced to 95% at 3000 nit of the OLED were measured. The measurement results thereof are indicated in the following Table 2.

TABLE 2

Luminous Properties of OLED

|  | [V] | cd/A | lm/W | EQE [%] | CIEx | CIEy | $\lambda_{max}$ [nm] | FWHM [nm] | T95 @3000 nit |
|---|---|---|---|---|---|---|---|---|---|
| Ref. 1 | 5.0 | 50 | 38.16 | 17.42 | 0.34 | 0.59 | 532 | 84 | 300 |
| Ref. 2 | 4.7 | 53 | 41.98 | 16.49 | 0.33 | 0.57 | 540 | 97 | 400 |
| Ref. 3 | 4.9 | 52 | 32.82 | 15.70 | 0.27 | 0.67 | 525 | 32 | 300 |
| Ref. 4 | 4.7 | 51 | 37.82 | 15.10 | 0.27 | 0.67 | 525 | 32 | 300 |
| Ref. 5 | 4.9 | 51 | 38.14 | 15.14 | 0.28 | 0.66 | 525 | 32 | 390 |
| Ref. 6 | 4.8 | 49 | 37.11 | 14.21 | 0.28 | 0.66 | 525 | 32 | 380 |
| Ref. 7 | 4.1 | 33 | 26.11 | 11.21 | 0.28 | 0.66 | 525 | 32 | 200 |
| Ref. 8 | 5.1 | 51 | 34.14 | 14.12 | 0.28 | 0.66 | 525 | 32 | 280 |
| Ref. 9 | 5.0 | 52 | 35.14 | 13.80 | 0.34 | 0.59 | 531 | 51 | 310 |
| Ref. 10 | 4.1 | 34 | 27.11 | 12.14 | 0.28 | 0.66 | 525 | 32 | 250 |
| Example 1 | 4.7 | 53 | 40.14 | 16.14 | 0.27 | 0.67 | 525 | 32 | 500 |
| Example 2 | 4.9 | 50 | 38.14 | 15.41 | 0.27 | 0.67 | 525 | 32 | 480 |
| Example 3 | 4.7 | 53 | 39.12 | 16.10 | 0.32 | 0.60 | 528 | 48 | 450 |

As indicated in Table 2, compared to the OLEDs using only two luminous materials in the EML as References 1 and 2, the OLED applying three luminous materials whose energy level was controlled within the predetermined ranges into the EML of Examples 1 to 3 has lower driving voltage up to 6.0%. Besides, compared to the OLEDs in References 1 and 2, the OLEDs in Examples 1 to 3 have enhanced current efficiency up to 6.0%, power efficiency up to 5.2% and luminous life span up to 66.7%. Particularly, the OLED in Examples 1 to 3 has very narrows FWHM, which means improved color purity.

Also, compared to the OLEDs applying three luminous materials whose energy levels are not controlled within the predetermined ranges into the EML of References 3 to 10, the OLEDs applying three luminous materials whose energy level was controlled within the predetermined ranges into the EML of Examples 1 to 3 has lower driving voltage up to 7.8%. Besides, compared to OLEDs in References 3 to 10, the OLEDs in Examples 1 to 3 have enhanced current efficiency up to 60.7%, power efficiency up to 53.7%, EQE up to 44.0% and luminous life span up to 150.0%. From these results, it was confirmed that OLED lowers its driving voltage as well as improves its luminous efficiency and life span by applying three luminous compounds whose energy level were controlled within the predetermined ranges into the EML.

Example 4: Manufacture of OLED

An OLED was manufactured as the same process and the same material as Example 1, except that the EML includes "TH-1" by 59.5 wt %, "TD-1" by 40 wt % and "FD" by 0.5 wt %.

Example 5: Manufacture of OLED

An OLED was manufactured as the same process and the same material as Example 1, except that the EML includes "TH-1" by 49.5 wt %, "TD-1" by 50 wt % and "FD" by 0.5 wt %.

Example 6: Manufacture of OLED

An OLED was manufactured as the same process and the same material as Example 1, except that the EML includes "TH-2" by 59.5 wt %, "TD-1" by 40 wt % and "FD" by 0.5 wt %.

Example 7: Manufacture of OLED

An OLED was manufactured as the same process and the same material as Example 1, except that the EML includes "TH-2" by 49.5 wt %, "TD-1" by 50 wt % and "FD" by 0.5 wt %.

Example 8: Manufacture of OLED

An OLED was manufactured as the same process and the same material as Example 1, except that the EML includes "TH-2" by 59.5 wt %, "TD-2" by 40 wt % and "FD" by 0.5 wt %.

Example 9: Manufacture of OLED

An OLED was manufactured as the same process and the same material as Example 1, except that the EML includes "TH-2" by 49.5 wt %, "TD-1" by 50 wt % and "FD" by 0.5 wt %.

Experimental Example 3: Measurement of Luminous Properties of OLED

Luminous properties for each of the OLED manufactured in Example 1-9 were measured as the same process as Experimental Example 2. The measurement results are indicted in the following Table 3. Even if the doping concentration of the delayed fluorescent dopant is increased, the luminous efficiency is substantially identical. The life span of the OLED was increased by increasing the doping amount of "TD-1" as the delayed fluorescent dopant regardless of the host, while the life span of the OLED was a little bit decreased by increasing the doping amount of "TD-2" as the delayed fluorescent dopant.

TABLE 3

| | [V] | cd/A | lm/W | EQE [%] | CIEx | CIEy | $\lambda_{max}$ [nm] | FWHM [nm] | T95 @3000 nit |
|---|---|---|---|---|---|---|---|---|---|
| Example 1 | 4.7 | 53 | 40.14 | 16.14 | 0.27 | 0.67 | 525 | 32 | 500 |
| Example 4 | 4.7 | 52 | 39.14 | 16.01 | 0.28 | 0.67 | 528 | 33 | 505 |
| Example 5 | 4.6 | 52 | 39.54 | 16.08 | 0.28 | 0.68 | 530 | 33 | 520 |
| Example 2 | 4.9 | 50 | 38.14 | 15.41 | 0.27 | 0.67 | 525 | 32 | 480 |
| Example 6 | 4.8 | 50 | 37.50 | 15.11 | 0.28 | 0.68 | 530 | 33 | 485 |
| Example 7 | 4.8 | 49 | 37.81 | 14.98 | 0.28 | 0.68 | 530 | 33 | 500 |
| Example 3 | 4.7 | 53 | 39.12 | 16.10 | 0.32 | 0.60 | 528 | 48 | 450 |
| Example 8 | 5.1 | 47 | 35.25 | 14.54 | 0.27 | 0.63 | 528 | 41 | 435 |
| Example 9 | 5.2 | 45 | 33.24 | 13.24 | 0.27 | 0.62 | 528 | 38 | 445 |

Examples 1, 4 and 5: TH-1/TD-1/FD;
Examples 2, 5 and 7: TH-2/TD-1/FD;
Examples 3, 8 and 9: TH-2/TD-2/FD;
Examples 1-3: 30 wt % of delayed fluorescent material (TD-1 or TD-2)
Examples 4, 6 and 8: 40 wt % of delayed fluorescent material (TD-1 or TD-2)
Examples 5, 7 and 9: 50 wt % of delayed fluorescent material (TD-1 or TD-2)

Example 10: Manufacture of OLED

An OLED was manufactured as the same process and the same material as Example 1, except the thickness of the EML was set to 45 nm.

Example 11: Manufacture of OLED

An OLED was manufactured as the same process and the same material as Example 1, except the thickness of the EML was set to 55 nm.

Example 12: Manufacture of OLED

An OLED was manufactured as the same process and the same material as Example 2, except the thickness of the EML was set to 45 nm.

Example 13: Manufacture of OLED

An OLED was manufactured as the same process and the same material as Example 2, except the thickness of the EML was set to 55 nm.

Example 14: Manufacture of OLED

An OLED was manufactured as the same process and the same material as Example 3, except the thickness of the EML was set to 45 nm.

Example 15: Manufacture of OLED

An OLED was manufactured as the same process and the same material as Example 3, except the thickness of the EML was set to 55 nm.

Experimental Example 4: Measurement of Luminous Properties of OLED

Luminous properties for each of the OLED manufactured in Example 1-3 and 10-15 were measured as the same process as Experimental Example 2. The measurement results are indicted in the following Table 4. As indicated in Table 4, even if the thickness of the EML is increased, the luminous efficiency was maintained. When "TD-1" is used as the delayed fluorescent material regardless of the host, the luminous life span of the OLED increases as the thickness of the EML increases. On the other hand, when "TD-2" is used as the delayed fluorescent material, the luminous life span of the OLED decreases as the thickness of the EML increases. The result differences between the Experimental Examples 3 and 4 is attributed to the molecular structures of "TD-1" and "TD-2", which is presumably due to the differences in the strength of N-type characteristics (electron acceptor characteristics) and electron transporting abilities between two compounds.

TABLE 4

| | [V] | cd/A | lm/W | EQE [%] | CIEx | CIEy | $\lambda_{max}$ [nm] | FWHM [nm] | T95 @3000 nit |
|---|---|---|---|---|---|---|---|---|---|
| Example 1 | 4.7 | 53 | 40.14 | 16.14 | 0.27 | 0.67 | 525 | 32 | 500 |
| Example 10 | 4.7 | 52 | 39.14 | 17.04 | 0.28 | 0.67 | 528 | 33 | 520 |
| Example 11 | 4.6 | 52 | 39.54 | 16.55 | 0.28 | 0.68 | 530 | 33 | 550 |
| Example 2 | 4.9 | 50 | 38.14 | 15.41 | 0.27 | 0.67 | 525 | 32 | 480 |
| Example 12 | 4.8 | 50 | 37.50 | 16.04 | 0.28 | 0.68 | 530 | 33 | 490 |
| Example 13 | 4.8 | 49 | 37.81 | 15.14 | 0.27 | 0.68 | 530 | 33 | 510 |
| Example 3 | 4.7 | 53 | 39.12 | 16.10 | 0.32 | 0.60 | 528 | 48 | 450 |

TABLE 4-continued

| | [V] | cd/A | lm/W | EQE [%] | CIEx | CIEy | $\lambda_{max}$ [nm] | FWHM [nm] | T95 @3000 nit |
|---|---|---|---|---|---|---|---|---|---|
| Example 14 | 4.9 | 47 | 36.89 | 15.54 | 0.27 | 0.63 | 528 | 41 | 435 |
| Example 15 | 5.1 | 45 | 34.21 | 14.24 | 0.27 | 0.62 | 528 | 38 | 405 |

Examples 1, 10 and 11: TH-1/TD-1/FD;
Examples 2, 12 and 13: TH-2/TD-1/FD;
Examples 3, 14 and 15: TH-2/TD-2/FD;
Examples 1-3: EML thickness 35 nm;
Examples 10, 12 and 14: EML thickness 45 nm;
Examples 11, 13 and 15: EML thickness 55 nm While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic light emitting diode, comprising:
first and second electrodes facing each other; and
at least one emitting unit disposed between the first and second electrodes and comprising an emitting material layer,
wherein the emitting material layer comprises a first compound, a second compound and a third compound,
wherein a Lowest Unoccupied Molecular Orbital (LUMO) energy level (LUMO$^H$) of the first compound and a LUMO energy level (LUMO$^{TD}$) of the second compound satisfies the following relationship in Equation (1),
wherein a Highest Occupied Molecular Orbital (HOMO) energy level (HOMO$^H$) of the first compound, a HOMO energy level (HOMO$^{TD}$) of the second compound and a HOMO energy level (HOMO$^{FD}$) of the third compound satisfies the following relationship in Equation (2),
wherein an excited state singlet energy level (S$_1^H$) of the first compound is higher than an excited state singlet energy level (S$_1^{TD}$) of the second compound, and
wherein an excited state singlet energy level (S$_1^{TD}$) of the second compound is higher than an excited state singlet energy level (Sim) of the third compound:

$$|LUMO^H - LUMO^{TD}| \leq 0.8 \text{ eV} \quad (1)$$

$$|HOMO^H| \geq |HOMO^{TD}| \geq |HOMO^{FD}| \quad (2),$$

wherein the first compound is selected from a compound having the following structure of Chemical Formula 3:

Chemical Formula 3

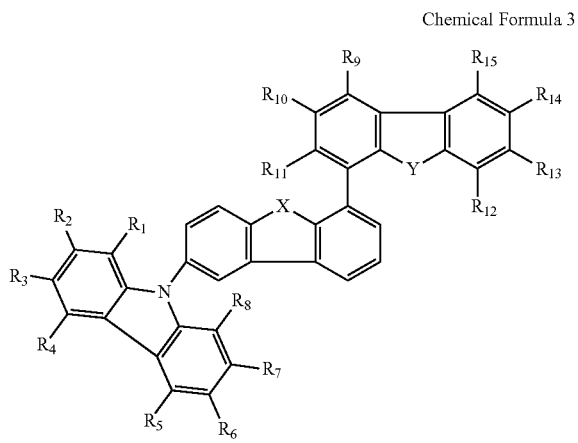

wherein each of $R_1$ to $R_{15}$ is independently hydrogen, deuterium, tritium, silyl group, $C_1\sim C_{10}$ alkyl group, $C_1\sim C_{10}$ alkoxy group, $C_1\sim C_{10}$ alkyl amino group, $C_5\sim C_{30}$ aryl group, $C_5\sim C_{30}$ alkyl aryl group, $C_5\sim C_{30}$ aryloxyl group, or $C_5\sim C_{30}$ aryl amino group or two adjacent groups among $R_1$ to $R_{15}$ forms a fused aryl ring or a fused hetero aryl ring each of which is unsubstituted or substituted with $C_5\sim C_{30}$ aryl group or $C_4\sim C_{30}$ hetero aryl group; and each of X and Y is independently oxygen (O) or sulfur (S);

wherein the second compound comprises:

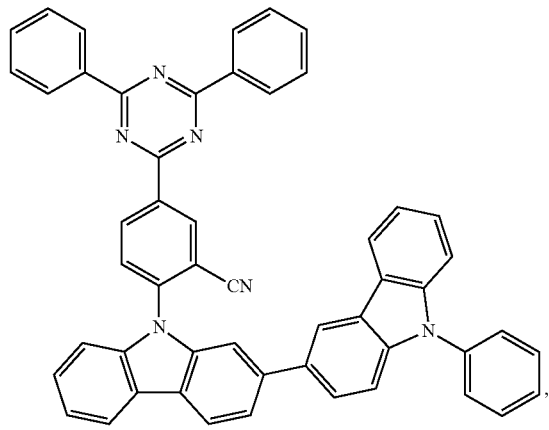

TD-3 wherein the third compound has a quinoline-acridine core, and
wherein the third compound is selected from the group consisting of 5,12-dimethylquinolino(2,3-b)acridine-7,14(5H, 12H)-dione, 5,12-diethylquinolino(2,3-b)acridine-7,14(5H, 12H)-dione, 5,12-dibutyl-3,10-difluoroquinolino(2,3-b)acridine-7,14(5H, 12H)-dione, 5,12-dibutyl-3,10-bis(trifluromethyl)quinolino(2,3-b)acridine-7,14(5H, 12H)-dione and combinations thereof.

2. The organic light emitting diode of claim 1, wherein an energy level bandgap between the excited state singlet energy level and an excited state triplet energy level of the first compound is more than about 0.3 eV,
wherein an energy level bandgap between the excited state singlet energy level and an excited state triplet energy level of the third compound is more than about 0.3 eV, and
wherein an energy level bandgap between the excited state singlet energy level and an excited state triplet energy level of the second compound is equal to or less than about 0.3 eV.

3. The organic light emitting diode of claim 1, wherein an energy level bandgap between the HOMO energy level (HOMO$^H$) and the LUMO energy level (LUMO$^H$) of the first compound is larger than an energy level bandgap between the HOMO energy level (HOMO$^{TD}$) and the LUMO energy level (LUMO$^{TD}$) of the second compound, and
wherein the energy level bandgap between the HOMO energy level (HOMO$^{TD}$) and the LUMO energy level (LUMO$^{TD}$) of the second compound is larger than an energy level bandgap between the HOMO energy level (HOMOm) and an LUMO energy level (LUMO$^{FD}$) of the third compound.

4. The organic light emitting diode of claim 1, wherein the at least one emitting unit includes a first emitting unit disposed between the first and second electrodes and having a first emitting material layer, and a second emitting unit disposed between the first emitting unit and the second electrode and having a second emitting material layer,
wherein one emitting material layer of the first and second emitting material layers includes the first compound, the second compound and the third compound, and
further comprises a charge generation layer between the first and second emitting units.

5. An organic light emitting diode, comprising:
first and second electrodes facing each other; and
at least one emitting unit disposed between the first and second electrodes and including an emitting material layer,
wherein the emitting material layer includes a first compound, a second compound and a third compound,
wherein a Lowest Unoccupied Molecular Orbital (LUMO) energy level of the first compound (LUMO$^H$) and a LUMO energy level of the second compound (LUMO$^{TD}$) satisfy the following relationship in Equation (1),
wherein a Highest Occupied Molecular Orbital (HOMO) energy level of the first compound (HOMO$^H$), a HOMO energy level of the second compound (HOMO$^{TD}$) and a HOMO energy level of the third compound (HOMO$^{FD}$) satisfy the following relationship in Equation (2):

$$|LUMO^H|-|LUMO^{TD}|\leq 0.8 \text{ eV} \quad (1)$$

$$|HOMO^H|\geq|HOMO^{TD}|\geq|HOMO^{FD}| \quad (2)$$

wherein the first compound is selected from a compound having the following structure of Chemical Formula 3:

Chemical Formula 3

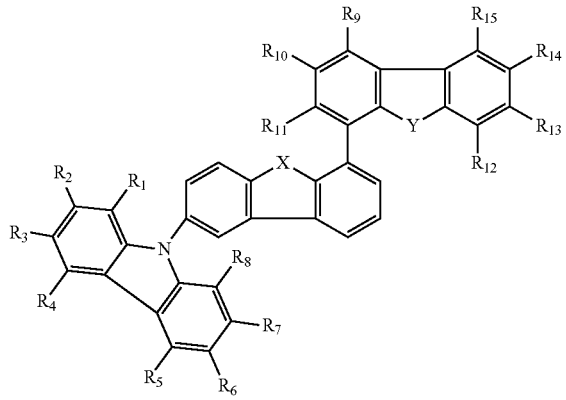

wherein each of $R_1$ to $R_{15}$ is independently hydrogen, deuterium, tritium, silyl group, $C_1$~$C_{10}$ alkyl group, $C_1$~$C_{10}$ alkoxy group, $C_1$-$C_{10}$ alkyl amino group, $C_5$~$C_{30}$ aryl group, $C_5$~$C_{30}$ alkyl aryl group, $C_5$~$C_{30}$ aryloxyl group, or $C_5$~$C_{30}$ aryl amino group, or two adjacent groups among $R_1$ to $R_{15}$ forms a fused aryl ring or a fused hetero aryl ring each of which is unsubstituted or substituted with $C_5$~$C_{30}$ aryl group or $C_4$~$C_{30}$ hetero aryl group; and
each of X and Y is independently oxygen (O) or sulfur (S);

wherein the second compound comprises:

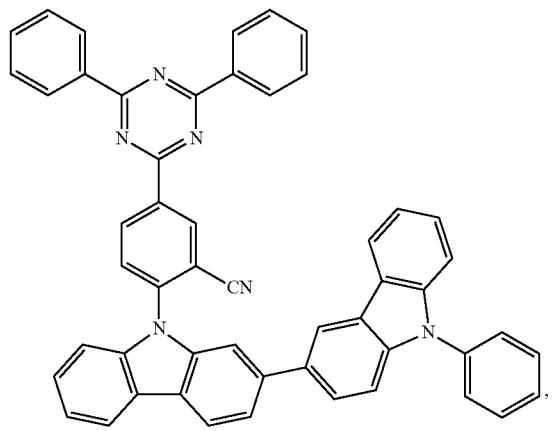
TD-3 wherein the third compound has a quinoline-acridine core, and wherein the third compound is selected from the group consisting of 5,12-dimethylquinolino(2,3-b)acridine-7,14(5H, 12H)-dione, 5,12-diethylquinoline(2,3-b)acridine-7,14(5H, 12H)-dione, 5,12-dibutyl-3,10-difluoroquinolino(2,3-b)acridine-7,14(5H, 12H)-dione, 5,12-dibutyl-3,10-bis(trifluromethyl)quinolino(2,3-b)acridine-7,14(5H, 12H)-dione and combinations thereof.

6. The organic light emitting diode of claim 5, wherein the first compound includes a compound having any one of the following structures:

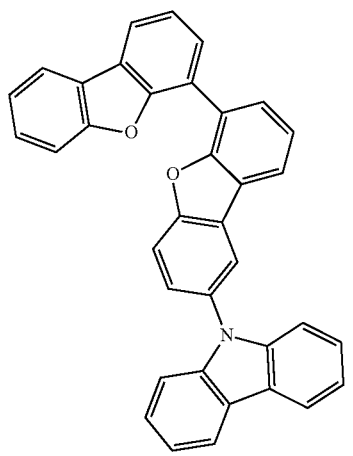

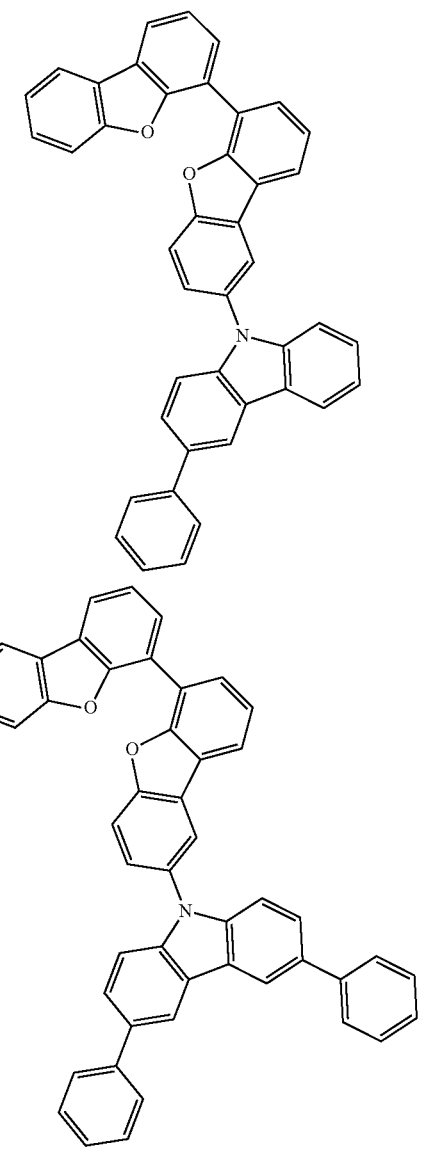

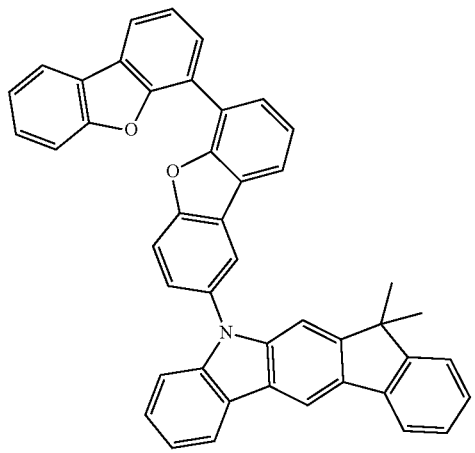

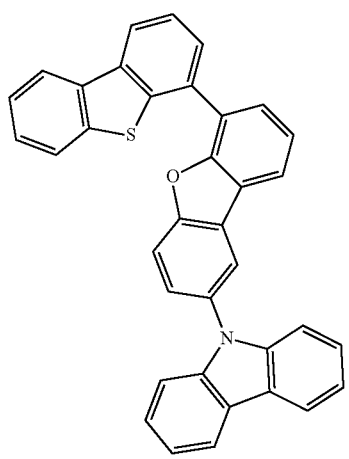
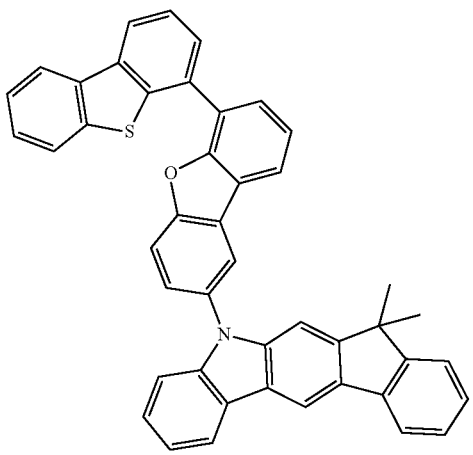
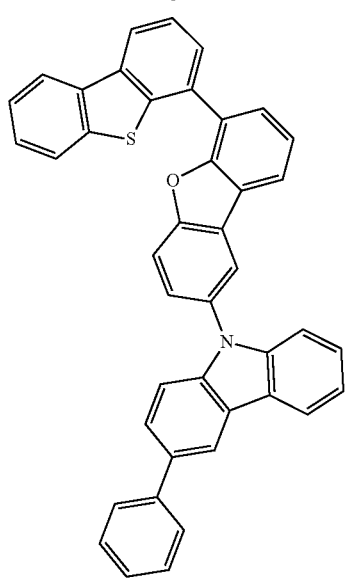
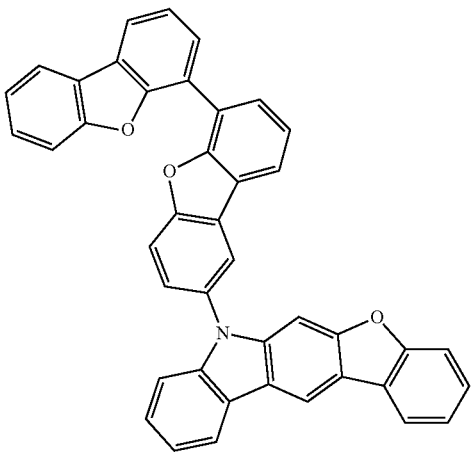
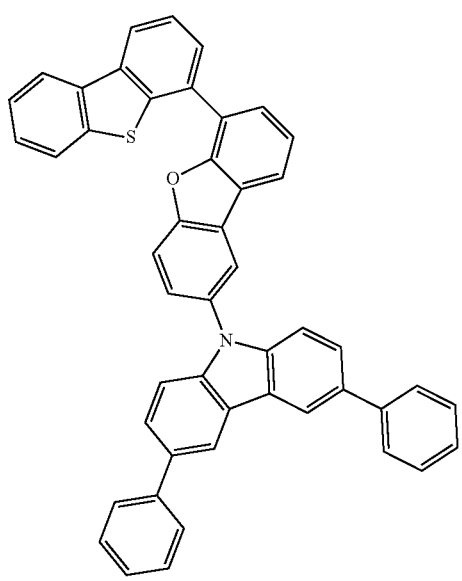

137
-continued
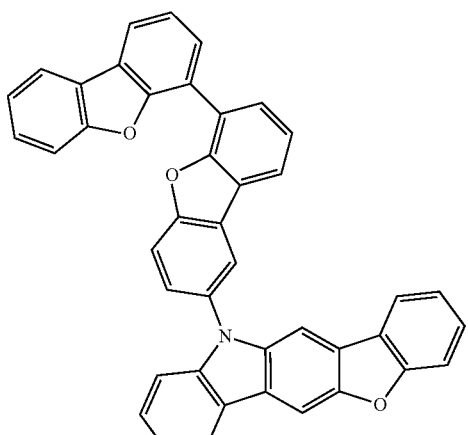
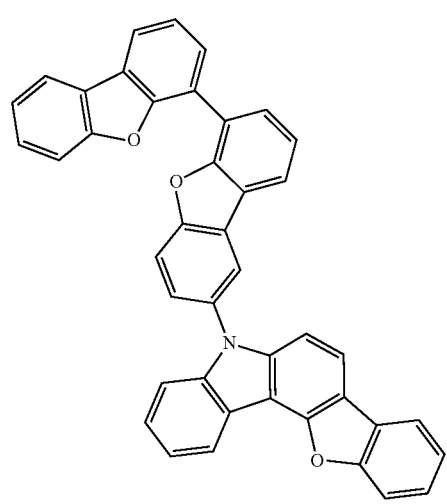
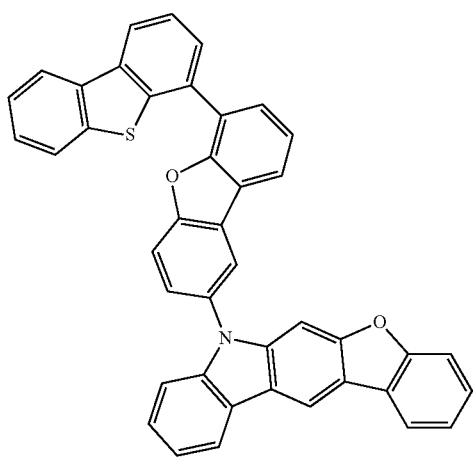
138
-continued
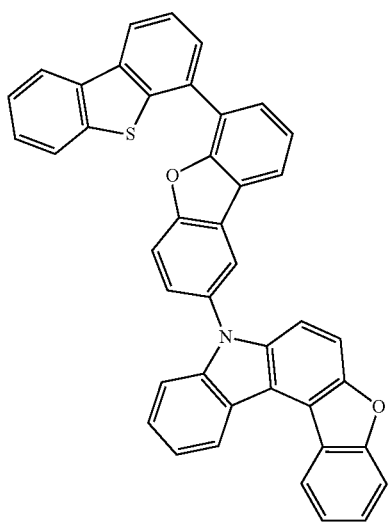
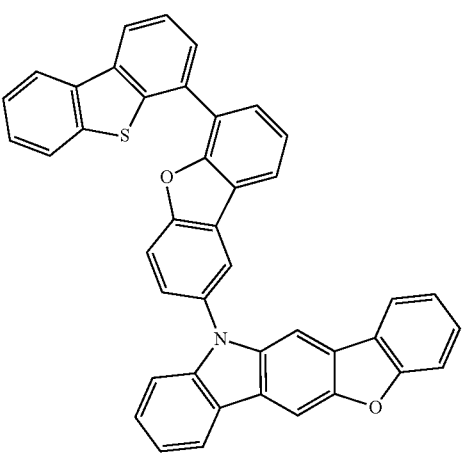
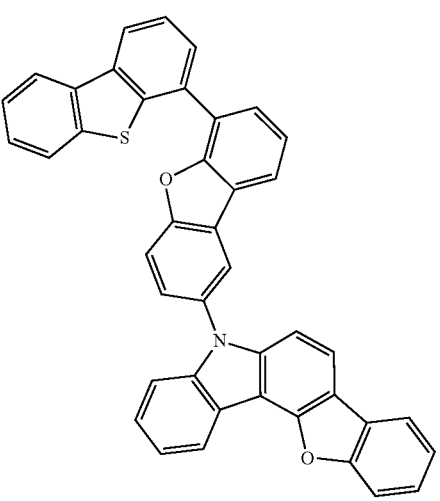

139
-continued
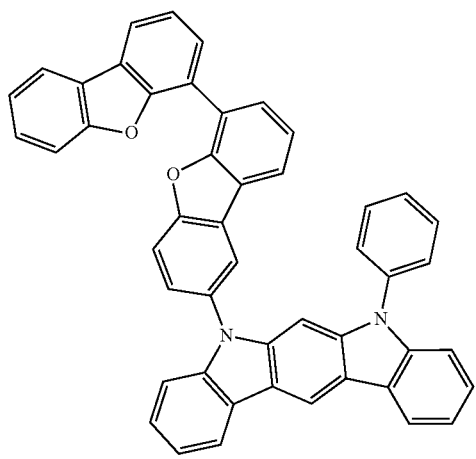
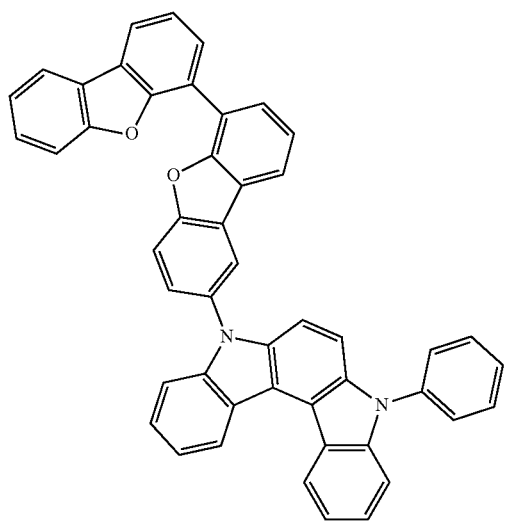
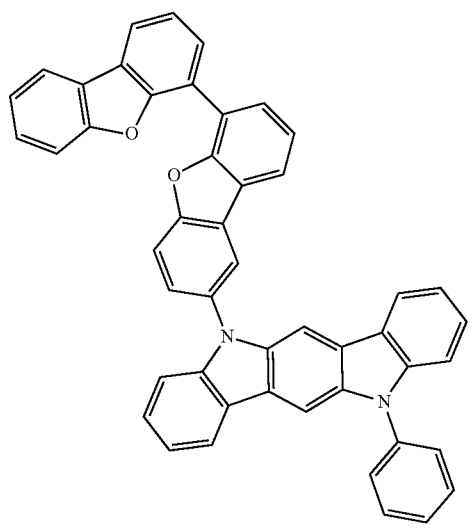
140
-continued
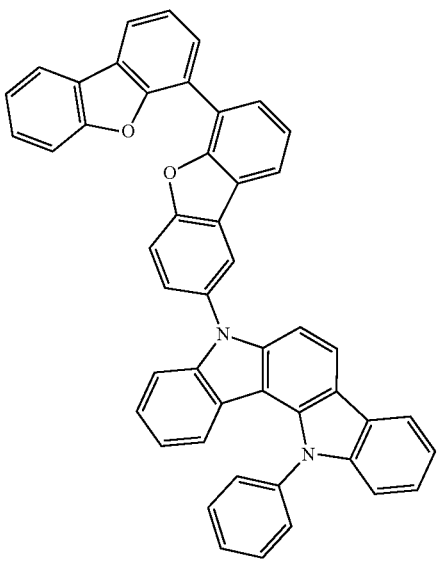
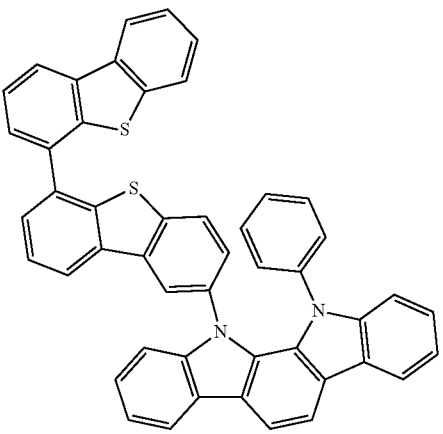
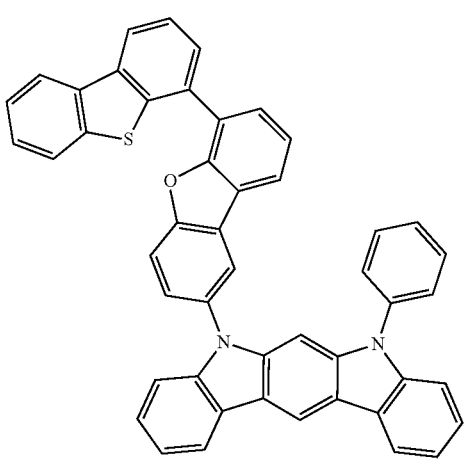

141
-continued
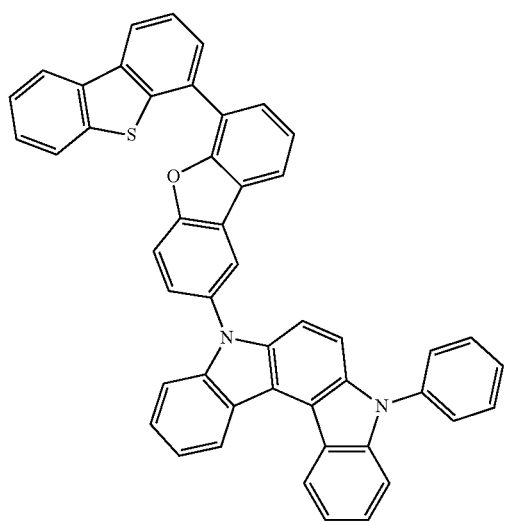
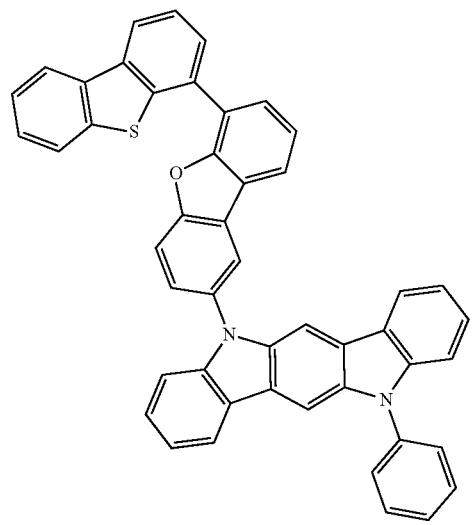
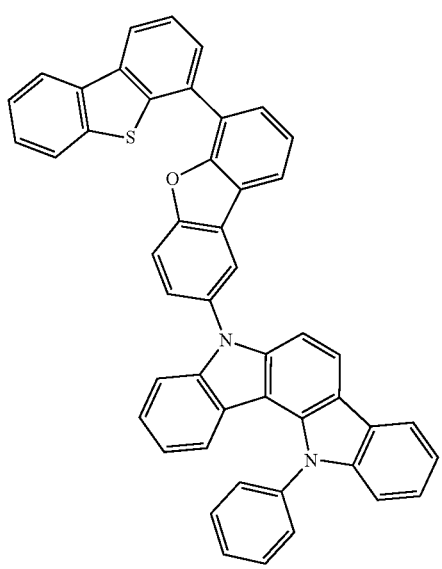
142
-continued
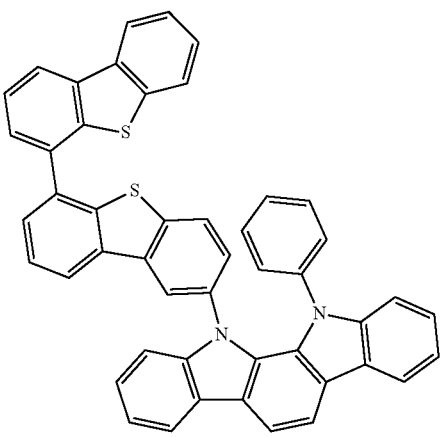
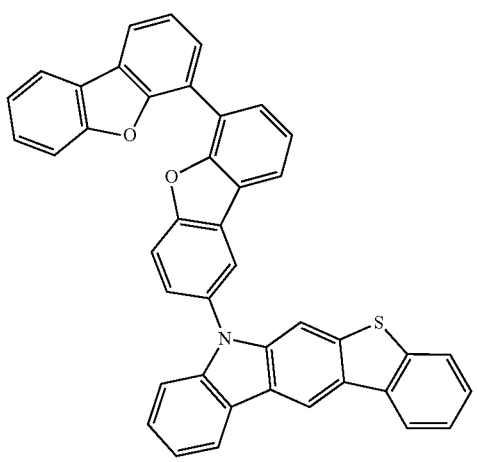
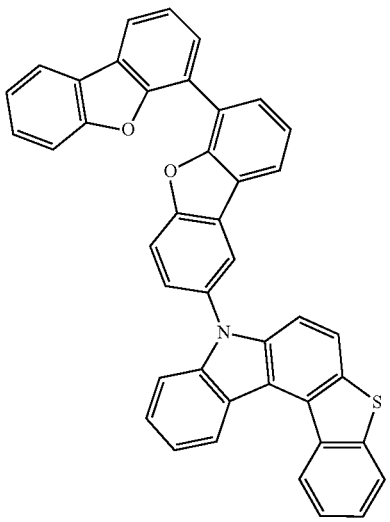

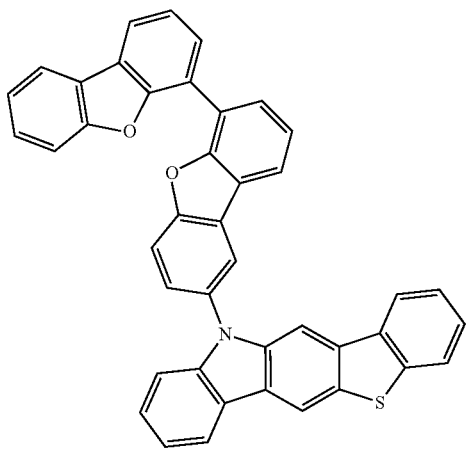
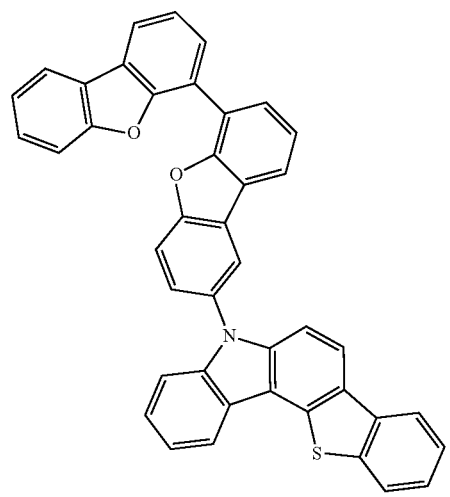
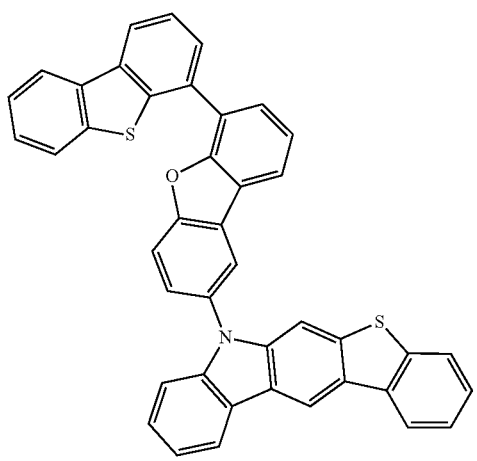
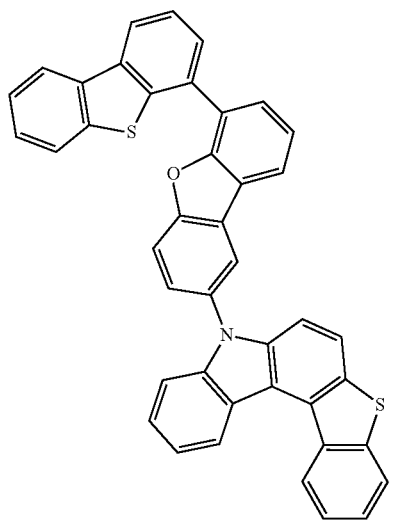
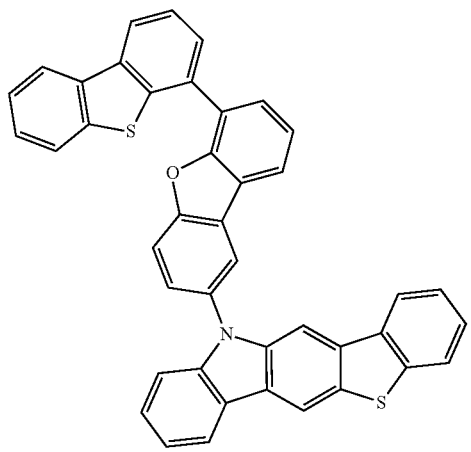
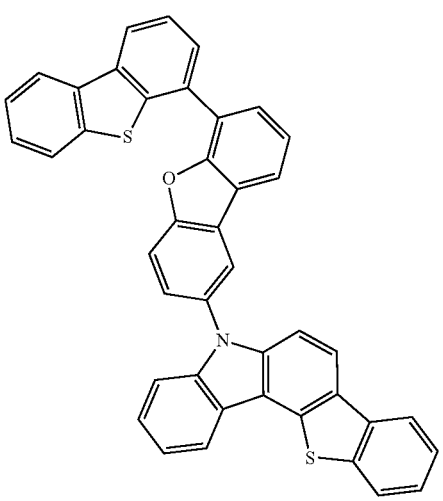

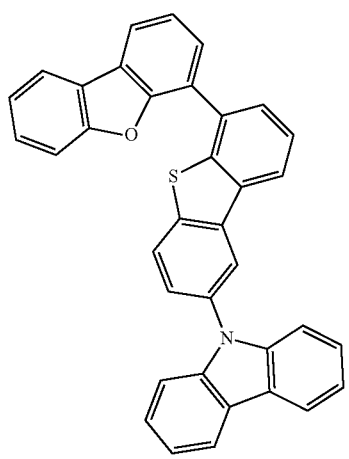
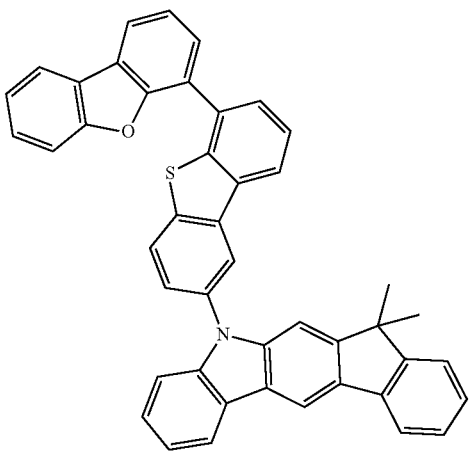
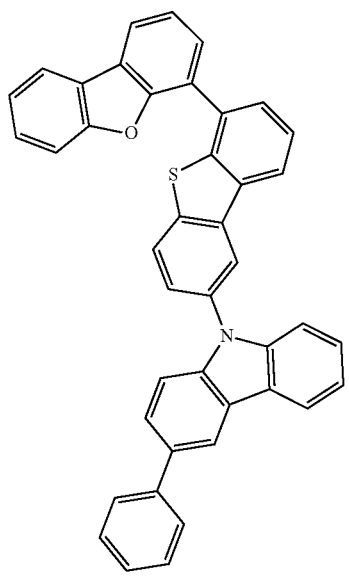
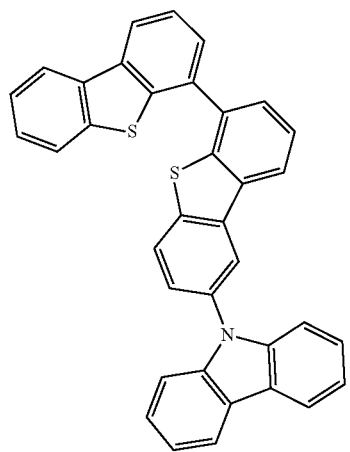
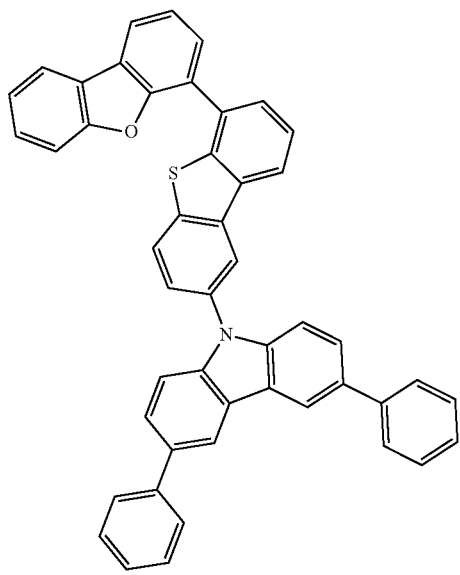
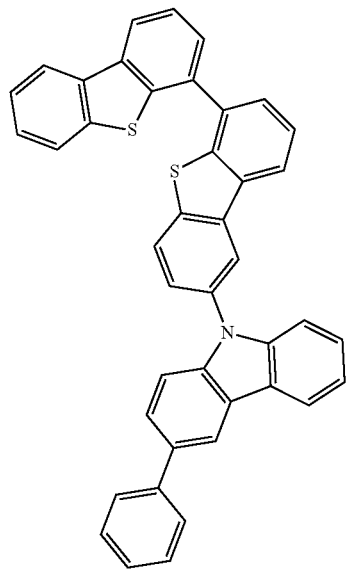

147
-continued
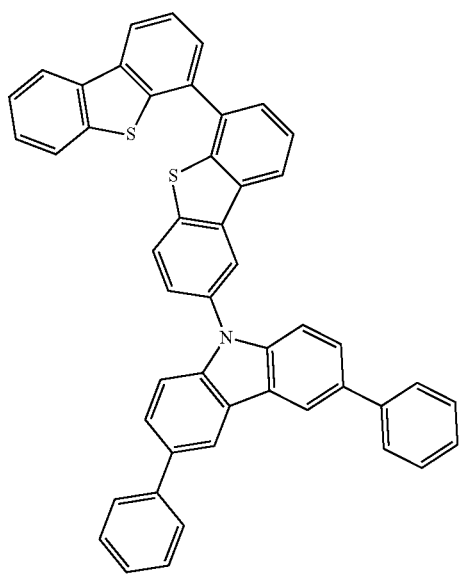
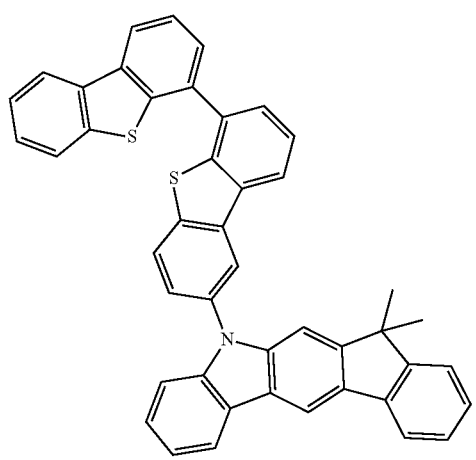
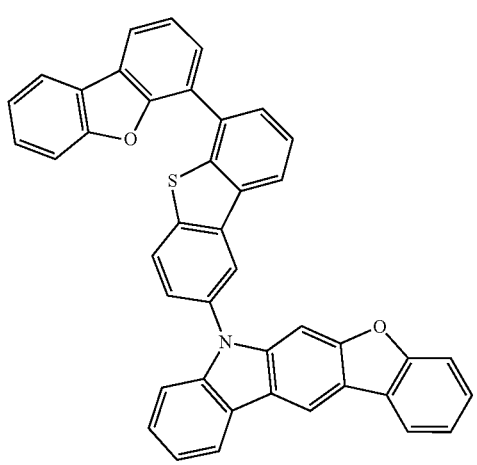
148
-continued
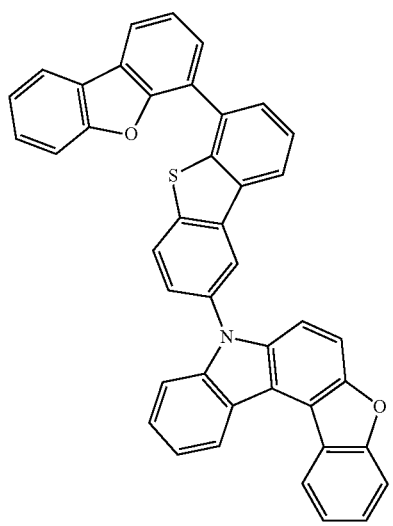
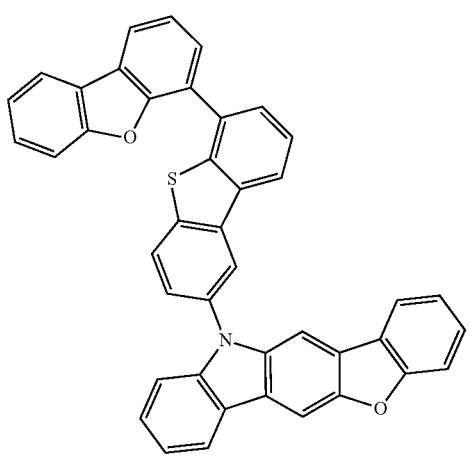
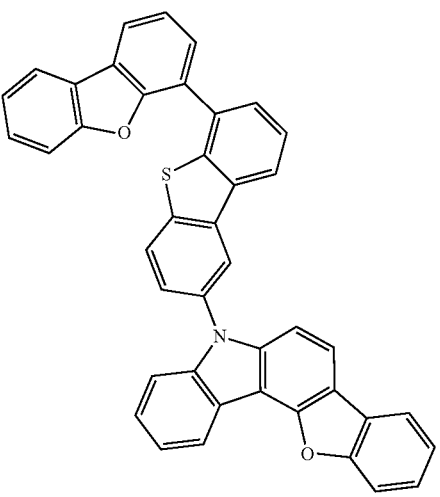

-continued
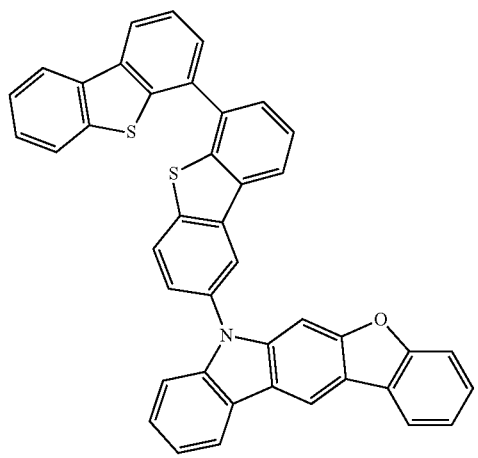
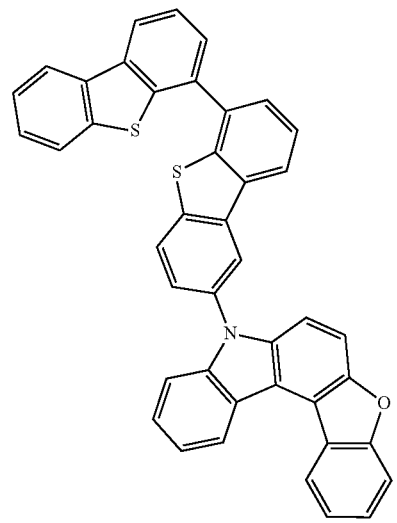
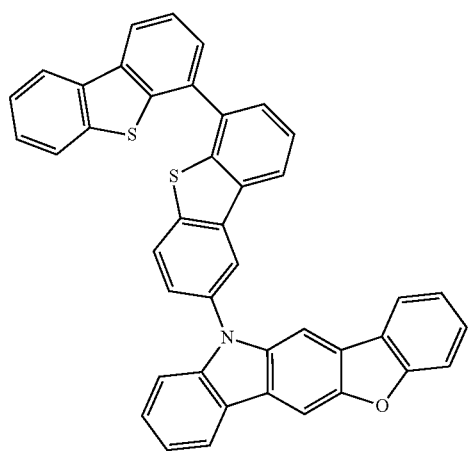
-continued
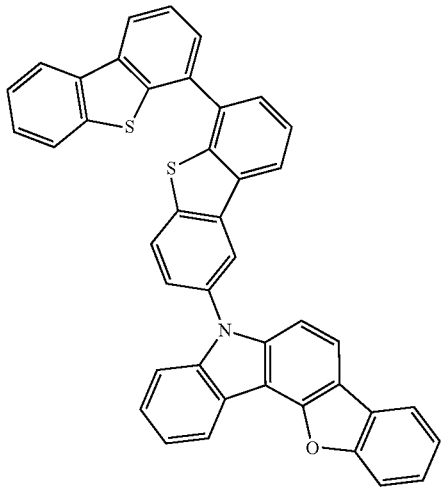
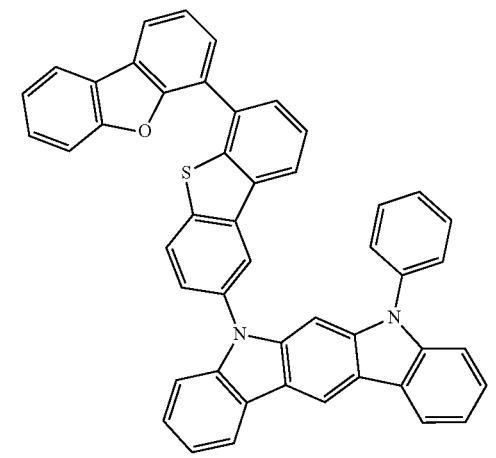
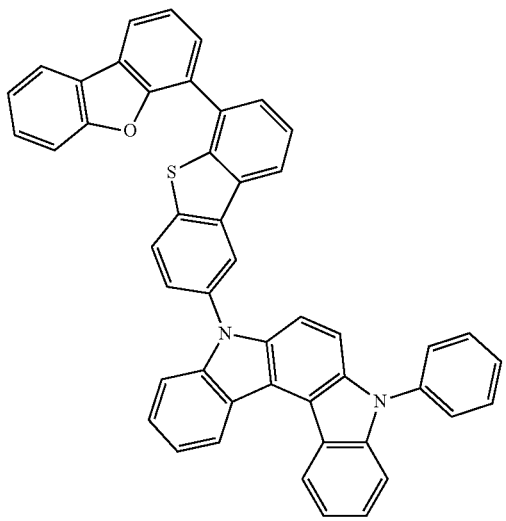

151
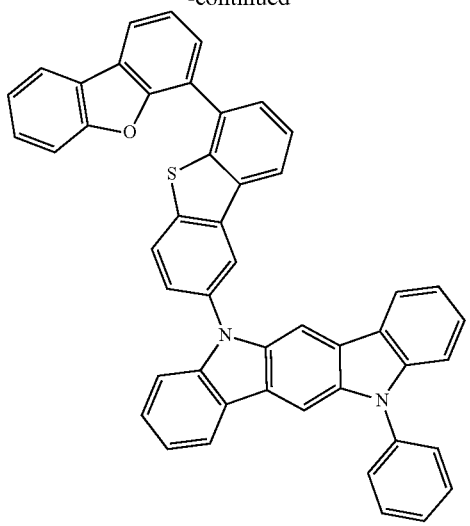
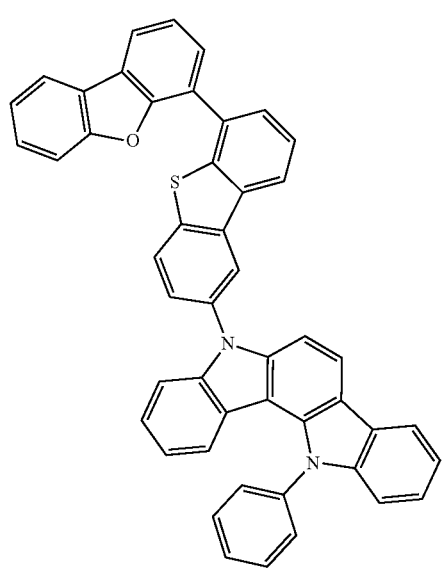
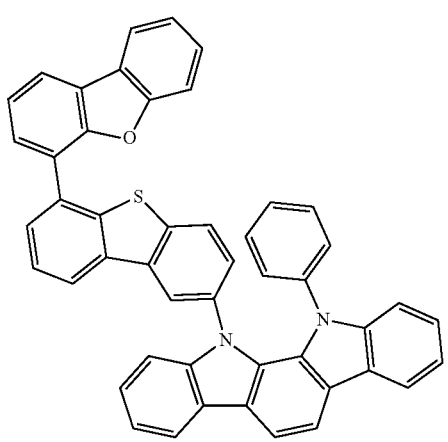
152
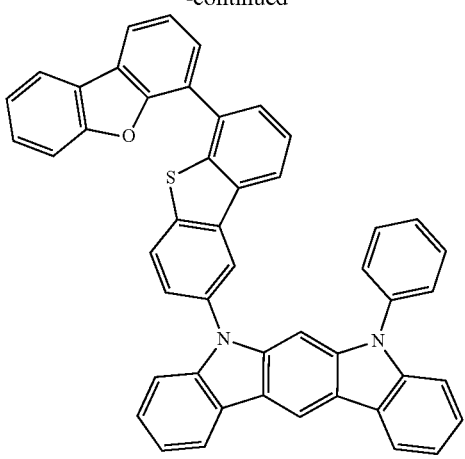
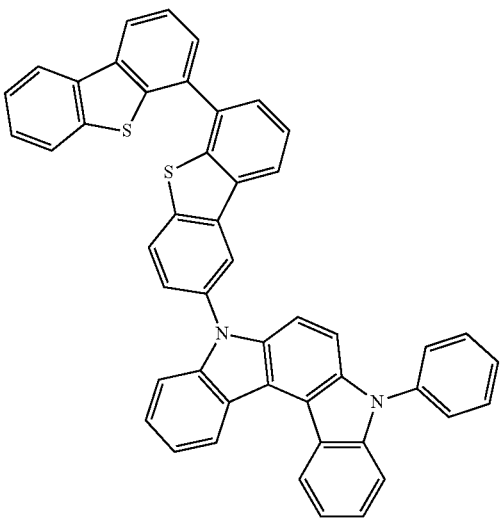
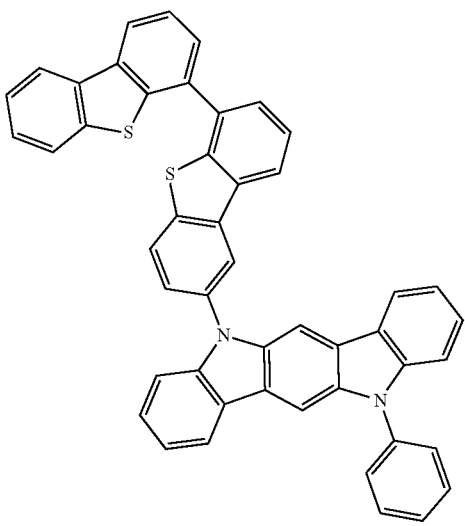

153
-continued
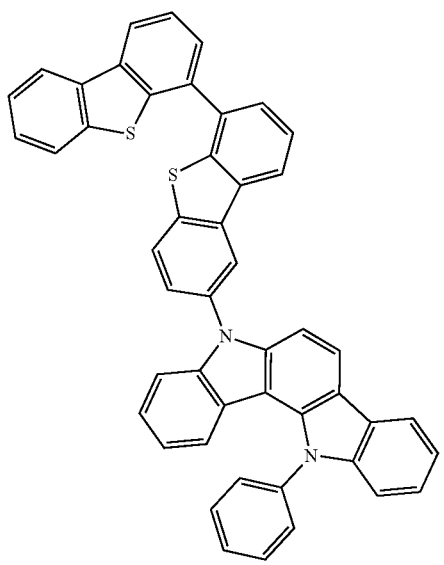
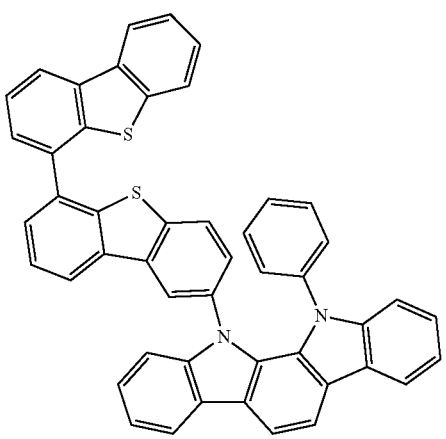
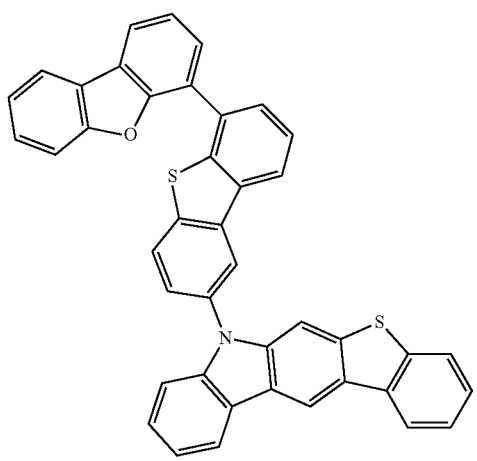
154
-continued
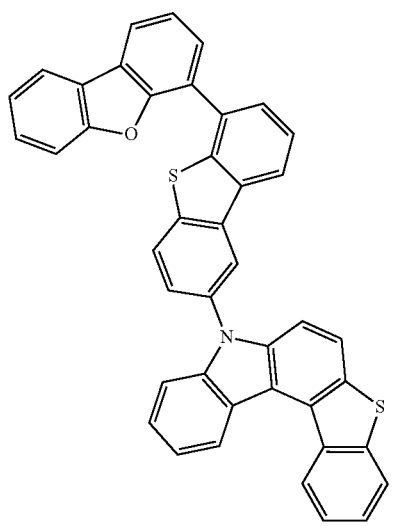
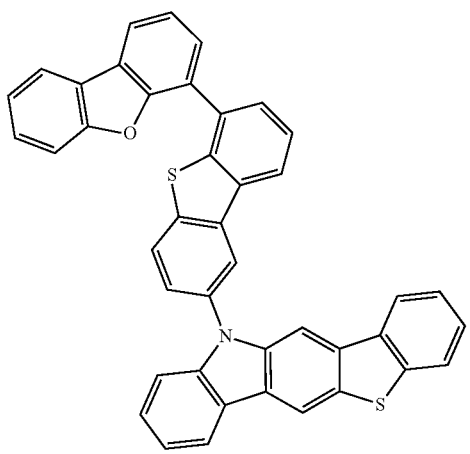
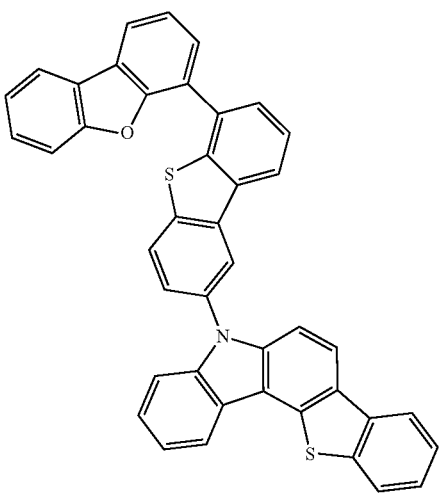

155
-continued
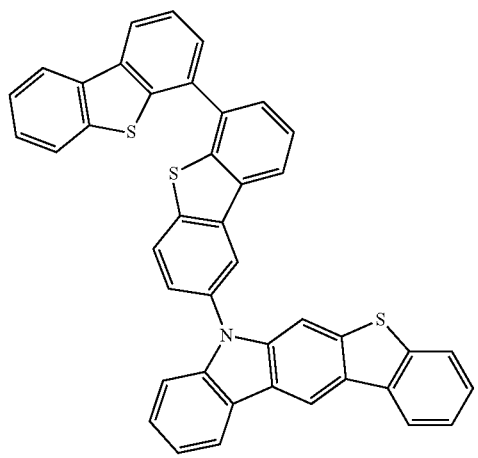
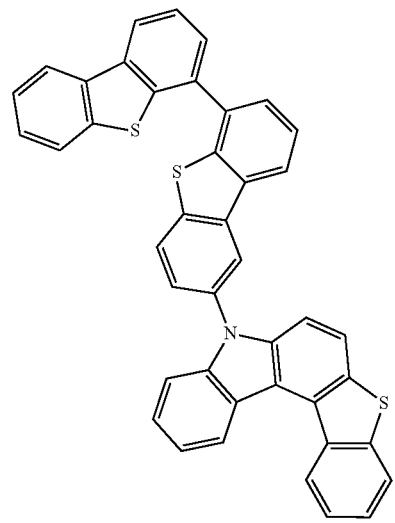
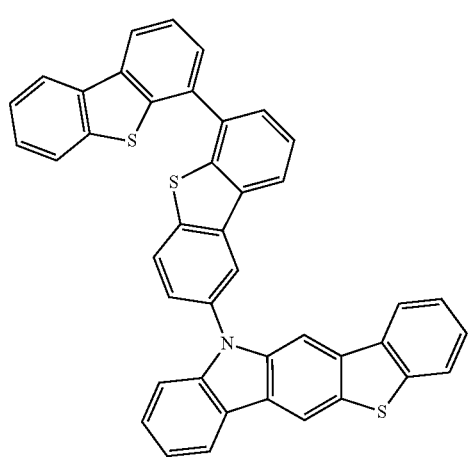
156
-continued
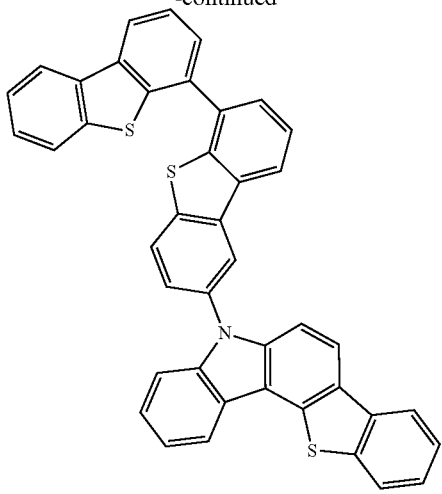
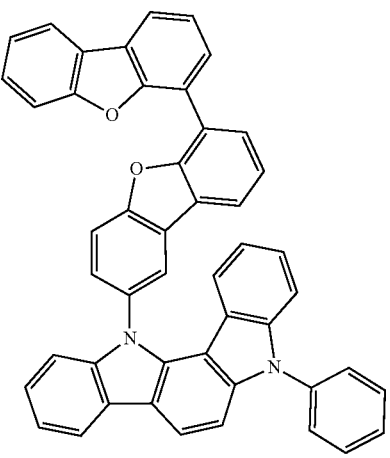
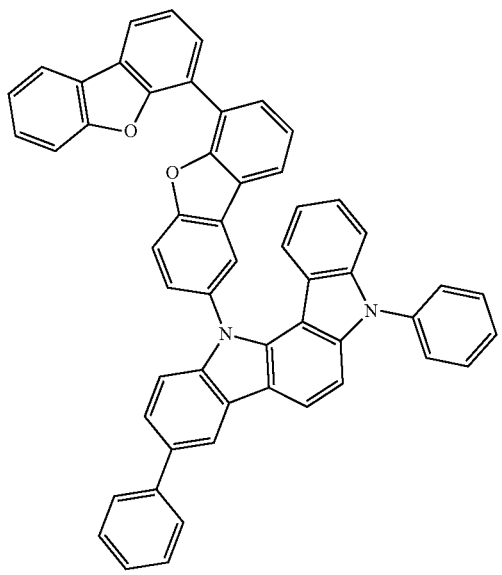

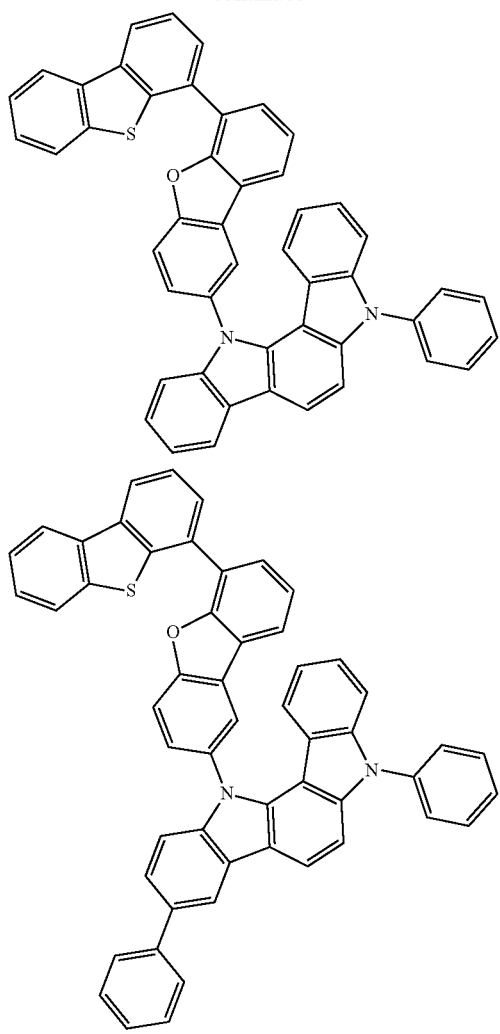
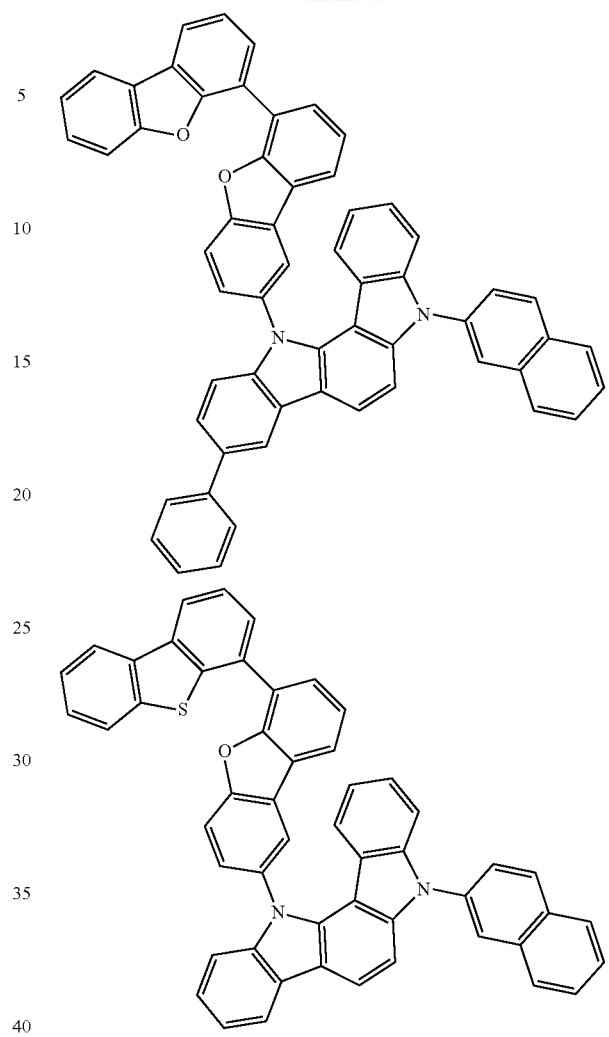
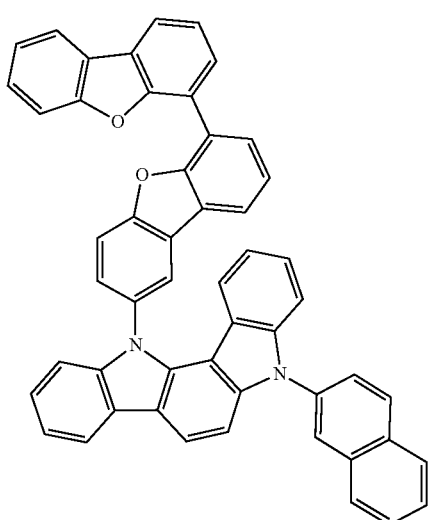
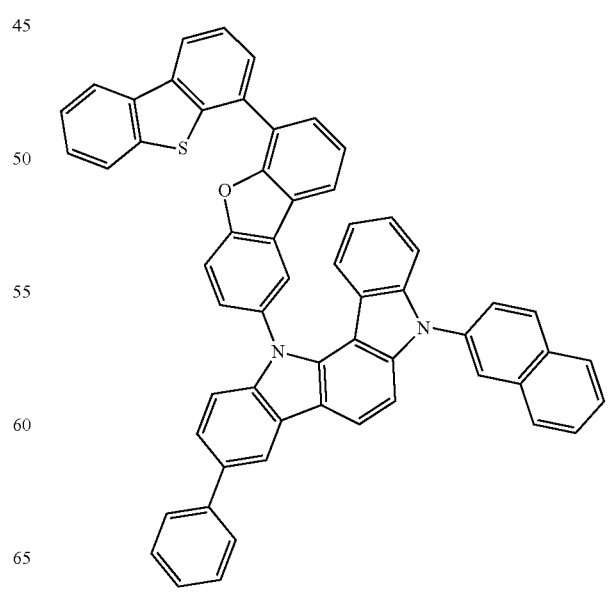

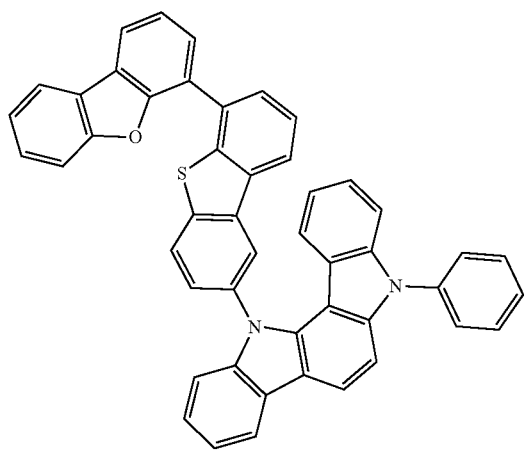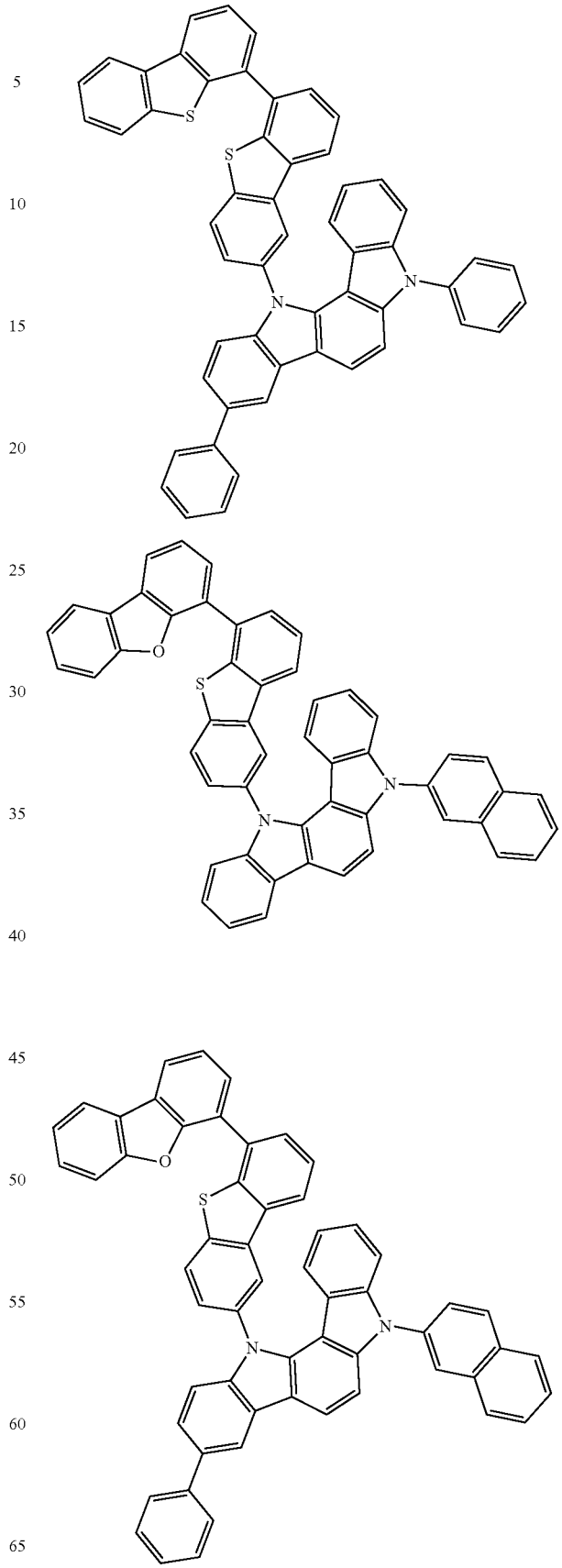

161
-continued
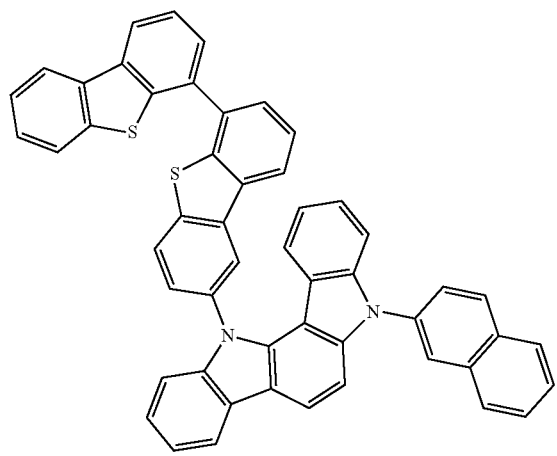
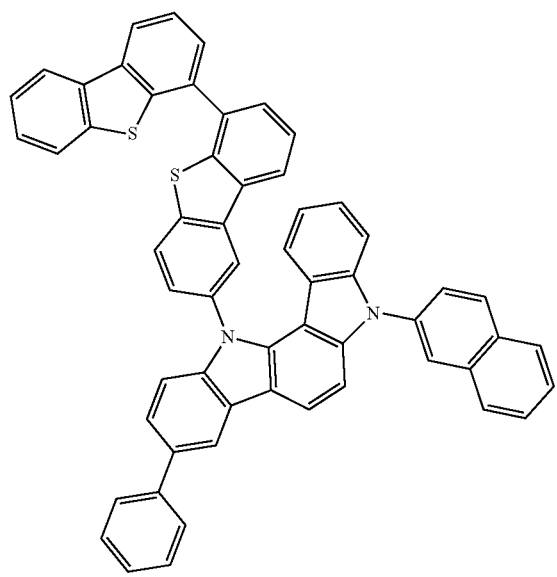
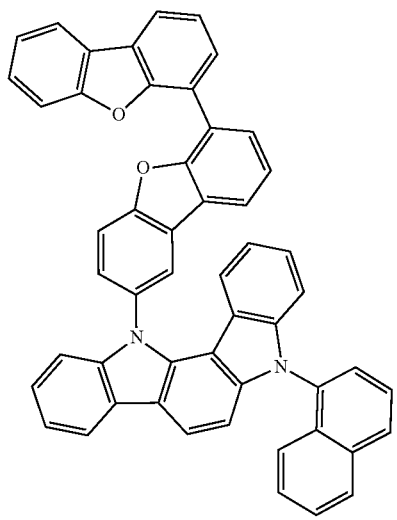
162
-continued
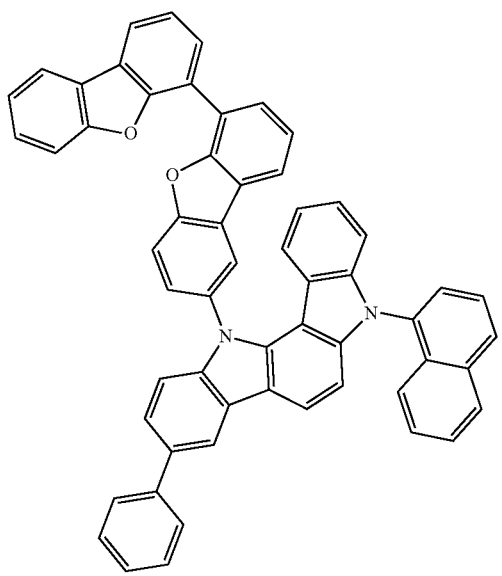
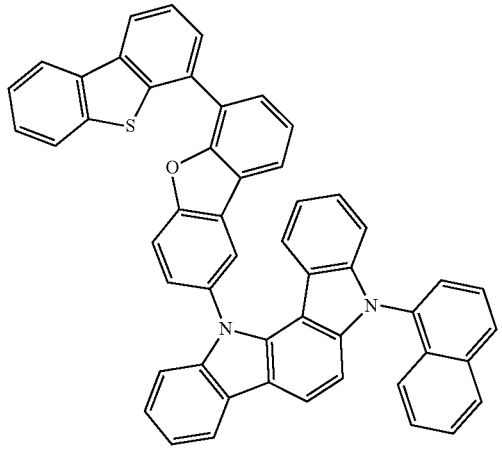
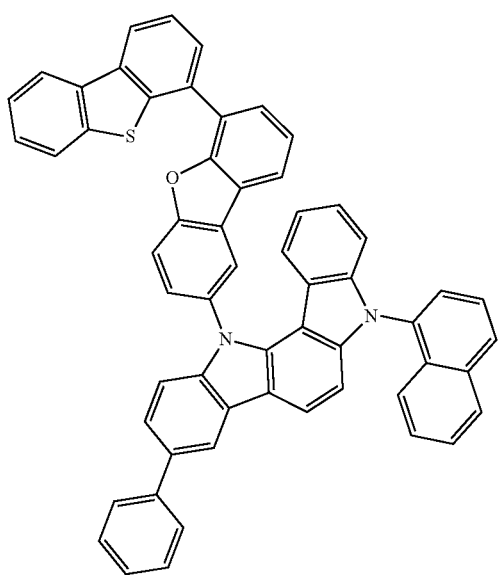

163
-continued
164
-continued
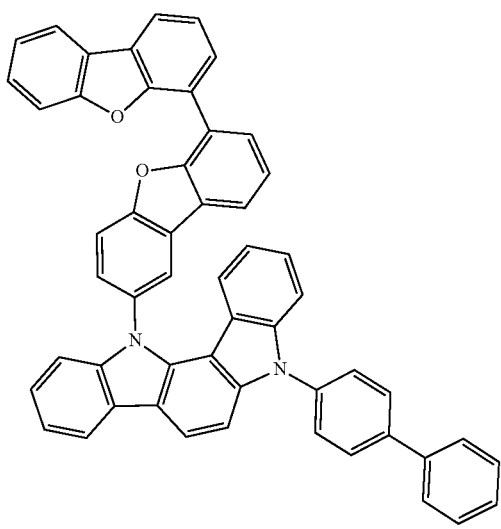
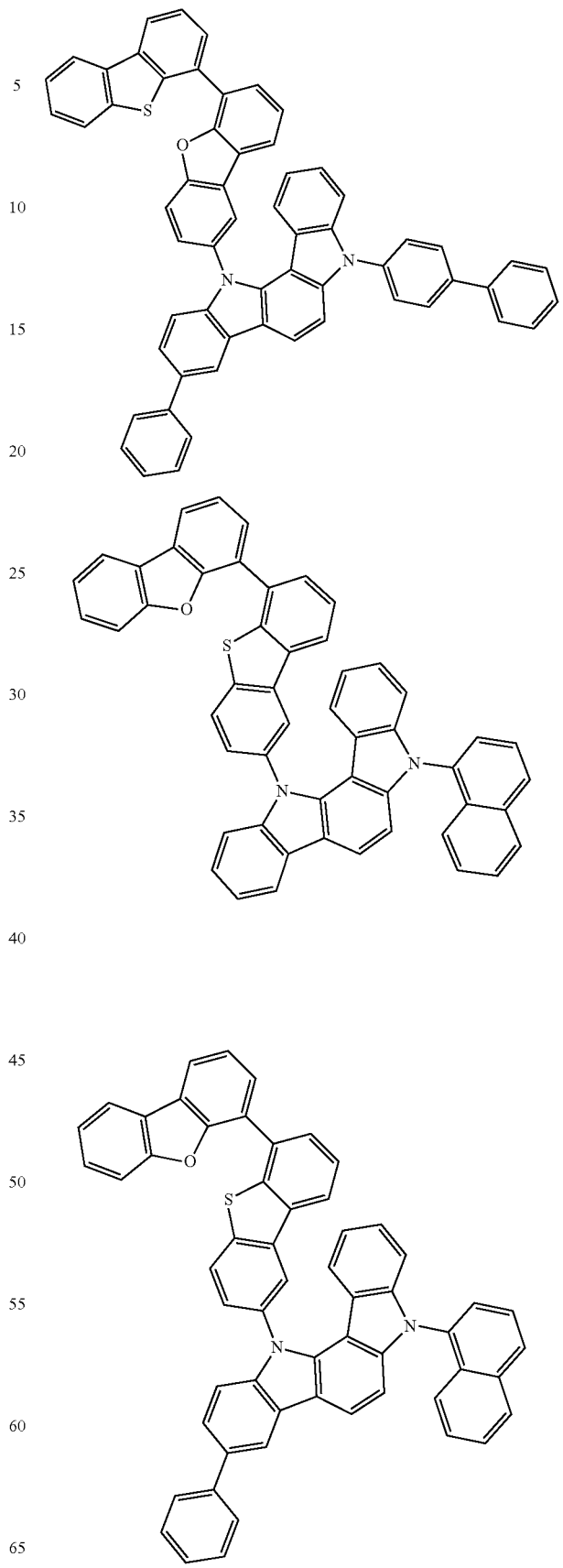

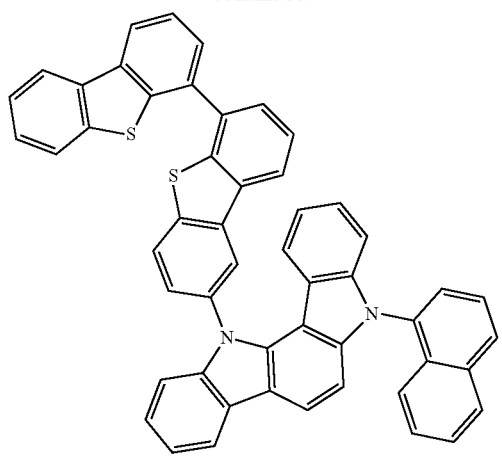

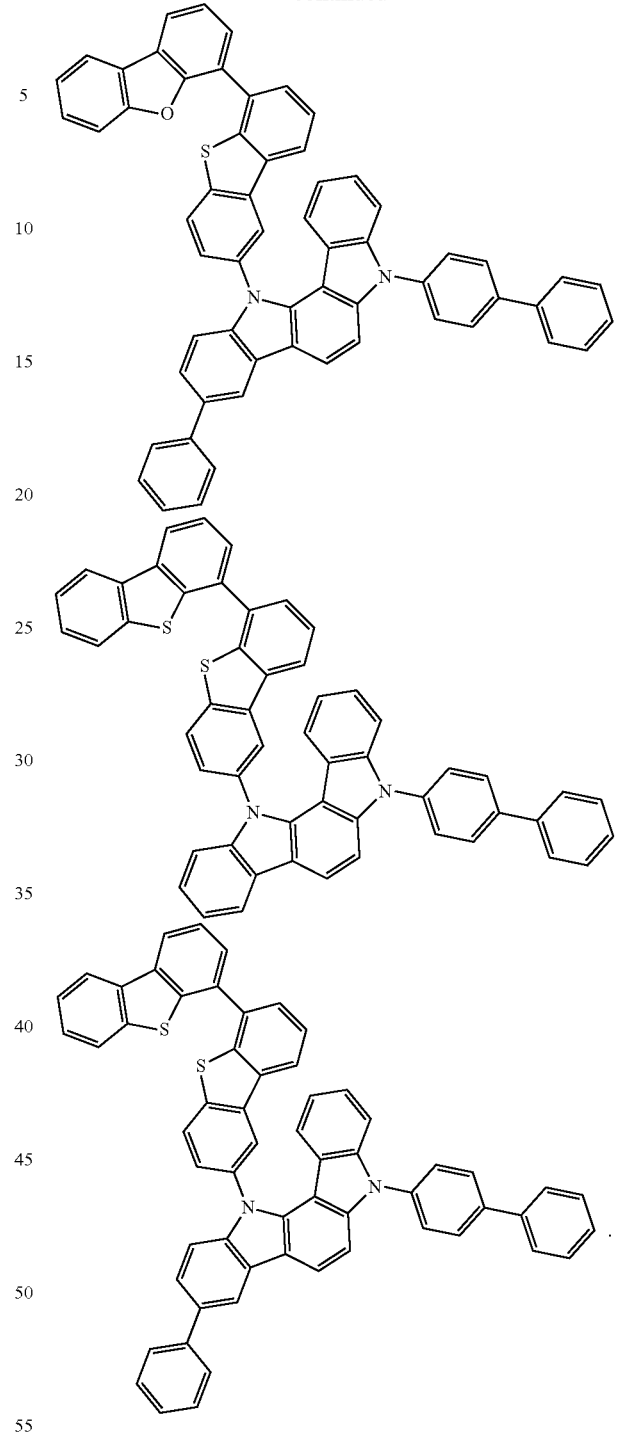

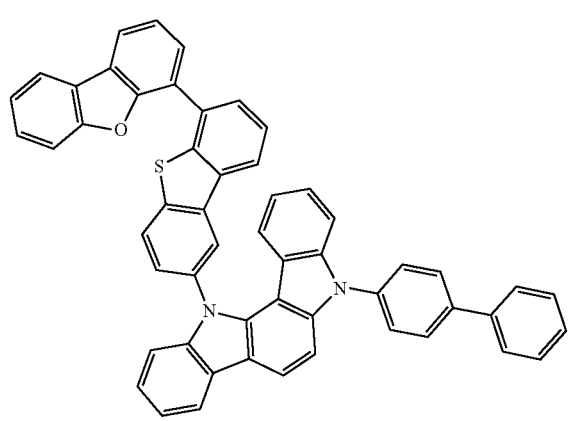

7. The organic light emitting diode of claim 5, wherein an excited state singlet energy level of the first compound is higher than an excited state singlet energy level of the second compound.

8. The organic light emitting diode of claim 5, wherein an excited state singlet energy level of the second compound is higher than an excited state singlet energy level of the third compound.

9. The organic light emitting diode of claim 5, wherein an energy level bandgap between an excited state singlet energy level and an excited state triplet energy level of the second compound is equal to or less than about 0.3 eV.

10. The organic light emitting diode of claim 5, wherein each of an energy level bandgap between an excited state singlet energy level and an excited state triplet energy level of the first compound and an energy level bandgap between an excited state singlet energy level and an excited state triplet energy level of the third compound is more than about 0.3 eV, respectively.

11. The organic light emitting diode of claim 5, wherein an energy level bandgap between the HOMO energy level ($HOMO^H$) and the LUMO energy level ($LUMO^H$) of the first compound is larger than an energy level bandgap between the HOMO energy level ($HOMO^{TD}$) and the LUMO energy level ($LUMO^{TD}$) of the second compound, and wherein the energy level bandgap between the HOMO energy level ($HOMO^{TD}$) and the LUMO energy level ($LUMO^{TD}$) of the second compound is larger than an energy level bandgap between the HOMO energy level ($HOMO^{FD}$) and an LUMO energy level ($LUMO^{FD}$) of the third compound.

12. The organic light emitting diode of claim 5, wherein an excited state triplet energy level of the second compound is less than an excited state triplet energy level of the first compound and is higher than an excited state triplet energy level of the third compound.

13. The organic light emitting diode of claim 5, wherein the at least one emitting unit includes a first emitting unit disposed between the first and second electrodes and having a first emitting material layer, and a second emitting unit disposed between the first emitting unit and the second electrode and having a second emitting material layer, wherein one emitting material layer of the first and second emitting material layers includes the first compound, the second compound and the third compound, and further comprising a charge generation layer between the first and second emitting units.

14. An organic light emitting device, comprising:
a substrate; and
the organic light emitting diode according to claim 1 over the substrate.

15. The organic light emitting device of claim 14, wherein the organic light emitting device is an organic light emitting display device or an organic light emitting illumination device.

16. An organic light emitting device, comprising:
a substrate; and
the organic light emitting diode according to claim A over the substrate.

17. The organic light emitting device of claim 16, wherein the organic light emitting device is an organic light emitting display device or an organic light emitting illumination device.

* * * * *